US010287604B2

(12) United States Patent
Kondo et al.

(10) Patent No.: US 10,287,604 B2
(45) Date of Patent: May 14, 2019

(54) GENE FOR INCREASING THE PRODUCTION OF PLANT BIOMASS AND/OR SEEDS AND METHOD FOR USE THEREOF

(71) Applicant: TOYOTA JIDOSHA KABUSHIKI KAISHA, Aichi-ken (JP)

(72) Inventors: Satoshi Kondo, Toyota (JP); Chikara Ohto, Toyota (JP); Norihiro Mitsukawa, Toyota (JP); Nobuhiko Muramoto, Aichi-gun (JP); Kenichi Ogawa, Kyoto (JP); Hiroki Sugimoto, Aichi-gun (JP); Tomoko Tanaka, Aichi-gun (JP); Madoka Yonekura, Toyota (JP)

(73) Assignee: TOYOTA JIDOSHA KABUSHIKI KAISHA, Toyota-shi, Aichi-ken (JP)

( * ) Notice: Subject to any disclaimer, the term of this patent is extended or adjusted under 35 U.S.C. 154(b) by 0 days.

(21) Appl. No.: 15/484,606

(22) Filed: Apr. 11, 2017

(65) Prior Publication Data

US 2017/0283825 A1 Oct. 5, 2017

Related U.S. Application Data

(62) Division of application No. 14/609,830, filed on Jan. 30, 2015, now Pat. No. 9,695,435, which is a division of application No. 12/922,432, filed as application No. PCT/JP2009/054953 on Mar. 13, 2009.

(30) Foreign Application Priority Data

Mar. 14, 2008 (JP) ................................ 2008-066460

(51) Int. Cl.
*C12N 15/82* (2006.01)
*C12N 9/16* (2006.01)

(52) U.S. Cl.
CPC ........... *C12N 15/8261* (2013.01); *C12N 9/16* (2013.01); *C12Y 301/03016* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,176,351 B2 | 2/2007 | Kisaka et al. | |
| 8,575,428 B2 | 11/2013 | Kondo et al. | |
| 9,155,368 B2 * | 10/2015 | Chang .................... | A45C 11/22 |
| 2002/0040490 A1 | 4/2002 | Gorlach et al. | |
| 2003/0135870 A1 | 7/2003 | Cheikh et al. | |
| 2006/0075522 A1 * | 4/2006 | Cleveland ............ | C07K 14/415 800/289 |
| 2006/0123505 A1 | 6/2006 | Kikuchi et al. | |
| 2006/0183137 A1 | 8/2006 | Harper et al. | |
| 2006/0236419 A1 | 10/2006 | La Rosa et al. | |
| 2007/0039067 A1 | 2/2007 | Feldmann et al. | |
| 2007/0136839 A1 | 6/2007 | Cook et al. | |
| 2008/0090998 A1 | 4/2008 | Abad et al. | |
| 2009/0300797 A1 | 12/2009 | Ogawa et al. | |
| 2010/0016166 A1 | 1/2010 | Ogawa et al. | |
| 2010/0083404 A1 | 4/2010 | Ogawa et al. | |
| 2011/0078818 A1 | 3/2011 | Kondo et al. | |
| 2012/0005787 A1 | 1/2012 | Kondo et al. | |
| 2012/0159666 A1 | 6/2012 | Yokekura et al. | |
| 2017/0037426 A1 * | 2/2017 | Alexandrov ......... | C07K 14/415 |

FOREIGN PATENT DOCUMENTS

| | | | |
|---|---|---|---|
| JP | 9-503389 | A | 4/1997 |
| JP | 2000-515020 | A | 11/2000 |
| JP | 2001-505410 | A | 4/2001 |
| JP | 2001-519659 | A | 10/2001 |
| JP | 2005-052114 | A | 3/2005 |
| JP | 2005-130770 | A | 5/2005 |
| JP | 2005185101 | A | 7/2005 |
| JP | 2007-530063 | A | 11/2007 |
| WO | 95/09911 | A1 | 4/1995 |
| WO | 98/03631 | A1 | 1/1998 |
| WO | 98/10082 | A1 | 3/1998 |
| WO | 98/42851 | A1 | 10/1998 |
| WO | 02/10210 | A1 | 2/2002 |
| WO | 2005/094562 | A1 | 10/2005 |
| WO | 2006076423 | A2 | 7/2006 |
| WO | 2007091634 | A1 | 8/2007 |
| WO | 2008034648 | A1 | 3/2008 |
| WO | 2008082602 | | 7/2008 |
| WO | 2008087932 | A1 | 7/2008 |
| WO | 2009113684 | A1 | 9/2009 |

OTHER PUBLICATIONS

Sun et al., J Plant Physiol 212:94-104 (2017).*
Xue et al., BMC Genomics 9:550 (2008).*
Rodriguez, Plant Mol Biol 38(6):919-27 (1998).*
Londo et al., Proc Natl Acad Sci USA 103(25):9578-83 (2006).*
Mendonça Vilela et al., Genome Biol Evol 9(2):266-78 (2017).*
Angela Saez et al., "Gain-of-function and loss-of-function phenotypes of the protein phosphate 2C HAB1 reveal its role as a negative regulator of abscisic acid signaling", The Plant Journal, 2004, pp. 354-369, vol. 37.
Australian Office Action dated Dec. 16, 2011, for Patent Application No. 2009224235.
Bower, et al., "Transgenic sugarcane plants via microprojectile bombardment", The Plant Journal, 2(3), Jan. 13, 1992, pp. 409-416.
Communication, dated Dec. 15, 2016, issued by the United States Patent and Trademark Office in U.S. Appl. No. 12/922,432.

(Continued)

*Primary Examiner* — Russell T Boggs
(74) *Attorney, Agent, or Firm* — Sughrue Mion, PLLC

(57) ABSTRACT

A technique by which the production of plant biomass can be significantly increased is provided. A protein phosphatase 2C gene having 3 consensus sequences comprising the amino acid sequences shown in SEQ ID NOS: 1-3 from the N-terminal side in such order is over-expressed.

18 Claims, 16 Drawing Sheets

Specification includes a Sequence Listing.

(56) References Cited

OTHER PUBLICATIONS

Communication dated Feb. 5, 2015, issued by the United States Patent and Trademark Office in U.S. Appl. No. 13/256,190.
Communication dated Jan. 15, 2016, issued by the U.S. Patent and Trademark Office in U.S. Appl. No. 12/922,432.
Communication dated Nov. 16, 2015, issued by the U.S. Patent and Trademark Office in U.S. Appl. No. 13/256,190.
Communication dated Jul. 8, 2015, issued by the United States Patent and Trademark Office in U.S. Appl. No. 12/922,432.
Communication dated Sep. 20, 2016, issued by the United States Patent and Trademark Office in U.S. Appl. No. 13/256,190.
Communication, dated Jun. 8, 2016, issued by the United States Patent and Trademark Office in U.S. Appl. No. 12/922,432.
Communication, dated May 18, 2016, issued by the United States Patent and Trademark Office in U.S. Appl. No. 13/256,190.
David Reyes et al., "Overexpression of a Protein Phosphatase 2C from Beech Seeds in Arabidopsis Shows Phenotypes Related to Abscisic Acid Responses and Gibberellin Biosynthesis", Plant Physiology, Aug. 2006, pp. 1414-1424, vol. 141.
Fourgoux-Nicol et al., "Isolation of rapeseed genes expressed early and specifically during development of the male gametophyte", Plant Mol Biol 40:857-72 (1999) 16 pages total.
Guo et al., "Protein tolerance to random amino acid change," PNAS, Jun. 22, 2004, vol. 101, No. 25, pp. 9205-9210.
Hu et al., "The Structure and function of Protein Phosphatase 2Cs in Higher Plants", Chinese Journal of Cell Biology, 27:29-34 (2005); with English Abstract.
Kasuga et al., A Combination of the *Arabidopsis* DRE1A Gene and Stress Inducible rd29A Promoter Improved Drought- and Low-Temperature Stress Tolerance in Tobacco by Gene Transfer, Plant Cell Physiology, 45(3):2004, pp. 346-350.
Kim et al., "*Arabidopsis* ORF Clones", Accession No. AAM10415, dated Apr. 13, 2002 (Unpublished), ncbi.nlm.nih.gov/sviewer/viewer.fcgi?tool=portal&sendto=on&log$-seqv . . . (dated Jan. 20, 2012).
Leung et al., "The *Arabidopsis* Abscisic Acid-Insensitive2 (ABI2) and ABI1 Genes Encode Homologous Protein Phosphatases 2C Involved in Abscisic Acid Signal Transduction", The Plant Cell, vol. 9, p. 759-771 American Society of Plant Physiologists (1997).
Koesema et al., "*Arabidopsis* cDNA Clones", Accession No. AAK91405, dated Aug. 20, 2001 (Unpublished), ncbi.nlm.nih.gov/sviewer/viewer.fcgi?tool=portal&sendto=on&log$-seqv . . . (dated Jan. 20, 2012).
Lin et al., "*Arabidopsis thaliana* chromosome III BAC F18C1 Genomic Sequence", Accession No. AAF26133, dated Oct. 30, 2002 (Unpublished), ncbi.nlm.nih.gov/sviewer/viewer.fcgi?tool=portal&sendto=on&log$-seqv . . . (dated Jan. 20, 2012).
Mary Paz Gonzalez-Garcia et al., "Negative Regulation of Abscisic Acid Signaling by the Fagus sylvatica FsPP2C1 Plays a Role in Seed Dormancy Regulation and Promotion of Seed Germination", Plant Physiology, Sep. 2003, pp. 135-144, vol. 133.
Meinhard et al., Hydrogen peroxide is a regulator of ABI1, a protein phosphatase 2C from *Arabidopsis*, FEBS Letters, 508 (2001) pp. 443-446.
Meinkoth et al., "Hybridization of Nucleic Acids Immobilized on Solid Supports," Analytical Biochemistry, 1984, vol. 138, pp. 267-284.
Notice of Allowability for U.S. Appl. No. 14/609,830 dated Jan. 11, 2017.
Radke, et al., "Transformation and regeneration of *Brassica rapa* using Agrobacterium tumefaciens", Plant Cell Reports, 11, (1992), pp. 499-505.
Restriction Requirement issued in U.S. Appl. No. 13/256,190 dated Dec. 16, 2013.
Rizhsky et al., "When Defense Pathways Collide: The Response of *Arabidopsis* to a Combination of Drought and Heat Stress", Plant Physiology, Apr. 2004, 134:1-14.
Roland Schafleitner et al., "Field Screening for Variation of Drought Tolerance in Solanum tuberosum L. by Agronomical, Physiological and Genetic Analysis", Potato Research, 2007, pp. 71-85, vol. 50.
Sato et al., "Structural Analysis of *Arabidopsis thaliana* Chromosomes 3. I. Sequence Features of the Regions of 4,504,864 bp Covered by Sixty P1 and TAC Clones", Accession No. BAA95773, dated Feb. 14, 2004, DNA Res, 7(2):131-135, ncbi.nlm.nih.gov/sviewer/viewer.fcgi?tool=portal&sendto=on&log$-seqv . . . (dated Jan. 20, 2012).
Schweighofer et al., "Plant PP2C phosphatases: emerging functions in stress signaling," Trends in Plant Science, May 2004, vol. 9, No. 5, 236-243.
Sinclair, et al., "Crop transformation and the challenge to increase yield potential", Trends in Plant Science, vol. 9, No. 2, Feb. 2004, pp. 70-75.
Sopory et al., "Protein Kinases and Phosphatases and Their Role in Cellular Signaling in Plants", Critical Reviews in Plant Sciences, 17(3): pp. 245-318 (1998).
Sugimoto et al., "Characterization of a Novel Isoform of *Arabidopsis* PP2C, AtPP2CF1", 21st Int'l Conf Arab Res (2010) 1 page total.
Totoki et al., "Large-Scale Analysis of RIKEN *Arabidopsis* Full-length (RAFL) cDNAs", Accession No. BAF00337, dated Jul. 27, 2006 (Unpublished), ncbi.nlm.nih.gov/sviewer/viewer.fcgi?tool=portal&sendto=on&log$-seqv . . . (dated Jan. 20, 2012).
Umbrasaite et al., Substrate Analysis of *Arabidopsis* PP2C-Type Protein Phosphatases, Chapter 8, pp. 149-161.
Whisstock et al., "Prediction of protein function from protein sequence and structure," Quarterly Review of Biophysics, 2003, vol. 36, No. 3, pp. 307-340.
Zhang, James Z, Overexpression analysis of plant transcription factors, Elsevier, pp. 430-440.
Restriction Requirement, issued by the United States Patent and Trademark Office dated Sep. 15, 2016, in U.S. Appl. No. 14/609,830.
Communication, dated Jan. 11, 2017, issued by the United States Patent and Trademark Office in U.S. Appl. No. 14/609,830.
Communication, dated Feb. 8, 2017, issued by the United States Patent and Trademark Office in U.S. Appl. No. 14/609,830.
Communication, dated Apr. 4, 2017, issued by the United States Patent and Trademark Office in U.S. Appl. No. 14/609,830.
Communication, dated Feb. 9, 2018, issued by the U.S. Patent and Trademark Office in U.S. Appl. No. 12/922,432.
Gene Model: AT3G05640.1; TAIR website, retrieved from https://arabidopsis.org/servlets/TairObject?type=gene&id=37628 on Jan. 29, 2018, 7 pages total.
Communication, dated Apr. 13, 2017, issued by the United States Patent and Trademark Office in U.S. Appl. No. 12/922,432.
Kuhn, J., et al., "The Protein Phosphatase AtPP2CA Negatively Regulates Abscisic Acid Signal Transduction in *Arabidopsis*, and Effects of abh1 on AtPP2CA mRNA[1[W]]", *Plant Physiology*, Jan. 2006, vol. 140, pp. 127-139 (13 pages).
Communication, dated Oct. 25, 2018, issued by the United States Patent and Trademark Office in , issued in counterpart application, U.S. Appl. No. 12/922,432.
Hiroki Sugimoto, et al. "Overexpression of a novel *Arabidopsis* PP2C isoform, AtPP2CF1, enhances plant biomass production by increasing inflorescence stem growth", Journal of Experimental Botany, 2014: vol. 65, No. 18, pp. 5385-5400.
Noriyuki Nishimura, et al. "PYR/PYL/RCAR family members are major in-vivo ABI1 protein phosphatase 2C-interacting proteins in *Arabidopsis*", The Plant Journal, 2010: vol. 61, pp. 290-299.
Communication, dated Jun. 28, 2018, issued by the U.S. Patent and Trademark Office in counterpart U.S. Appl. No. 15/484,525.
Communication, dated Jul. 6, 2018, issued by U.S. Patent and Trademark Office in counterpart U.S. Appl. No. 15/484,566.
Shavindra Bajaj et al., "Recent advances rice biotechnology—towards genetically superior transgenic rice", *Plant Biotechnology Journal*, 2005, 3: 275-307.
Sunghwa Choe et al., "Overexpression of DWARF4 in the brassinosteroid biosynthetic pathway results in increased vegetative growth and seed yield in *Arabidopsis*", *The Plant Journal*, 2001, 26(6): 573-582.
Tongtong Xue, et al., "Genome-wide and expression analysis of protein phosphatase 2C in rice and *Arabidopsis*", *BMC Genomics*, BioMed Central, 9:550, pp. 1-21.

(56) References Cited

OTHER PUBLICATIONS

Communication, dated Dec. 31, 2018, issued by the U.S. Patent and Trademark Office in U.S. Appl. No. 15/484,525.

* cited by examiner

Fig. 1-1

```
CLUSTAL W (1.83) multiple sequence alignment

AT5G26010      MGHCFSLPS------SQSEIHEDNEHGDGNVVCYGEEFGLDQDLPVH-------------
AT4G32950      MGFCFCLSSG--GSTDKSQIYEITDYGQENAVLYSDHHVVPQN-----------------
AT1G16220      MGLCHSKIDKTTRKETG-ATSTATT--TVERQS-SGRLRRPRDLYSGG------------
AT1G79630      MGLCYS-VDRTTGKEPGEASSTATTAETVEERSGSGRWRRPRDLKGGG------------
At1g03590      ------------MHRPCLGMGCCGS--KMGKRGFSDRMVSLHNLVS--------------
AT3G02750      MGSCLSAE----SRSPRPGSPCSPAFSVRKRKNSKKRPGSRNSSFDYR------------
AT5G36250      MGSCLSSSGGGGSRRSLHGSPHVPGPGRRKRP-PKRRPGSCSSSFDNT------------
AT5G01700      MGVCCS-----------KGTGIIVEHGADDGNECGDGEAEVRDTNDG-------------
AT3G05640      MGHFSS------MFNGIARSFSIKKAKNINSSKSYAKEATDEMAREAK------------
AT5G27930      MGHFSS------MFNGLARSFSIKKVKNNNGN-CDAKEAADEMASEAK------------
AT3G16800      MVLLPA------FLDGLARTVSTKKGKKLSEDEDGGREIAKSMIKDSK------------
AT2G20050      MGCAYSKTCIGQICATKENSIRQTHQQAPSRGGTRATAAAAAVEEDNPVFNFSSDAVDDV
AT3G06270      MGCVQCKCCS-------------RYPSSSSDGDSRGPLEANGVLK---------------

AT5G26010      ------------------------------------------RLGSVCSIQGTKV-----
AT4G32950      -------------------------------------------LGSVSSLAGGKG-----
AT1G16220      ------------------------EISEIQQVVGRLVGNGSSEIACLYTQQGKKG-----
AT1G79630      ------------------------DIEGIPQVLGRLVSNGSSKIACLYTQQGKKG-----
At1g03590      -------------------------------IPNRIIGNGKSRSSCIFTQQGRKG-----
AT3G02750      ------------------------REEPLNQVPGRMFLNGSTEVACIYTQQGKKG-----
AT5G36250      ------------------------EEPLLHRIPGRMFLNGSTDTVSLFSQQGKKG-----
AT5G01700      ---------------------------------AVVRTRGSSKHVSMSIKQGKKG-----
AT3G05640      ------------------------KKELILRSSGCINADGSNNLASVFSRRGEKG-----
AT5G27930      ------------------------KKELILKSSGYVNVQGSNNLASLFSKRGEKG-----
AT3G16800      ------------------------KNSTLLGTSGFVSSESSKRFTSICSNRGEKG-----
AT2G20050      DNDEIHQLGLSRDQEWGITRLSRVSSQFLPPDGSRVVKVPSCNYELRCSFLSQRGYYPDA
AT3G06270      ----------GKDQ---------------KPLGS--IHVPSPNFDMVYSVLSQRGYYPDS
                                                                    . :
                                        |
AT5G26010      ---LNQDHAVLYQGYGTR-DTELCGVFDGHGKNGHMVSKMVRNRLPSVLLALKEELNQES
AT4G32950      ---LNQDAAILHLGYGTE-EGALCGVFDGHGPRGAFVSKNVRNQLPSILLG---HMNNHS
AT1G16220      ---TNQDAMLVWENFCSRSDTVLCGVFDGHGPFGHMVSKRVRDMLPFTLSTQLKTTSGTE
AT1G79630      ---TNQDAMLVFENFCSRDDTVFCGVFDGHGPFGHMVAKKVRDTLPFTLLTQLKMTSESD
At1g03590      ---INQDAMIVWEDFMSK-DVTFCGVFDGHGPHGHLVARKVRDSLPVKLLSLLNSIK-SK
AT3G02750      ---PNQDAMVVWENFGSRTDTIFCGVFDGHGPYGHMVAKRVRDNLPLKLSAYWEAKVPVE
AT5G36250      ---PNQDAMIVWENFGSMEDTVFCGVFDGHGPYGHIVAKRVRDLLPLKLGSHLESYVSPE
AT5G01700      ---INQDAMTVWENFGGEEDTIFCGVFDGHGPMGHKISRHVCENLPSRVHSKIRSSKSAG
AT3G05640      ---VNQDCAIVWEGYGCQEDMIFCGIFDGHGPWGHFVSKQVRNSMPISLLCNWKETLSQT
AT5G27930      ---VNQDCALVWEGFGCQEDMIFCGIFDGHGPWGHYVAKQVRNSMPLSLLCNWQKILAQA
AT3G16800      ---INQDRAIVWEGFGCQEDITFCGMFDGHGPWGHVIAKRVKKSFPSSLLCQWQQTLASL
AT2G20050      LDKANQDSFAIHTPFGSNSDDHFFGVFDGHGEFGAQCSQFVKRRLCENLLRHGRFRVDPA
AT3G06270      PDKENQDTYCIKTELQGNPNVHFFGVFDGHGVLGTQCSNFVKERVVEMLSEDPTLLEDPE
                  ***    :          :  : *:*****   *     :.  *   .   :

AT5G26010      NVCEEEAS---------------------------------------------------K
AT4G32950      -VTRDWKL---------------------------------------------------I
AT1G16220      QSSSKNGLNSAPTCVDEE---------------------QWCELQLCEKDEKLFPEMYLP
AT1G79630      QSSLVGANGFQIKCTEEEEVQTTESEQVQKTESVTTMDEQWCELNPVNND-ELPEMYLP
At1g03590      QNGPIGTRASKSDSLEAE-------------------------KEESTEED----KLNFL
AT3G02750      GVLKAITTDTVNNVTNINNPEDAAAAAFVTAE----EEPRTSADMEEENTETQPELFQT
AT5G36250      EVLKEISLNTDD--------RKISEDLVHISAN----GESRVYN---KDYVKDQ-DMIQM
AT5G01700      DENIENNSSQSQE------------------------------------------ELFRE
AT3G05640      TIA------EPDKELQR----------------------------------------FAI
AT5G27930      TLEPELDLEGSNKKISR----------------------------------------FDI
AT3G16800      SSS--------PECSSP----------------------------------------FDL
AT2G20050      ------------------------------------------------------------
AT3G06270      ------------------------------------------------------------
```

Fig. 1-2

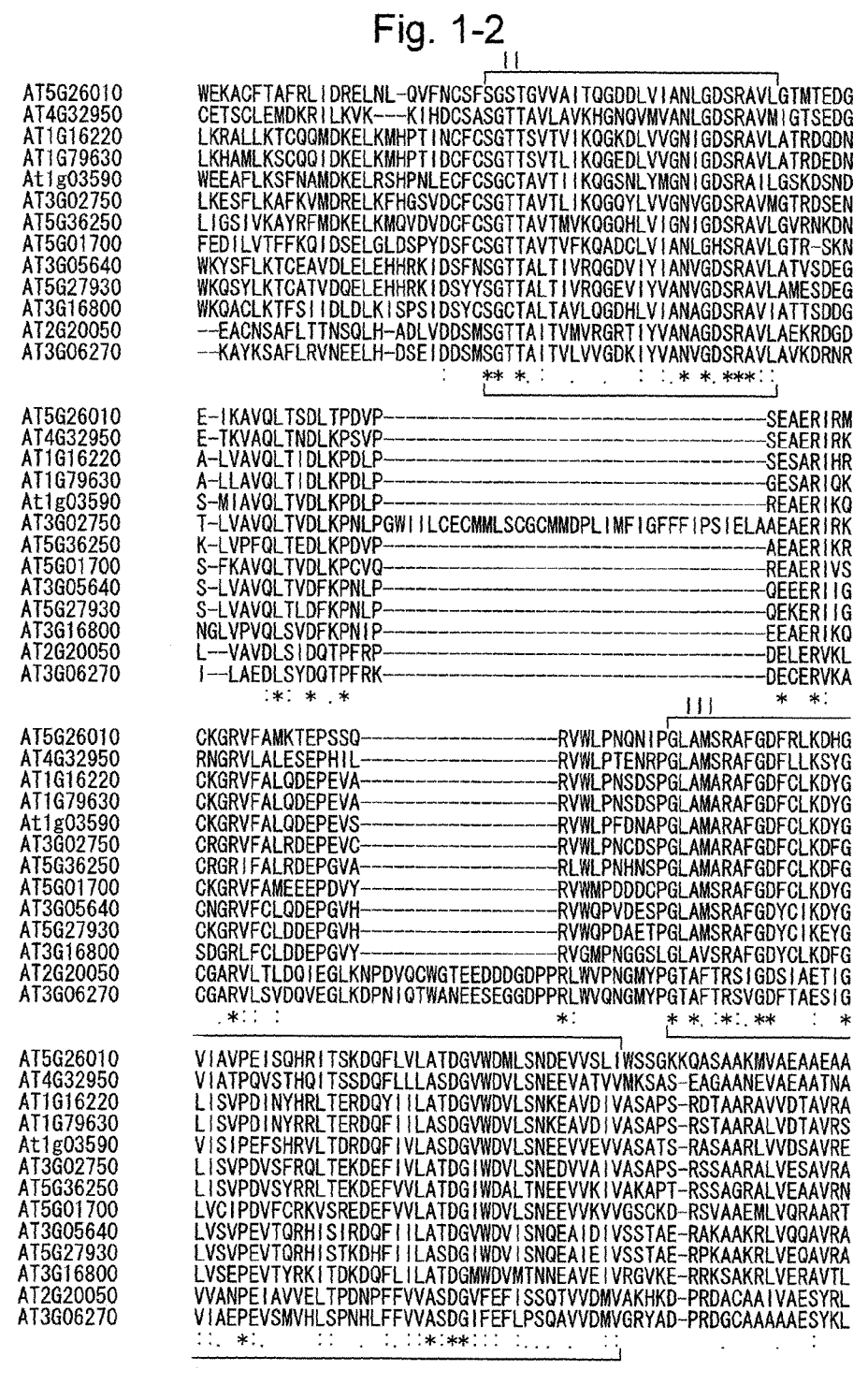

```
AT5G26010    WEKACFTAFRLIDRELNL-QVFNCSFSGSTGVVAITQGDDLVIANLGDSRAVLGTMTEDG
AT4G32950    CETSCLEMDKRILKVK---KIHDCSASGTTAVLAVKHGNQVMVANLGDSRAVMIGTSEDG
AT1G16220    LKRALLKTCQQMDKELKMHPTINCFCSGTTSVTVIKQGKDLVVGNIGDSRAVLATRDQDN
AT1G79630    LKHAMLKSCQQIDKELKMHPTIDCFCSGTTSVTLIKQGEDLVVGNIGDSRAVLATRDEDN
At1g03590    WEEAFLKSFNAMDKELRSHPNLECFCSGCTAVTIIKQGSNLYMGNIGDSRAILGSKDSND
AT3G02750    LKESFLKAFKVMDRELKFHGSVDCFCSGTTAVTLIKQGQYLVVGNVGDSRAVMGTRDSEN
AT5G36250    LIGSIVKAYRFMDKELKMQVDVDCFCSGTTAVTMVKQGQHLVIGNIGDSRAVLGVRNKDN
AT5G01700    FEDILVTFFKQIDSELGLDSPYDSFCSGTTAVTVFKQADCLVIANLGHSRAVLGTR-SKN
AT3G05640    WKYSFLKTCEAVDLELEHHRKIDSFNSGTTALTIVRQGDVIYIANVGDSRAVLATVSDEG
AT5G27930    WKQSYLKTCATVDQELEHHRKIDSYYSGTTALTIVRQGEVIYVANVGDSRAVLAMESDEG
AT3G16800    WKQACLKTFSIIDLDLKISPSIDSYCSGCTALTAVLQGDHLVIANAGDSRAVIATTSDDG
AT2G20050    --EACNSAFLTTNSQLH-ADLVDDSMSGTTAITVMVRGRTIYVANAGDSRAVLAEKRDGD
AT3G06270    --KAYKSAFLRVNEELH-DSEIDDSMSGTTAITVLVVGDKIYVANVGDSRAVLAVKDRNR
                                :   ** *.:  .  .    :  :.* *.***::

AT5G26010    E-IKAVQLTSDLTPDVP-----------------------------------SEAERIRM
AT4G32950    E-TKVAQLTNDLKPSVP-----------------------------------SEAERIRK
AT1G16220    A-LVAVQLTIDLKPDLP-----------------------------------SESARIHR
AT1G79630    A-LLAVQLTIDLKPDLP-----------------------------------GESARIQK
At1g03590    S-MIAVQLTVDLKPDLP-----------------------------------REAERIKQ
AT3G02750    T-LVAVQLTVDLKPNLPGWIILCECMMLSCGCMMDPLIMFIGFFFIPSIELAAEAERIRK
AT5G36250    K-LVPFQLTEDLKPDVP-----------------------------------AEAERIKR
AT5G01700    S-FKAVQLTVDLKPCVQ-----------------------------------REAERIVS
AT3G05640    S-LVAVQLTVDFKPNLP-----------------------------------QEEERIIG
AT5G27930    S-LVAVQLTLDFKPNLP-----------------------------------QEKERIIG
AT3G16800    NGLVPVQLSVDFKPNIP-----------------------------------EEAERIKQ
AT2G20050    L--VAVDLSIDQTPFRP-----------------------------------DELERVKL
AT3G06270    I--LAEDLSYDQTPFRK-----------------------------------DECERVKA
                 :*: * .*                                         *  *:

AT5G26010    CKGRVFAMKTEPSSQ------------------RVWLPNQNIPGLAMSRAFGDFRLKDHG
AT4G32950    RNGRVLALESEPHIL------------------RVWLPTENRPGLAMSRAFGDFLLKSYG
AT1G16220    CKGRVFALQDEPEVA------------------RVWLPNSDSPGLAMARAFGDFCLKDYG
AT1G79630    CKGRVFALQDEPEVA------------------RVWLPNSDSPGLAMARAFGDFCLKDYG
At1g03590    CKGRVFALQDEPEVS------------------RVWLPFDNAPGLAMARAFGDFCLKDYG
AT3G02750    CRGRVFALRDEPEVC------------------RVWLPNCDSPGLAMARAFGDFCLKDFG
AT5G36250    CRGRIFALRDEPGVA------------------RLWLPNHNSPGLAMARAFGDFCLKDFG
AT5G01700    CKGRVFAMEEEPDVY------------------RVWMPDDDCPGLAMSRAFGDFCLKDYG
AT3G05640    CNGRVFCLQDEPGVH------------------RVWQPVDESPGLAMSRAFGDYCIKDYG
AT5G27930    CKGRVFCLDDEPGVH------------------RVWQPDAETPGLAMSRAFGDYCIKEYG
AT3G16800    SDGRLFCLDDEPGVY------------------RVGMPNGGSLGLAVSRAFGDYCLKDFG
AT2G20050    CGARVLTLDQIEGLKNPDVQCWGTEEDDGDPPRLWVPNGMYPGTAFTRSIGDSIAETIG
AT3G06270    CGARVLSVDQVEGLKDPNIQTWANEESEGGDPPRLWVQNGMYPGTAFTRSVGDFTAESIG
               .*:: :                          *:       * *.:*:.**    :  *

AT5G26010    VIAVPEISQHRITSKDQFLVLATDGVWDMLSNDEVVSLIWSSGKKQASAAKMVAEAAEAA
AT4G32950    VIATPQVSTHQITSSDQFLLLASDGVWDVLSNEEVATVVMKSAS-EAGAANEVAEAATNA
AT1G16220    LISVPDINYHRLTERDQYIILATDGVWDVLSNKEAVDIVASAPS-RDTAARAVVDTAVRA
AT1G79630    LISVPDINYRRLTERDQFIILASDGVWDVLSNKEAVDIVASAPS-RSTAARALVDTAVRS
At1g03590    VISIPEFSHRVLTDRDQFIVLASDGVWDVLSNEEVVEVVASATS-RASAARLVVDSAVRE
AT3G02750    LISVPDVSFRQLTEKDEFIVLATDGIWDVLSNEDVVAIVASAPS-RSSAARALVESAVRA
AT5G36250    LISVPDVSYRRLTEKDEFVVLATDGIWDALTNEEVVKIVAKAPT-RSSAGRALVEAAVRN
AT5G01700    LVCIPDVFCRKVSREDEFVVLATDGIWDVLSNEEVVKVVGSCKD-RSVAAEMLVQRAART
AT3G05640    LVSVPEVTQRHISIRDQFIILATDGVWDVISNQEAIDIVSSTAE-RAKAAKRLVQQAVRA
AT5G27930    LVSVPEVTQRHISTKDHFIILASDGIWDVISNQEAIEIVSSTAE-RPKAAKRLVEQAVRA
AT3G16800    LVSEPEVTYRKITDKDQFLILATDGMWDVMTNNEAVEIVRGVKE-RRKSAKRLVERAVTL
AT2G20050    VVANPEIAVVELTPDNPFFVVASDGVFEFISSQTVVDMVAKHKD-PRDACAAIVAESYRL
AT3G06270    VIAEPEVSMVHLSPNHLFFVVASDGIFEFLPSQAVVDMVGRYAD-PRDGCAAAAAESYKL
             ::. *:.    ::  .  :.::*:**::: :...  .  ::         .    .   :
```

Fig. 1-3

```
AT5G26010     WKKRLKYTKVDDITVICLFLQNKEQPS---------------------------------
AT4G32950     WIQKFPTVKIDDISVVCLSLNKKHNPQPQI------------------------------
AT1G16220     WRLKYPTSKNDDCAVVCLFLEDTSAGGTVEVSETVNHSHEESTESVTITSSKDADKKEEA
AT1G79630     WRIKYPTSKNDDCTVVCLFLQDSSVAMEVSTNVKKDSPKEESIESVTNSTSKEED-----
At1g03590     WKLKYPTSKMDDCAVVCLFLDG---RMDSETSDNEEQCFSSATNAVESDESQGAEP----
AT3G02750     WRYKYPTSKVDDCAAVCLYLDSSNTNAISTASSISKLEDGEEEELKATTEDDDASG----
AT5G36250     WRWKFPTSKVDDCAVVCLFLDS-EPNRLSTAS----------------------------
AT5G01700     WRTKFPASKADDCAVVVLYLNHRPYPREGNVS----------------------------
AT3G05640     WNRKRRGIAMDDISAVCLFFHSSSSSPSL-------------------------------
AT5G27930     WKKKRRGYSMDDMSVVCLFLHSSSSS-SLSQHHHAMTILK--------------------
AT3G16800     WRRKRRSIAMDDISVLCLFFRPS-------------------------------------
AT2G20050     WLQY--ETRTDDITIIVVHIDGLKDDAPRQLSSTGTQLQPPIPQVVELTGSESPSTFGWN
AT3G06270     WLEH--ENRTDDITIIIVQIKKLSNE----------------------------------
              *         ** : : : :

AT5G26010     ------------------------------------------------------------
AT4G32950     ------------------------------------------------------------
AT1G16220     STETNETVPVWEIKEEKTPESCRIESKKT--TLAECISVK-DDEEWSALEGLTRVNSLLS
AT1G79630     -----EIVP---VKDEKIPESCGIESKMMTMTLAECISVAQDDEEWSALEGLTRVNSLLS
At1g03590     --CLQRNVTVRSLSTDQENNSYGKVIAEA--DNAEKEKTREGEQNWSGLEGVTRVNSLVQ
AT3G02750     -PSGLGRSSTVRSGKEIALDESETEKLIK----EADNLDSEPGTEYSALEGVARVNTLLN
AT5G36250     ------------FSKEKHINNGVTEPEPD----TASSSTPDSGTGSPELNGVNRIDTLVN
AT5G01700     ----------------RAISTISWRSNKS-------NNECYGAAPLSPLGLSQRVS----
AT3G05640     ------------------------------------------------------------
AT5G27930     ------------------------------------------------------------
AT3G16800     ------------------------------------------------------------
AT2G20050     SKNQRVRHDLSRARIRAIENSLENGHAWVPPSPAHRKTWEEEVRVLVCFVFAQPIRNASS
AT3G06270     ------------------------------------------------------------

AT5G26010     ------------------ (SEQ ID NO: 59)
AT4G32950     ------------------ (SEQ ID NO: 60)
AT1G16220     IPRFFSGELRSSSWRKWL (SEQ ID NO: 61)
AT1G79630     IPRFLSGELRSTSWRKWL (SEQ ID NO: 62)
At1g03590     LPRFPGEEPKT------- (SEQ ID NO: 63)
AT3G02750     LPRFVPGK---------- (SEQ ID NO: 42)
AT5G36250     LPVYVPTKE--------- (SEQ ID NO: 64)
AT5G01700     ------------------ (SEQ ID NO: 65)
AT3G05640     ------------------ (SEQ ID NO: 5)
AT5G27930     ------------------ (SEQ ID NO: 36)
AT3G16800     ------------------ (SEQ ID NO: 48)
AT2G20050     HSYIRRLNAGFSRAGTH- (SEQ ID NO: 66)
AT3G06270     ------------------ (SEQ ID NO: 67)
```

Fig. 2-1

```
CLUSTAL W (1.83) multiple sequence alignment


AT1G16220       MGLCHSKIDKTTRKETG-ATSTATT--TVERQS-SGRLRRPRDLYSGGEISEIQQVVGRL
AT1G79630       MGLCYS-VDRTTGKEPGEASSTATTAETVEERSGSGRWRRPRDLKGGGDIEGIPQVLGRL
At1g03590       ------------MHRPCLGMCCGS--KMGKRGFSDRMVSLHNLVS----------IPNRI
AT3G02750       MGSCLSAE----SRSPRPGSPCSPAFSVRKRKNSKKRPGSRNSSFDYRREEPLNQVPGRM
AT5G36250       MGSCLSSSGGGGSRRSLHGSPHVPGPGRRKRP-PKRRPGSCSSSFDNTEEPLLHRIPGRM
AT5G26010       MGHCFSLPS----SQSEIHEDNEHGDG-NVVCYGEEFGLDQDLPVH--------------
AT4G32950       MGFCFCLSSGGSTDKSQIYEITDYGQE-NAVLYSDHHVVPQN------------------
AT5G01700       MGVCCSKGTG-IIVEHGADDGNECGDGEAEVRDTNDGAVVRTRGSS--------------
AT3G05640       MGHFSSMFNGIARSFSIKKAKNINSSKSYAKEATDEMAREAKKKELILR------SSGCI
AT5G27930       MGHFSSMFNGLARSFSIKKVKNNNGN-CDAKEAADEMASEAKKKELILK------SSGYV
AT3G16800       MVLLPAFLDGLARTVSTKKGKKLSEDEDGGREIAKSMIKDSKKNSTLLG------TSGFV

                                                          I

AT1G16220       VGNGSSEIACLYTQQGKKGTNQDAMLVWENFCSRSDTVLCGVFDGHGPFGHMVSKRVRDM
AT1G79630       VSNGSSKIACLYTQQGKKGTNQDAMLVFENFCSRDDTVFCGVFDGHGPFGHMVAKKVRDT
At1g03590       IGNGKSRSSCIFTQQGRKGINQDAMIVWEDFMSK-DVTFCGVFDGHGPHGHLVARKVRDS
AT3G02750       FLNGSTEVACIYTQQGKKGPNQDAMVVWENFGSRTDTIFCGVFDGHGPYGHMVAKRVRDN
AT5G36250       FLNGSTDTVSLFSQQGKKGPNQDAMIVWENFGSMEDTVFCGVFDGHGPYGHIVAKRVRDL
AT5G26010       ------RLGSVCSIQGTKVLNQDHAVLYQGYG-TRDTELCGVFDGHGKNGHMVSKMVRNR
AT4G32950       -------LGSVSSLAGGKGLNQDAAILHLGYG-TEEGALCGVFDGHGPRGAFVSKNVRNQ
AT5G01700       ------KHVSMSIKQGKKGINQDAMTVWENFGGEEDTIFCGVFDGHGPMGHKISRHVCEN
AT3G05640       NADGSNNLASVFSRRGEKGVNQDCAIVWEGYGCQEDMIFCGIFDGHGPWGHFVSKQVRNS
AT5G27930       NVQGSNNLASLFSKRGEKGVNQDCALVWEGFGCQEDMIFCGIFDGHGPWGHYVAKQVRNS
AT3G16800       SSESSKRFTSICSNRGEKGINQDRAIVWEGFGCQEDITFCGMFDGHGPWGHVIAKRVKKS
                        .:    * *  ***    :  .:     :  :**:*****  *  ::: *

AT1G16220       LPFTLSTQLKTTSGTEQSSSKNGLNSAPTCVDEE---------------------QWCEL
AT1G79630       LPFTLLTQLKMTSESDQSSLVGANGFQIKCTEEEEVQTTESEQVQKTESVTTMDEQWCEL
At1g03590       LPVKLLSLLNSIK-SKQNGPIGTRASKSDSLEAE-------------------------K
AT3G02750       LPLKLSAYWEAKVPVEGVLKAITTDTVNNVTNINNPEDAAAAAAFVTAEEEPRTSADMEE
AT5G36250       LPLKLGSHLESYVSPEEVLKEISLNTDD--------RKISEDLVHISANGESRVYN---K
AT5G26010       LPSVLLALK----------EELNQESNVCE------------------------------
AT4G32950       LPSILLG------------HMNNHS-VTR-------------------------------
AT5G01700       LPSRVHSKIRSSKSAGDENIENNSSQSQE-------------------------------
AT3G05640       MPISLLCNWK--------ETLSQTTIA---------------------------------
AT5G27930       MPLSLLCNWQ--------KILAQATLEPE-------------------------------
AT3G16800       FPSSLLCQWQ--------QTLASLSSS---------------------------------
                :*   :
                                                               II

AT1G16220       QLCEKDEKLFPEMYLPLKRALLKTCQQMDKELKMHPTINCFCSGTTSVTVIKQGKDLVVG
AT1G79630       NPNVNND-ELPEMYLPLKHAMLKSCQQIDKELKMHPTIDCFCSGTTSVTLIKQGEDLVVG
At1g03590       EESTEED-----KLNFLWEEAFLKSFNAMDKELRSHPNLECFCSGCTAVTIIKQGSNLYMG
AT3G02750       ENTETQP-----ELFQTLKESFLKAFKVMDRELKFHGSVDCFCSGTTAVTLIKQGQYLVVG
AT5G36250       DYVKDQ------DMIQMLIGSIVKAYRFMDKELKMQVDVDCFCSGTTAVTMVKQGQHLVIG
AT5G26010       ------------EEASKWEKACFTAFRLIDRELNL-QVFNCSFSGSTGVVAITQGDDLVIA
AT4G32950       ------------DWKLICETSCLEMDKRILKVK---KIHDCSASGTTAVLAVKHGNQVMVA
AT5G01700       ------------ELFREFEDILVTFFKQIDSELGLDSPYDSFCSGTTAVTVFKQADCLVIA
AT3G05640       ------EPDKELQRFAIWKYSFLKTCEAVDLELEHHRKIDSFNSGTTALTIVRQGDVIYIA
AT5G27930       -LDLEGSNKKISRFDIWKQSYLKTCATVDQELEHHRKIDSYYSGTTALTIVRQGEVIYVA
AT3G16800       -------PECSSPFDLWKQACLKTFSIIDLDLKISPSIDSYCSGCTALTAVLQGDHLVIA
                            .        .       :             :.  ** *.:  .  :.,  : :.
```

Fig. 2-2

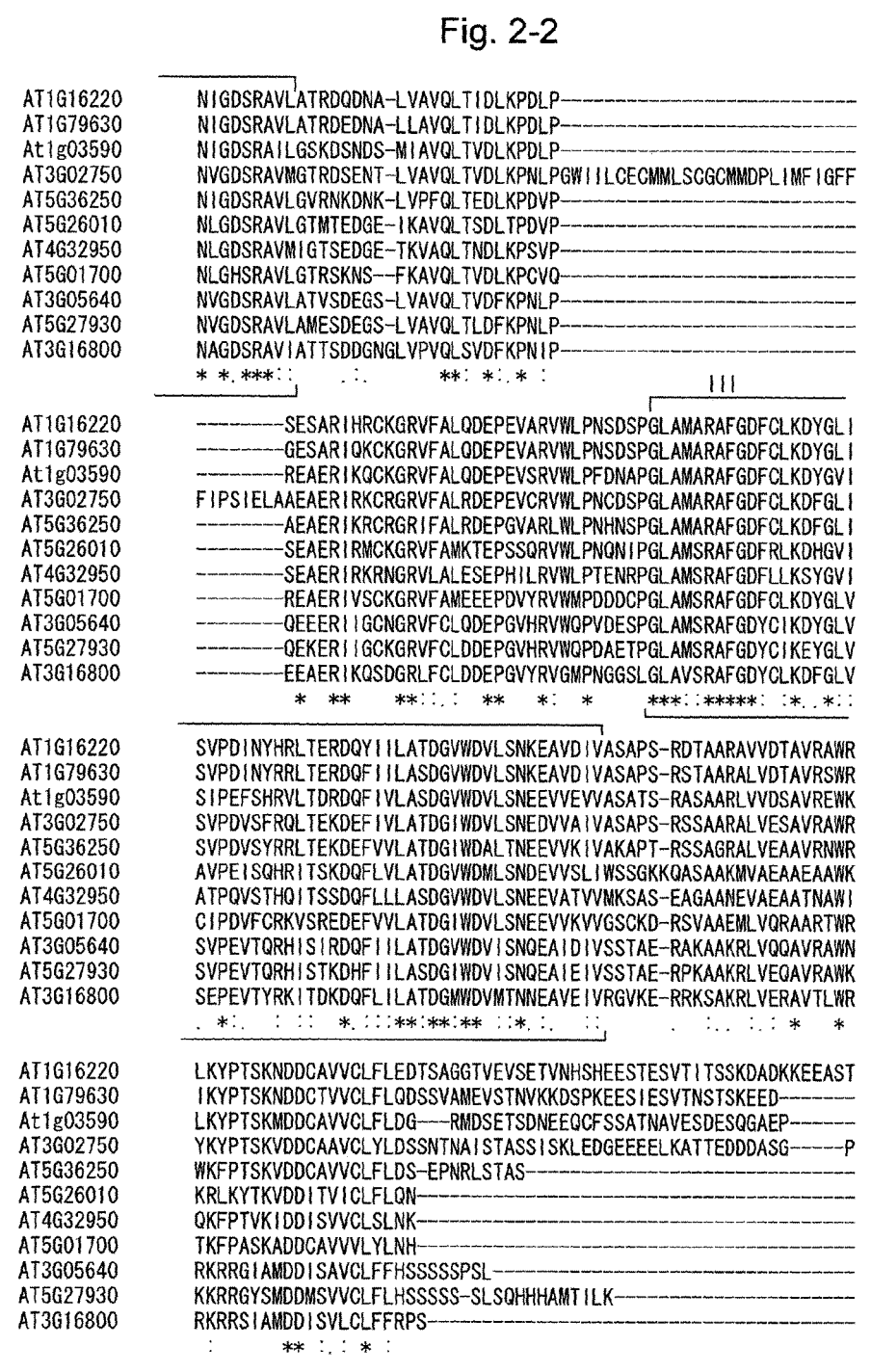

```
AT1G16220      NIGDSRAVLATRDQDNA-LVAVQLTIDLKPDLP---------------------------
AT1G79630      NIGDSRAVLATRDEDNA-LLAVQLTIDLKPDLP---------------------------
At1g03590      NIGDSRAILGSKDSNDS-MIAVQLTVDLKPDLP---------------------------
AT3G02750      NVGDSRAVMGTRDSENT-LVAVQLTVDLKPNLPGWIILCECMMLSCGCMMDPLIMFIGFF
AT5G36250      NIGDSRAVLGVRNKDNK-LVPFQLTEDLKPDVP---------------------------
AT5G26010      NLGDSRAVLGTMTEDGE-IKAVQLTSDLTPDVP---------------------------
AT4G32950      NLGDSRAVMIGTSEDGE-TKVAQLTNDLKPSVP---------------------------
AT5G01700      NLGHSRAVLGTRSKNS--FKAVQLTVDLKPCVQ---------------------------
AT3G05640      NVGDSRAVLATVSDEGS-LVAVQLTVDFKPNLP---------------------------
AT5G27930      NVGDSRAVLAMESDEGS-LVAVQLTLDFKPNLP---------------------------
AT3G16800      NAGDSRAVIATTSDDGNGLVPVQLSVDFKPNIP---------------------------
               * *.***::    .:.        **: *:.* :
                                                         III

AT1G16220      --------SESARIHRCKGRVFALQDEPEVARVWLPNSDSPGLAMARAFGDFCLKDYGLI
AT1G79630      --------GESARIQKCKGRVFALQDEPEVARVWLPNSDSPGLAMARAFGDFCLKDYGLI
At1g03590      --------REAERIKQCKGRVFALQDEPEVSRVWLPFDNAPGLAMARAFGDFCLKDYGVI
AT3G02750      FIPSIELAAEAERIRKCRGRVFALRDEPEVCRVWLPNCDSPGLAMARAFGDFCLKDFGLI
AT5G36250      --------AEAERIKRCRGRIFALRDEPGVARLWLPNHNSPGLAMARAFGDFCLKDFGLI
AT5G26010      --------SEAERIRMCKGRVFAMKTEPSSQRVWLPNQNIPGLAMSRAFGDFRLKDHGVI
AT4G32950      --------SEAERIRKRNGRVLALESEPHILRVWLPTENRPGLAMSRAFGDFLLKSYGVI
AT5G01700      --------REAERIVSCKGRVFAMEEEPDVYRVWMPDDDCPGLAMSRAFGDFCLKDYGLV
AT3G05640      --------QEEERIIGCNGRVFCLQDEPGVHRVWQPVDESPGLAMSRAFGDYCIKDYGLV
AT5G27930      --------QEKERIIGCKGRVFCLDDEPGVHRVWQPDAETPGLAMSRAFGDYCIKEYGLV
AT3G16800      --------EEAERIKQSDGRLFCLDDEPGVYRVGMPNGGSLGLAVSRAFGDYCLKDFGLV
                          *  **    **:.:  **   *:  *    ***::*****: :*..*::

AT1G16220      SVPDINYHRLTERDQYIILATDGVWDVLSNKEAVDIVASAPS-RDTAARAVVDTAVRAWR
AT1G79630      SVPDINYRRLTERDQFIILASDGVWDVLSNKEAVDIVASAPS-RSTAARALVDTAVRSWR
At1g03590      SIPEFSHRVLTDRDQFIVLASDGVWDVLSNEEVVEVVASATS-RASAARLVVDSAVREWK
AT3G02750      SVPDVSFRQLTEKDEFIVLATDGIWDVLSNEDVVAIVASAPS-RSSAARALVESAVRAWR
AT5G36250      SVPDVSYRRLTEKDEFVVLATDGIWDALTNEEVVKIVAKAPT-RSSAGRALVEAAVRNWR
AT5G26010      AVPEISQHRITSKDQFLVLATDGVWDMLSNDEVVSLIWSSGKKQASAAKMVAEAAEAAWK
AT4G32950      ATPQVSTHQITSSDQFLLLASDGVWDVLSNEEVATVVMKSAS-EAGAANEVAEAATNAWI
AT5G01700      CIPDVFCRKVSREDEFVVLATDGIWDVLSNEEVVKVVGSCKD-RSVAAEMLVQRAARTWR
AT3G05640      SVPEVTQRHISIRDQFIILATDGVWDVISNQEAIDIVSSTAE-RAKAAKRLVQQAVRAWN
AT5G27930      SVPEVTQRHISTKDHFIILASDGIWDVISNQEAIEIVSSTAE-RPKAAKRLVEQAVRAWK
AT3G16800      SEPEVTYRKITDKDQFLILATDGMWDVMTNNEAVEIVRGVKE-RRKSAKRLVERAVTLWR
               . *:.   : ::  *.:::**:**:** ::*.:.    ::      .  :..  :.: *  *

AT1G16220      LKYPTSKNDDCAVVCLFLEDTSAGGTVEVSETVNHSHEESTESVTITSSKDADKKEEAST
AT1G79630      IKYPTSKNDDCTVVCLFLQDSSVAMEVSTNVKKDSPKEESIESVTNSTSKEED-------
At1g03590      LKYPTSKMDDCAVVCLFLDG---RMDSETSDNEEQCFSSATNAVESDESQGAEP------
AT3G02750      YKYPTSKVDDCAAVCLYLDSSNTNAISTASSISKLEDGEEEELKATTEDDDASG-----P
AT5G36250      WKFPTSKVDDCAVVCLFLDS-EPNRLSTAS------------------------------
AT5G26010      KRLKYTKVDDITVICLFLQN----------------------------------------
AT4G32950      QKFPTVKIDDISVVCLSLNK----------------------------------------
AT5G01700      TKFPASKADDCAVVVLYLNH----------------------------------------
AT3G05640      RKRRGIAMDDISAVCLFFHSSSSSPSL---------------------------------
AT5G27930      KKRRGYSMDDMSVVCLFLHSSSSS-SLSQHHHAMTILK----------------------
AT3G16800      RKRRSIAMDDISVLCLFFRPS---------------------------------------
                :       ** :.: * :
```

Fig. 2-3

```
AT1G16220   ETNETVPVWEIKEEKTPESCRIESKKT--TLAECISVK-DDEEWSALEGLTRVNSLLSIP
AT1G79630   ---EIVP---VKDEKIPESCGIESKMMTMTLAECISVAQDDEEWSALEGLTRVNSLLSIP
At1g03590   CLQRNVTVRSLSTDQENNSYGKVIAEA--DNAEKEKTREGEQNWSGLEGVTRVNSLVQLP
AT3G02750   SGLGRSSTVRSGKEIALDESETEKLIK----EADNLDSEPGTEYSALEGVARVNTLLNLP
AT5G36250   ----------FSKEKHINNGVTEPEPD----TASSSTPDSGTGSPELNGVNRIDTLVNLP
AT5G26010   -------------KEQPS------------------------------------------
AT4G32950   -------------KHNPQPQI---------------------------------------
AT5G01700   -------------RPYPREGNVSRAIS-------TISWRSNKSNNECYGAAPLSPLGLSQ
AT3G05640   ------------------------------------------------------------
AT5G27930   ------------------------------------------------------------
AT3G16800   ------------------------------------------------------------

AT1G16220   RFFSGELRSSSWRKWL  (SEQ ID NO: 61)
AT1G79630   RFLSGELRSTSWRKWL  (SEQ ID NO: 62)
At1g03590   RFPGEEPKT-------  (SEQ ID NO: 63)
AT3G02750   RFVPGK----------  (SEQ ID NO: 42)
AT5G36250   VYVPTKE---------  (SEQ ID NO: 64)
AT5G26010   ----------------  (SEQ ID NO: 59)
AT4G32950   ----------------  (SEQ ID NO: 60)
AT5G01700   RVS-------------  (SEQ ID NO: 65)
AT3G05640   ----------------  (SEQ ID NO: 5)
AT5G27930   ----------------  (SEQ ID NO: 36)
AT3G16800   ----------------  (SEQ ID NO: 48)
```

Control Transformed plants

Control Transformed plant

Wild type Transformed plant

Wild type Transformed plant

Wild type

Transformed plants

Wild type

Transformed plants

GENE FOR INCREASING THE PRODUCTION OF PLANT BIOMASS AND/OR SEEDS AND METHOD FOR USE THEREOF

CROSS REFERENCE TO RELATED APPLICATIONS

This is a divisional of U.S. patent application Ser. No. 14/609,830, filed Jan. 30, 2015, which is a divisional of U.S. patent application Ser. No. 12/922,432 filed on Dec. 3, 2010, which is a National Stage of International Application No. PCT/JP2009/054953 filed Mar. 13, 2009, claiming priority based on Japanese Patent Application No. JP 2008-066460 filed Mar. 14, 2008, the contents of all of which are incorporated herein by reference in their entirety.

TECHNICAL FIELD

The present invention relates to: a plant in which a given gene is over-expressed; a method for increasing the production of biomass and/or seeds through overexpression of a given gene; and a method for producing such plant capable of producing an increased amount of biomass and/or seeds.

BACKGROUND ART

The term “biomass” generally refers to the total amount of organisms that inhabit or exist in a given area. When such term is used with regard to plants, in particular, it refers to dry weight per unit area. Biomass units are quantified in terms of mass or energy. The expression “biomass” is synonymous with “Seibutsutairyo” or “Seibutsuryo.” In the case of plant biomass, the term “standing crop” is occasionally used for “biomass.” Since plant biomass is generated by fixing atmospheric carbon dioxide with the use of solar energy, it can be regarded as so-called “carbon-neutral energy.” Accordingly, an increase of plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as fats and oils. Examples of fats and oils produced from plants that have been heretofore known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used as raw materials for biodiesel fuel or bioplastic, and the applicability thereof is increasing for alternative energy to petroleum.

In particular, an energy crop such as sugar cane can be used as a raw material for biofuel. Hence, the increased production of the total mass of a plant itself (the amount of plant biomass) is expected. Under such circumstances, improvement in productivity per unit of cultivation area is required in order to increase the production of the amount of plant biomass. It has been found that if the number of cultivated plants is assumed to be constant per unit of cultivation area, improvement in the amount of biomass per plant would be necessary.

However, it is thought that since many genes are involved in the amount of plant biomass (a so-called “kind of quantitative trait”), individual gene introduction or individual genetic modification cannot lead to an effective increase in production. Meanwhile, a great deal of difficulties are associated with introduction of many genes in a desired state into a plant. Such gene introduction is also problematic in that if successful introduction takes place, desirable traits cannot always be acquired.

Various gene introduction techniques are known as techniques for increasing the production of plant biomass, as disclosed in Patent Documents 1-7, for example. However, none of these techniques can be said to exert sufficient effects of increasing the production of biomass.

PATENT DOCUMENTS

Patent Document 1: JP Patent Publication (Kohyo) No. 2001-505410 A

Patent Document 2: JP Patent Publication (Kohyo) No. 2001-519659 A

Patent Document 3: JP Patent Publication (Kohyo) No. 2007-530063 A

Patent Document 4: JP Patent Publication (Kokai) No. 2005-130770 A

Patent Document 5: JP Patent Publication (Kohyo) No. 2000-515020 A

Patent Document 6: JP Patent Publication (Kohyo) No. 9-503389 A

Patent Document 7: JP Patent Publication (Kokai) No. 2005-52114 A

DISCLOSURE OF THE INVENTION

Object to be Achieved by the Invention

In view of the above circumstances, an object of the present invention is to search for genes having novel functions of drastically improving the amount of plant biomass and thus to provide a technique with which the production of plant biomass can be drastically increased.

Means to Achieve the Object

As a result of intensive studies to achieve the above object, the present inventors have made the novel finding that the production of plant biomass can be drastically increased by causing overexpression of a gene encoding protein phosphatase 2C having characteristic consensus sequences. Thus, they have completed the present invention.

Specifically, the plant according to the present invention is a plant in which a gene encoding protein phosphatase 2C having 3 consensus sequences comprising the amino acid sequences shown in SEQ ID NOS: 1-3 from the N-terminal side in such order is over-expressed.

Also, the method for increasing the production of biomass according to the present invention comprises causing the overexpression of a gene encoding protein phosphatase 2C having 3 consensus sequences comprising the amino acid sequences shown in SEQ ID NOS: 1-3 from the N-terminal side in such order.

Furthermore, the method for producing a plant according to the present invention comprises the steps of:

preparing a transformed plant in which a gene encoding protein phosphatase 2C having 3 consensus sequences comprising the amino acid sequences shown in SEQ ID NOS: 1-3 from the N-terminal side in such order is over-expressed; and measuring the amount of biomass of a progeny plant of the transformed plant and then selecting a line in which the amount of biomass is significantly improved.

In the present invention, the above gene encoding protein phosphatase 2C can be at least one type of gene selected from the group consisting of At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), At5g27930-AtPP2C6-7 (SEQ ID NO:36), At2g20050 (SEQ ID NO:66), and At3g06270 (SEQ ID NO:67), or a gene functionally equivalent thereto.

In the present invention, the gene encoding protein phosphatase 2C preferably encodes any one of the following proteins (a) to (c):

(a) a protein comprising an amino acid sequence selected from the group consisting of SEQ ID NOS: 5, 7, 36, 42, and 48;

(b) a protein comprising an amino acid sequence that has a deletion, a substitution, an addition, or an insertion of one or a plurality of amino acids with respect to an amino acid sequence selected from the group consisting of SEQ ID NOS: 5, 7, 36, 42, and 48 and having protein phosphatase 2C activity; and (c) a protein that is encoded by a polynucleotide hybridizing under stringent conditions to a polynucleotide comprising a nucleotide sequence complementary to a nucleotide sequence selected from the group consisting of SEQ ID NOS: 4, 6, 35, 41, and 47 and has protein phosphatase 2C activity.

Also, in the present invention, an example of the above functionally equivalent gene is a protein phosphatase 2C gene from an organism other than *Arabidopsis thaliana*. Another example of an organism other than *Arabidopsis thaliana* is an organism selected from the group consisting of rice (*Oryza sativa*), black cottonwood (*Populus trichocarpa*), european grape (*Vitis vinifera*), *Medicago truncatula* (*Medicago truncatula*), alfalfa (*Medicago sativa*), *Physcomitrella patens* (*Physcomitrella patens*), ice plant (*Mesembryanthemum crystallinum*), *Chlamydomonas reinhardtii* (*Chlamydomonas reinhardtii*), corn (*Zea mays*), rapeseed (*Brassica rapa*), tomato (*Solanum lycopersicum*), monkey flower (*Mimulus guttatus*), and monocellular red alga (*Cyanidioschyzon merolae*).

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

Effect of the Invention

The plant according to the present invention is a plant capable of producing significantly improved amount of biomass and/or seeds compared with wild-type plants. Also, the method for increasing the production of biomass and/or seeds according to the present invention can realize the significantly increased production of biomass and/or seeds compared with target wild-type plants. Furthermore, the method for producing a plant according to the present invention makes it possible to produce a plant capable of producing significantly improved amount of biomass and/or seeds compared with wild-type plants. Therefore, through application of the present invention, for example, productivity can be improved when the plant itself is a product and this can be achieved at lower cost. Also, through application of the present invention, for example, the productivity can be improved when seeds are directly products or ingredients contained in seeds are directly products and this can be achieved at lower cost.

This description hereby incorporates the entire content of the description and/or the drawings of Japanese Patent Application No. 2008-066460, which is the basis of the priority claim of this application.

BRIEF DESCRIPTION OF THE DRAWINGS

FIGS. 1-1, 1-2 and 1-3 are characteristic diagrams showing the results of alignment analysis using a CLUSTAL W (1.83) multiple sequence alignment program for amino acid sequences encoded by At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), At5g27930-AtPP2C6-7 (SEQ ID NO:36), At2g20050 (SEQ ID NO:66), and At3g06270 (SEQ ID NO:67).

FIGS. 2-1, 2-2 and 2-3 are characteristic diagrams showing the results of alignment analysis using a CLUSTAL W (1.83) multiple sequence alignment program for amino acid sequences encoded by At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), and At5g27930-AtPP2C6-7 (SEQ ID NO:36).

FIG. 3 is a photo showing the above-ground parts of wild-type plants and transformed plants into which a fragment containing ORF of the PP2C (protein phosphatase 2C) gene (At3g05640 (SEQ ID NO:5)) was introduced.

BEST MODE FOR CARRYING OUT THE INVENTION

The present invention will be described in detail as follows.

The plant according to the present invention is a plant in which: a gene encoding protein phosphatase 2C having characteristic consensus sequences is over-expressed; and the amount of biomass is significantly improved compared with wild-type plants. The plant according to the present invention may be a plant in which the protein phosphatase 2C gene is over-expressed in all plant tissues or at least some plant tissues. Here, the term "plant tissue(s)" refers to plant organ(s) such as leaves, stems, seeds, roots, and flowers.

Here, the term "overexpression" refers to an expression level that can be confirmed as a transcript as a result of transcription of the protein phosphatase 2C gene introduced into a plant.

Protein Phosphatase 2C Gene

The protein phosphatase 2C gene to be over-expressed in a plant encodes protein phosphatase 2C that has 3 consensus sequences comprising the amino acid sequences shown in SEQ ID NOS: 1-3 in such order from the N-terminal side. In addition, a gene group classified as Group E as in FIG. 1 of Topographic cladogram (on page 237 of Reference: TRENDS in Plant Science Vol. 9 No. 5 May 2004 pages 236-243) encodes protein phosphatase 2C having 3 consensus sequences comprising the amino acid sequences shown in SEQ ID NOS: 1-3 in such order from the N-terminal side. In addition, the reference predicts the presence of 76 protein phosphatase 2C genes in *Arabidopsis thaliana* and discloses the results of producing a phylogenetic tree of these genes using T-Coffee software (reference; Notredame, C. et al. 2000 T-Coffee: a novel method for fast and accurate multiple sequence alignment. J. Mol. Biol. 302, 205-247) as in FIGS. 1-1, 1-2 and 1-3. In this phylogenetic tree, protein phosphatase 2C genes classified as members of Group E encode protein phosphatase 2C that has 3 consensus sequences comprising the amino acid sequences shown in SEQ ID NOS: 1-3 in such order from the N-terminal side. The 3 consensus sequences comprising the amino acid sequences shown in SEQ ID NOS: 1-3 are characteristic sequences in Group E in the above-mentioned classification and serve as a basis for clear differentiation from other groups.

Figure 3:
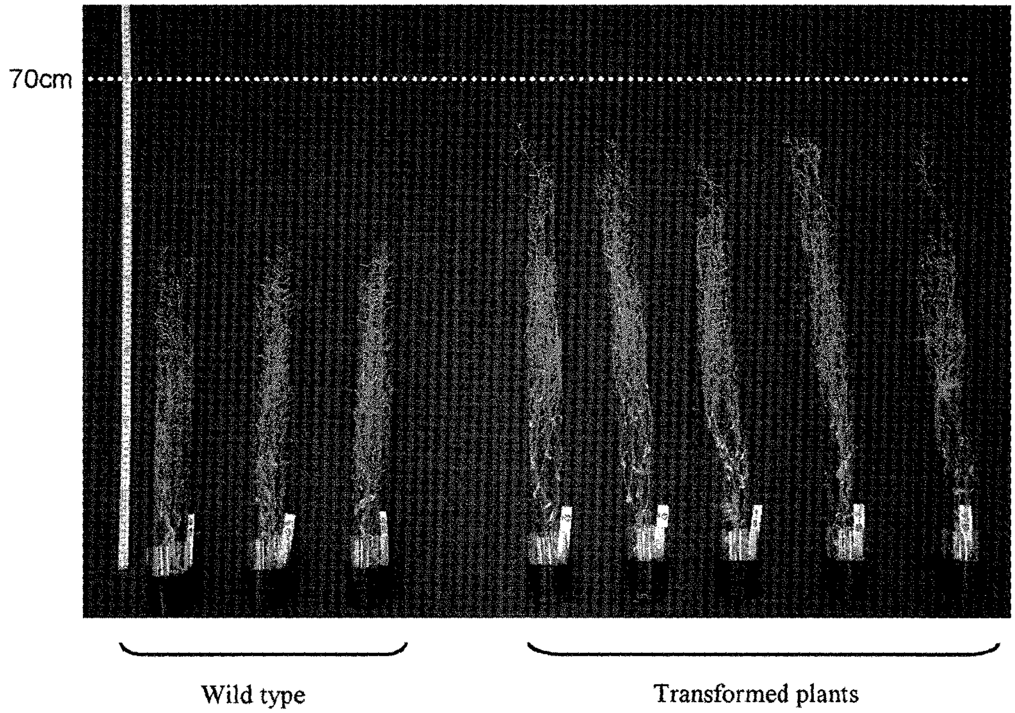

Group E in the above classification includes protein phosphatase 2C genes specified by *Arabidopsis thaliana*-derived At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), At5g27930-AtPP2C6-7 (SEQ ID NO:36), At2g20050 (SEQ ID NO:66), and At3g06270 (SEQ ID NO:67). FIGS. 1-1, 1-2 and 1-3 show the results of alignment analysis using a CLUSTAL W (1.83) multiple sequence alignment program (which can be used with the DDBJ of the National Institute of Genetics (on world wide web at clustalw.ddbj.nig.ac.jp/top-j)) for the amino acid sequences encoded by these *Arabidopsis thaliana*-derived protein phosphatase 2C genes, At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), At5g27930-AtPP2C6-7 (SEQ ID NO:36), At2g20050 (SEQ ID NO:66), and At3g06270 (SEQ ID NO:67) (with the amino acid (sequence) substitution matrix used herein being a default matrix known as BLOSUM (Blocks of Amino Acid Substitution Matrix)). As shown in FIGS. 1-1, 1-2 and 1-3, these protein phosphatase 2C genes classified as members of Group E have consensus sequences characteristic in the regions denoted as I to III. These regions denoted as I to III are subjected with a rice-derived protein phosphatase 2C gene (described later) to alignment analysis, so that the 3 consensus sequences comprising the amino acid sequences shown in SEQ ID NOS: 1-3 can be defined.

Herein, in the amino acid sequence shown in SEQ ID NO: 1, which is an amino acid residue denoted as "Xaa," may be any amino acid, and it is not limited to any particular amino acid. However, the $1^{st}$ amino acid residue from the N-terminal side in the amino acid sequence shown in SEQ ID NO: 1 is preferably leucine (three character code: Leu and single character code: L; the same applies to the following) or phenylalanine (Phe, F). The $4^{th}$ amino acid residue from the N-terminal side in the amino acid sequence shown in SEQ ID NO: 1 is preferably valine (Val, V), isoleucine (Ile, I), or methionine (Met, M). The $16^{th}$ amino acid residue from the N-terminal side in the amino acid sequence shown in SEQ ID NO: 1 is preferably serine (Ser, S) or alanine (Ala, A). The $17^{th}$ amino acid residue from the N-terminal side in the amino acid sequence shown in SEQ ID NO: 1 is preferably lysine (Lys, K), arginine (Arg, R), glutamine (Gln, Q), or asparagine (Asn, N). More specifically, a consensus sequence comprising the amino acid sequence shown in SEQ ID NO: 1 is preferably (L/F)XG(V/I/M)FDGHGXXGXXX(S/A)(K/R/Q/N)XV. In such amino acid sequence, pluralities of amino acids in parentheses represent possible variations of amino acid residues at the relevant positions. Also, in the following amino acid sequences, "X" means that any amino acid residue may be present at the relevant position.

Also, such a consensus sequence may be a sequence containing the following 3 amino acid residues on the N-terminal side of Region I in FIGS. 1-1, 1-2 and 1-3: (D/E/N)XX.

Here, in the amino acid sequence shown in SEQ ID NO: 2, an amino acid residue denoted as "Xaa," may be any amino acid, and it is not limited to any particular amino acid. However, the $5^{th}$ amino acid residue from the N-terminal side in the amino acid sequence shown in SEQ ID NO: 2 is preferably glycine (Gly, G), alanine (Ala, A), or serine (Ser, S). The $6^{th}$ amino acid residue from the N-terminal side in the amino acid sequence shown in SEQ ID NO: 2 is preferably valine (Val, V), leucine (Leu, L), or isoleucine (Ile, I). The $9^{th}$ amino acid residue from the N-terminal side in the amino acid sequence shown in SEQ ID NO: 2 is preferably isoleucine (Ile, I), valine (Val, V), phenylalanine (Phe, F), methionine (Met, M), or leucine (Leu, L). The $12^{th}$ amino acid residue from the N-terminal side in the amino acid sequence shown in SEQ ID NO: 2 is preferably glycine (Gly, G) or alanine (Ala, A). The $15^{th}$ amino acid residue from the N-terminal side in the amino acid sequence shown in SEQ ID NO: 2 is preferably leucine (Leu, L), valine (Val, V), or isoleucine (Ile, I). The $17^{th}$ amino acid residue from the N-terminal side in the amino acid sequence shown in SEQ ID NO: 2 is preferably isoleucine (Ile, I), valine (Val, V), or methionine (Met, M). The $18^{th}$ amino acid residue from the N-terminal side in the amino acid sequence shown in SEQ ID NO: 2 is preferably glycine (Gly, G) or alanine (Ala, A). The $22^{nd}$ amino acid residue from the N-terminal side in the amino acid sequence shown in SEQ ID NO: 2 is preferably aspartic acid (Asp, D) or histidine (His, H). The $26^{th}$ amino acid residue from the N-terminal side in the amino acid sequence shown in SEQ ID NO: 2 is preferably valine (Val, V) or isoleucine (Ile, I). The $27^{th}$ amino acid residue from the N-terminal side in the amino acid sequence shown in SEQ ID NO: 2 is preferably leucine (Leu, L), methionine (Met, M), or isoleucine (Ile, I). More specifically, a consensus sequence comprising the amino acid sequence shown in SEQ ID NO: 2 is preferably SGXT(G/A/S)(V/L/I)XX(I/V/F/M/L)XX(G/A)XX(L/V/I)X(I/V/M)(A/G)NXG(D/H)SRA(V/I)(L/M/I). In such amino acid sequence, pluralities of amino acids in parentheses represent possible variations of amino acid residues at the relevant positions. Also, in the following amino acid sequences, "X" means that any amino acid residue may be present at the relevant position.

Here, the amino acid sequence shown in SEQ ID NO: 3, an amino acid residue denoted as "Xaa," may be any amino acid, and it is not limited to any particular amino acid. However, the $4^{th}$ amino acid residue from the N-terminal side in the amino acid sequence shown in SEQ ID NO: 3 is preferably methionine (Met, M), valine (Val, V), or phenylalanine (Phe, F). The $5^{th}$ amino acid residue from the N-terminal side in the amino acid sequence shown in SEQ ID NO: 3 is preferably serine (Ser, S), alanine (Ala, A), or threonine (Thr, T). The $7^{th}$ amino acid residue from the N-terminal side in the amino acid sequence shown in SEQ ID NO: 3 is preferably alanine (Ala, A) or serine (Ser, S). The $8^{th}$ amino acid residue from the N-terminal side in the amino acid sequence shown in SEQ ID NO: 3 is preferably phenylalanine (Phe, F), isoleucine (Ile, I), or valine (Val, V). The $14^{th}$ amino acid residue from the N-terminal side in the amino acid sequence shown in SEQ ID NO: 3 is preferably lysine (Lys, K) or glutamic acid (Glu, E). The $18^{th}$ amino acid residue from the N-terminal side in the amino acid sequence shown in SEQ ID NO: 3 is preferably valine (Val, V) or leucine (Leu, L). The $19^{th}$ amino acid residue from the N-terminal side in the amino acid sequence shown in SEQ ID NO: 3 is preferably isoleucine (Ile, I) or valine (Val, V). The $23^{rd}$ amino acid residue from the N-terminal side in the amino acid sequence shown in SEQ ID NO: 3 is preferably glutamic acid (Glu, E), glutamine (Gln, Q), or aspartic acid (Asp, D). The $24^{th}$ amino acid residue from the N-terminal side in the amino acid sequence shown in SEQ ID NO: 3 is preferably isoleucine (Ile, I), valine (Val, V), or phenylalanine (Phe, F). The $29^{th}$ amino acid residue from the N-terminal side in the amino acid sequence shown in SEQ ID NO: 3 is preferably isoleucine (Ile, I), leucine (Leu, L), or valine (Val, V). The $30^{th}$ amino acid residue from the N-terminal side in the amino acid sequence shown in SEQ ID NO: 3 is preferably serine (Ser, S), threonine (Thr, T), or asparagine (Asn, N). The $33^{rd}$ amino acid residue from the N-terminal side in the amino acid sequence shown in SEQ ID NO: 3 is preferably aspartic acid (Asp, D), asparagine (Asn, N), or histidine (His, H). The $35^{th}$ amino acid residue from the N-terminal side in the amino acid sequence shown in SEQ ID NO: 3 is preferably phenylalanine (Phe, F) or tyrosine (Tyr, Y). The $36^{th}$ amino acid residue from the N-terminal side in the amino acid sequence shown in SEQ ID NO: 3 is preferably leucine (Leu, L), isoleucine (Ile, I), valine (Val, V), phenylalanine (Phe, F), or methionine (Met, M). The $37^{th}$ amino acid residue from the N-terminal side in the amino acid sequence shown in SEQ ID NO: 3 is preferably valine (Val, V), leucine (Leu, L), or isoleucine (Ile, I). The $38^{th}$ amino acid residue from the N-terminal side in the amino acid sequence shown in SEQ ID NO: 3 is preferably leucine (Leu, L) or valine (Val, V). The $40^{th}$ amino acid residue from the N-terminal side in the amino acid sequence shown in SEQ ID NO: 3 is preferably threonine (Thr, T) or serine (Ser, S). The $43^{rd}$ amino acid residue from the N-terminal side in the amino acid sequence shown in SEQ ID NO: 3 is preferably valine (Val, V), isoleucine (Ile, I), or methionine (Met, M). The $44^{th}$ amino acid residue from the N-terminal side in the amino acid sequence shown in SEQ ID NO: 3 is preferably tryptophan (Trp, W) or phenylalanine (Phe, F). The $45^{th}$ amino acid residue from the N-terminal side in the amino acid sequence shown in SEQ ID NO: 3 is preferably aspartic acid (Asp, D) or glutamic acid (Glu, E). The $47^{th}$ amino acid residue from the N-terminal side in the amino acid sequence shown in SEQ ID NO: 3 is preferably leucine (Leu, L), isoleucine (Ile, I), or methionine (Met, M). The $48^{th}$ amino acid residue from the N-terminal side in the amino acid sequence shown in SEQ ID NO: 3 is preferably serine (Ser, S), threonine (Thr, T), or proline (Pro, P). The $49^{th}$ amino acid residue from the N-terminal side in the amino acid sequence shown in SEQ ID NO: 3 is preferably asparagine (Asn, N) or serine (Ser, S). The $52^{nd}$ amino acid residue from the N-terminal side in the amino acid sequence shown in SEQ ID NO: 3 is preferably valine (Val, V) or alanine (Ala, A). The $55^{th}$ amino acid residue from the N-terminal side in the amino acid sequence shown in SEQ ID NO: 3 is preferably leucine (Leu, L), valine (Val, V), isoleucine (Ile, I), or methionine (Met, M). The $56^{th}$ amino acid residue from the N-terminal side in the amino acid sequence shown in SEQ ID NO: 3 is preferably isoleucine (Ile, I) or valine (Val, V). Preferably, an example of the consensus sequence comprising the amino acid sequence shown in SEQ ID NO: 3 is more specifically GXA(M/V/F)(S/A/T)R(A/S)(F/I/V)GDXXX(K/E)XXG(V/L)(I/V)XXP(E/Q/D)(I/V/F)XXX X(I/L/V)(T/S)XX(D/N/H)X(F/Y)(L/I/V/F)(V/L/I)(L/V)A(T/S)DG(V/I/M)(W/F)(D/E)X(L/I/M)(S/T/P)(N/S)XX(V/A)XX(L/V/I/M)(I/V). In such amino acid sequence, pluralities of amino acids in parentheses represent possible variations of amino acid residues at the relevant positions. Also, in the following amino acid sequences, "X" means that any amino acid residue may be present at the relevant position.

Here, the $20^{th}$ amino acid residue from the N-terminal side in the amino acid sequence shown in SEQ ID NO: 3 is more preferably alanine (Ala, A), serine (Ser, S), or cysteine (Cys, C). Also, the $50^{th}$ amino acid residue from the N-terminal side in the amino acid sequence shown in SEQ ID NO: 3 is more preferably aspartic acid (Asp, D), glutamic acid (Glu, E), lysine (Lys, K), glutamine (Gln, Q), or asparagine (Asn, N).

Variations of amino acid residues that can be present at given positions are determined based on the following reasons. As described in Reference (1) ("McKee Biochemistry," 3rd ed., Chapter 5 Amino Acid•Peptide•Protein 5.1 Amino Acid; editorial supervisor: Atsushi Ichikawa; translation supervisor: Shinichi Fukuoka; publisher: Ryosuke Sone; publishing office: Kagaku-Dojin Publishing Company, INC, ISBN4-7598-0944-9), it is well known that amino acids are classified based on side chains having similar properties (e.g., chemical properties and physical sizes). Also, it is well known that molecular evolutionary substitution frequently takes place among amino acid residues classified in a given group, while retaining protein activity. Based on these concepts, a substitution (mutation) score matrix for amino acid residues (BLOSUM: Blocks of Amino Acid Substitution Matrix) is proposed in FIGS. 2-1, 2-2 and 2-3 of Reference (2): Henikoff S., Henikoff J. G, Amino-acid substitution matrices from protein blocks, Proc. Natl. Acad. Sci. U.S.A., 89, 10915-10919 (1992) and is broadly used. Reference (2) is based on a finding that amino acid substitutions that take place among amino acids with side chains having similar chemical properties result in less structural or functional changes in the entire protein. According to References (1) and (2) above, amino acid side chain groups to be used in multiple alignment can be considered based on indices such as chemical properties and physical sizes. They are shown as amino acid groups with a score of 0 or higher and preferably as amino acid groups with a score of 1 or higher through the use of the score matrix (BLOSUM) disclosed in Reference (2). Typical groups are the following 8 groups. Further precisely grouped amino acid groups may be amino acid groups with a score of 0 or higher, preferably a score of 1 or higher, and further preferably a score of 2 or higher.

1) Aliphatic Hydrophobic Amino Acid Group (ILMV Group)

This group is a group of amino acids having aliphatic hydrophobic side chains, among neutral nonpolar amino acids disclosed in Reference (1) above, which is composed of V (Val, valine), L (Leu, leucine), I (Ile, isoleucine), and M (Met, methionine). Among amino acids classified as neutral nonpolar amino acids according to Reference (1), FGACWP is not included in this "aliphatic hydrophobic amino acid group" because of the following reasons: G (Gly, glycine) and A (Ala, alanine) are the same size as that of or smaller in size than a methyl group and have weak non polar effects; C (Cys, cysteine) may play an important role in S—S bonds and has a property of forming a hydrogen bond with an oxygen atom or a nitrogen atom; F (Phe, phenylalanine) and W (Trp, tryptophan) have side chains with significantly large molecular weights and have strong aromatic effects; P (Pro, proline) has strong imino acid effects, so as to fix the angle of the main chain of the polypeptide.

2) Group Having Hydroxymethylene Group (ST Group)

This group is a group of amino acids (from among neutral polar amino acids) having hydroxymethylene groups in side chains, which is composed of S (Ser, serine) and T (Thr, threonine). Hydroxy groups existing in the side chains of S and T constitute sugar-binding sites, so that these sites are often important for a polypeptide (protein) to have specific activity.

3) Acidic Amino Acid (DE Group)

This group is a group of amino acids having acidic carboxyl groups in side chains, which is composed of D (Asp, aspartic acid) and E (Glu, glutamic acid).

4) Basic Amino Acid (KR Group)

This group is a group of basic amino acids, which is composed of K (Lys, lysine) and R (Arg, arginine). These K and R are positively charged within a wide pH range and have basic properties. On the other hand, H (His, histidine) classified in basic amino acids is almost never ionized at pH 7, so that H is not classified in this group.

5) Methylene Group=Polar Group (DHN Group)

This group is characterized in that: in all cases, a methylene group as a side chain binds to an α-carbon element beyond which a polar group is present; and the physical sizes of methylene groups (nonpolar groups) closely resemble from each other. This group is composed of N (Asn, asparagine; polar group is an amide group), D (Asp, aspartic acid; polar groups are carboxyl groups), and H (His, histidine; polar groups are imidazole groups).

6) Dimethylene Group=Polar Group (EKQR Group)

This group is characterized in that: in all cases, linear hydrocarbon having a length longer than that of a dimethylene group binds as a side chain to an α-carbon element, beyond which a polar group is present; and the physical sizes of dimethylene groups that are nonpolar groups closely resemble from each other. This group is composed of E (Glu, glutamic acid, polar group is a carboxyl group), K (Lys, lysine; polar groups are amino groups), Q (Gln, glutamine; polar groups are amide groups), and R (Arg, arginine; polar groups are imino groups and amino groups).

7) Aromatic Series (FYW Group)

This group is a group of aromatic amino acids having benzene nuclei in the side chains and characterized by having chemical properties unique in aromatic series. This group is composed of F (Phe, phenylalanine), Y (Tyr, tyrosine), and W (Trp, tryptophan).

8) Ring & Polar (HY Group)

This group is a group of amino acids having both ring structures in the side chains and polarity, which is composed of H (H, histidine; Both ring structures and polar groups are imidazole groups), and Y (Tyr, tyrosine; Ring structures are benzene nuclei and polar groups are hydroxy groups).

As described above, it is understood that: in the given amino acid sequences shown in SEQ ID NOS: 1-3, an amino acid residue denoted as Xaa may be any amino acid; or amino acid residues denoted as Xaa may be substituted with each other within the above groups 1)-8). Hence, in the present invention, the protein phosphatase 2C gene to be over-expressed in a plant may be a protein phosphatase 2C gene from any plant, as long as it has the 3 consensus sequences comprising the amino acid sequences shown in SEQ ID NOS: 1-3 in such order from the N-terminal side.

More specifically, examples of an *Arabidopsis thaliana* protein phosphatase 2C-coding gene having the 3 consensus sequences (comprising the amino acid sequences shown in SEQ ID NOS: 1-3) in such order from the N-terminal side include At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), At5g27930-AtPP2C6-7 (SEQ ID NO:36), At2g20050 (SEQ ID NO:66), and At3g06270 (SEQ ID NO:67). In the present invention, at least one type of gene selected from the gene group is over-expressed. Particularly in the present invention, it is preferable to cause overexpression of at least one type of gene selected from among At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), and At5g27930-AtPP2C6-7 (SEQ ID NO:36). Particularly, in the present invention, it is more preferable to cause overexpression of at least one type of gene selected from among At3g16800 (SEQ ID NO:48), At3g05640 (SEQ ID NO:5), and At5g27930-AtPP2C6-7 (SEQ ID NO:36) and it is most preferable to cause overexpression of a gene specified by At3g05640 (SEQ ID NO:5).

In addition, FIGS. 2-1, 2-2 and 2-3 show the results of alignment analysis using a CLUSTAL W (1.83) multiple sequence alignment program (that can be used with the DDBJ of the National Institute of Genetics (on world wide web at clustalw.ddbj.nig.ac.jp/top-j)) for amino acid sequences encoded by At1g03590 (SEQ ID NO:63)-AtPP2C6-6, At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), and At5g27930 (SEQ ID NO:36)-AtPP2C6-7 (amino acid (sequence) substitution matrix used herein is default matrix, BLOSUM (Blocks of Amino Acid Substitution Matrix)).

That is, FIGS. 2-1, 2-2 and 2-3 show the 3 consensus sequences in protein phosphatase 2C encoded by At1g03590-AtPP2C6-6 (SEQ ID NO:63), At1g16220 (SEQ ID NO:61), At1g79630 (SEQ ID NO:62), At5g01700 (SEQ ID NO:65), At3g02750 (SEQ ID NO:42), At5g36250 (SEQ ID NO:64), At5g26010 (SEQ ID NO:59), At4g32950 (SEQ ID NO:60), At3g16800 (SEQ ID NO:48), At3g05640 (SEQ ID NO:5), and At5g27930-AtPP2C6-7 (SEQ ID NO:36). Regions denoted as I-III in FIGS. 2-1, 2-2 and 2-3 are subjected with an ortholog of a rice-derived protein phosphatase 2C gene (described later) to alignment analysis, so that the 3 consensus sequences comprising the amino acid sequences shown in SEQ ID NOS: 1-3 above can be defined as the 3 consensus sequences comprising the amino acid sequences shown in SEQ ID NOS: 53-55, respectively.

The consensus sequence shown in SEQ ID NO: 53 is more specifically (L/F)CG(V/I/M)FDGHGXXGXX(V/I)(S/A)(K/R)XV. The consensus sequence shown in SEQ ID NO: 54 is more specifically SGXT(G/A/S)(V/L)XX(I/V/F/L)XX(G/A)XX(L/V/I)X(I/V/M)(A/G)NXG(D/H)SRA(V/I)(L/M/I). The consensus sequence shown in SEQ ID NO: 55 is more specifically GLA(M/V)(S/A)R(A/S)(F/L)GDXX(L/I/V)KX(Y/F/H)G(V/L)(I/V)XXP(E/Q/D)(I/V/F)XX XX(I/L/V)(T/S)XXDX(F/Y)(L/I/V/M)(V/L/I)LA(T/S)DG(V/I/M) WDX(L/I/M/V)(S/T)NX(E/D)(V/A)XX(L/V/I)(I/V).

In addition, in such amino acid sequences, pluralities of amino acids in parentheses represent possible variations of amino acid residues at the relevant positions. Also, in these amino acid sequences, "X" means that any amino acid residue may be present at the relevant position.

Here, the $9^{th}$ amino acid residue from the N-terminal side in the amino acid sequence shown in SEQ ID NO: 54 is more preferably isoleucine (Ile, I), valine (Val, V), or phenylalanine (Phe, F). Also, the $11^{th}$ amino acid residue from the N-terminal side in the amino acid sequence shown in SEQ ID NO: 54 is more preferably glutamine (Gln, Q) or histidine (His, H). Moreover, the $13^{th}$ amino acid residue from the N-terminal side in the amino acid sequence shown in SEQ ID NO: 54 is more preferably lysine (Lys, K), glutamic acid (Glu, E), serine (Ser, S), glutamine (Gln, Q), aspartic acid (Asp, D), or asparagine (Asn, N).

Here, the $7^{th}$ amino acid residue from the N-terminal side in the amino acid sequence shown in SEQ ID NO: 55 is more preferably alanine (Ala, A). Also, the $8^{th}$ amino acid residue from the N-terminal side in the amino acid sequence shown in SEQ ID NO: 55 is more preferably phenylalanine (Phe, F). Moreover, the $11^{th}$ amino acid residue from the N-terminal side in the amino acid sequence shown in SEQ ID NO: 55 is more preferably phenylalanine (Phe, F) or tyrosine (Tyr, Y). Furthermore, the $13^{th}$ amino acid residue from the N-terminal side in the amino acid sequence shown in SEQ ID NO: 55 is more preferably leucine (Leu, L) or isoleucine (Ile, I). Moreover, the $15^{th}$ amino acid residue from the N-terminal side in the amino acid sequence shown in SEQ ID NO: 55 is more preferably aspartic acid (Asp, D), serine (Ser, S), or glutamic acid (Glu, E). Furthermore, the $20^{th}$ amino acid residue from the N-terminal side in the amino acid sequence shown in SEQ ID NO: 55 is more preferably serine (Ser, S), alanine (Ala, A), or cysteine (Cys, C). Moreover, the $27^{th}$ amino acid residue from the N-terminal side in the amino acid sequence shown in SEQ ID NO: 55 is more preferably histidine (His, H) or arginine (Arg, R). Furthermore, the $34^{th}$ amino acid residue from the N-terminal side in the amino acid sequence shown in SEQ ID NO: 55 is more preferably glutamine (Gln, Q), glutamic acid (Glu, E), or histidine (His, H). Furthermore, the $36^{th}$ amino acid residue from the N-terminal side in the amino acid sequence shown in SEQ ID NO: 55 is more preferably leucine (Leu, L), isoleucine (Ile, I), or valine (Val, V). Furthermore, the $47^{th}$ amino acid residue from the N-terminal side in the amino acid sequence shown in SEQ ID NO: 55 is more preferably leucine (Leu, L), isoleucine (Ile, I), or valine (Val, V). Furthermore, the $50^{th}$ amino acid residue from the N-terminal side in the amino acid sequence shown in SEQ ID NO: 55 is more preferably lysine (Lys, K), glutamic acid (Glu, E), glutamine (Gln, Q), aspartic acid (Asp, D), or asparagine (Asn, N).

As examples, the nucleotide sequence of the coding region in the gene specified by At3g05640 (SEQ ID NO:5) is shown in SEQ ID NO: 4 and the amino acid sequence of protein phosphatase 2C encoded by the gene specified by At3g05640 is shown in SEQ ID NO: 5. Also, the nucleotide sequence of the coding region in the gene specified by At5g27930 (SEQ ID NO:36) is shown in SEQ ID NO: 35 and the amino acid sequence of protein phosphatase 2C encoded by the gene specified by At5g27930 is shown in SEQ ID NO: 36. Moreover, the nucleotide sequence of the coding region in the gene specified by At3g02750 (SEQ ID NO:42) is shown in SEQ ID NO: 41 and the amino acid sequence of protein phosphatase 2C encoded by the gene specified by At3g02750 is shown in SEQ ID NO: 42. Furthermore, the nucleotide sequence of the coding region in the gene specified by At3g16800 (SEQ ID NO:48) is shown in SEQ ID NO: 47 and the amino acid sequence of protein phosphatase 2C encoded by the gene specified by At3g16800 is shown in SEQ ID NO: 48.

Also, in the present invention, genes functionally equivalent to genes listed above may also be over-expressed. Here, the term "functionally equivalent gene" refers to, for example, a gene (from an organism other than *Arabidopsis thaliana*) that: has the 3 consensus sequences (preferably, the 3 consensus sequences comprising the amino acid sequences shown in SEQ ID NOS: 53-55. The same applies to the following) comprising the amino acid sequences shown in SEQ ID NOS: 1-3 in such order from the N-terminal side; and encodes protein phosphatase 2C. Also, the term "functionally equivalent gene" refers to a gene that encodes a protein having protein phosphatase 2C activity.

The term "protein phosphatase 2C activity" refers to $Mg^{2+}$- or $Mn^{2-}$-dependent serine/threonine phosphatase (Ser/Thr phosphatase) activity. Therefore, whether or not a gene encodes a protein having protein phosphatase 2C activity can be confirmed by examining whether or not the gene product has serine/threonine phosphatase activity in the presence of $Mg^{2-}$ or $Mn^{2+}$. Conventionally known techniques can be appropriately employed for determining serine/threonine phosphatase activity. For example, a commercially available activity determination kit ProFluor (registered trademark) Ser/Thr Phosphatase Assay (Promega) can be used.

Here, example of organisms is not limited to *Arabidopsis thaliana*. For example, rice (*Oryza sativa*) is included. Specifically, an example of a functionally equivalent gene is a rice Os05g0358500 gene. The nucleotide sequence of a coding region of the Os05g0358500 gene is shown in SEQ ID NO: 6 and the amino acid sequence of the protein encoded by the gene is shown in SEQ ID NO: 7. Also, examples of the above-mentioned rice-derived functionally equivalent gene include Os11g0109000 (the nucleotide sequence and the amino acid sequence are shown in SEQ ID NOS: 8 and 9, respectively), Os12g0108600 (the nucleotide sequence and the amino acid sequence are shown in SEQ ID NOS: 10 and 11, respectively), Os02g0471500 (the nucleotide sequence and the amino acid sequence are shown in SEQ ID NOS: 12 and 13, respectively), Os04g0321800 (the nucleotide sequence and the amino acid sequence are shown in SEQ ID NOS: 14 and 15, respectively), Os11g0417400 (the nucleotide sequence and the amino acid sequence are shown in SEQ ID NOS: 16 and 17, respectively), Os07g0566200 (the nucleotide sequence and the amino acid sequence are shown in SEQ ID NOS: 18 and 19, respectively), Os08g0500300 (the nucleotide sequence and the amino acid sequence are shown in SEQ ID NOS: 20 and 21, respectively), Os02g0224100 (the nucleotide sequence and the amino acid sequence are shown in SEQ ID NOS: 22 and 23, respectively), and Os02g0281000 (the nucleotide sequence and the amino acid sequence are shown in SEQ ID NOS: 56 and 57, respectively).

Moreover, examples of the above-mentioned functionally equivalent genes from plants other than *Arabidopsis thaliana* and rice include genes (UniProt data base Accession Nos. A9P973, A9PFS0, and A9P7U4) from black cottonwood (*Populus trichocarpa*), genes (UniProt data base Accession Nos. A7PRZ8, A7Q8H4, A7PV59, A5C3B0, A5BF43, A7QFG6, A7P4H7, A5C0C9, A5AP53, A7QQF9, and A5BDP5) from european grape (*Vitis vinifera*), genes (UniProt data base Accession Nos. Q2HW33 and Q4L0F8) from *Medicago truncatula* (*Medicago truncatula*), a gene (GenBank data base Accession No. AY651248) from alfalfa (*Medicago sativa*), genes (UniProt data base Accession Nos. A9SE70, A9SE69, and A9RFU1) from *Physcomitrella patens* (*Physcomitrella patens*), a gene (UniProt data base Accession No. 2511453C) from ice plant (*Mesembryanthemum crystallinum*), a gene (UniProt data base Accession No. A8HQG8) from *Chlamydomonas reinhardtii* (*Chlamydomonas reinhardtii*), genes (GenBank data base Accession Nos. BT024031, BT017414, and BT024134) from corn (*Zea mays*), genes (GenBank data base Accession Nos. AC189312 and AC189579) from rapeseed (*Brassica rapa*), genes (GenBank data base Accession Nos. AP009550, AP009302, and AP009278) from tomato (*Solanum lycopersicum*), a gene (GenBank data base Accession No. AC182571) from monkey flower (*Mimulus guttatus*), and a gene (GenBank data base Accession No. AP006489) from monocellular red alga (*Cyanidioschyzon merolae*).

In these plants other than *Arabidopsis thaliana*, which are represented by the above examples, a gene encoding protein phosphatase 2C that has the 3 consensus sequences comprising the amino acid sequences shown in SEQ ID NOS: 1-3 in such order from the N-terminal side can be easily searched for and/or identified from a known database such as GenBank based on the above-listed nucleotide sequence of *Arabidopsis thaliana*-derived protein phosphatase 2C gene or amino acid sequence of protein phosphatase 2C.

In addition, a protein phosphatase 2C gene to be over-expressed in the present invention is not limited to the above described protein phosphatase 2C genes comprising the nucleotide sequences and the amino acid sequences shown in SEQ ID NOS: 4-23, 35, 36, 41, 42, 47, and 48. Hence, the protein phosphatase 2C gene may be a gene that contains an amino acid sequence having a deletion, a substitution, an addition, or an insertion of one or a plurality of amino acid sequences with respect to the amino acid sequences shown in odd numbers of SEQ ID NOS: 4-23 or the amino acid sequence shown in SEQ ID NO: 36, 42, or 48, and, has protein phosphatase 2C activity. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by altering a nucleotide sequence encoding the above protein phosphatase 2C gene by a technique known in the art. Mutation can be introduced into a nucleotide sequence by a known technique such as the Kunkel method or the Gapped duplex method or a method based thereof. For example, mutation is introduced with a mutagenesis kit using site-directed mutagenesis (e.g., Mutant-K or Mutant-G (both are trade names of Takara Bio)) or the like, or a LA PCR in vitro Mutagenesis series kit (trade name, Takara Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Also, protein phosphatase 2C genes to be over-expressed herein may be genes homologous to the protein phosphatase 2C genes comprising the nucleotide sequences and the amino acid sequences shown in SEQ ID NOS: 4-23. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes analogous to the protein phosphatase 2C genes comprising the nucleotide sequences and the amino acid sequences shown in SEQ ID NOS: 4-23, 35, 36, 41, 42, 47, and 48 include genes encoding proteins having: amino acid sequences that have 70% or more, preferably 80% or more, more preferably 90% or more, and most preferably 95% or more similarity to these amino acid sequences; the 3 consensus sequences comprising the amino acid sequences shown in SEQ ID NOS: 1-3 in such order from the N-terminal side; and protein phosphatase 2C activity. Here, the value of similarity refers to a value that can be found based on default setting using a computer mounted with a BLAST (Basic Local Alignment Search Tool) program and a database containing gene sequence information.

Also, genes analogous to protein phosphatase 2C genes comprising the nucleotide sequences and the amino acid sequences shown in SEQ ID NOS: 4-23, 35, 36, 41, 42, 47, and 48 can be identified by, when the plant genome information remains unclarified, extracting the genome from a target plant or constructing a cDNA library for a target plant and then isolating a genomic region or cDNA hybridizing under stringent conditions to at least a portion of the protein phosphatase 2C genes comprising the nucleotide sequences shown in even numbers of SEQ ID NOS: 4-23 or the nucleotide sequence shown in 35, 41, or 47. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1×SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

The plant according to the present invention exerts significantly improved production of biomass and/or seeds compared with wild-type plants, as a result of overexpression of a protein phosphatase 2C gene having the above described 3 consensus sequences that comprise the amino acid sequences shown in SEQ ID NOS: 1-3 from the N-terminal side in such order. Examples of a technique for causing the overexpression of such protein phosphatase 2C gene include a technique for modifying a promoter of an endogenous protein phosphatase 2C gene in a target plant, a technique for introducing an expression vector in which an exogenous protein phosphatase 2C gene is arranged under control of a promoter that enables overexpression, and a technique by which the two above techniques are performed simultaneously.

A preferred example is a technique for introducing an expression vector in which the above protein phosphatase 2C gene is arranged under control of a promoter that enables overexpression into a target plant.

Expression Vector

An expression vector is constructed to contain a promoter that enables overexpression and the above described protein phosphatase 2C gene. As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables overexpression of a protein phosphatase 2C gene within a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase•oxidase small subunit gene promoter, a napin gene promoter, and an oleosin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific overexpression in a plant can also be used herein. As such promoter, any conventionally known promoter can be used. When the above described protein phosphatase 2C gene is site-specifically over-expressed using such promoter, a plant organ in which the gene is over-expressed can be more increased than wild-type plant organs.

In addition, an expression vector may further contain other DNA segments in addition to a promoter and the above protein phosphatase 2C gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium.*

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a plasmid after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector may contain various DNA segments depending on purposes.

A method for constructing a recombinant expression vector is not particularly limited. To an appropriately selected vector serving as a mother body, the above promoter and the above protein phosphatase 2C gene, and if necessary, the above other DNA segments may be introduced in an predetermined order. For example, the above protein phosphatase 2C gene and a promoter (and, if necessary, a transcription terminator or the like) are linked to construct an expression cassette and then the cassette may be introduced into a vector. In construction of an expression cassette, for example, cleavage sites of DNA segments are prepared to have protruding ends complementary to each other and then performing a reaction with a ligation enzyme, making it possible to specify the order of the DNA segments.

In addition, when an expression cassette contains a terminator, DNA segments may be arranged in the following order from upstream: a promoter, the above protein phosphatase 2C gene, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in Bechtold, E., Ellis, J. and Pelletier, G (1993) In Planta *Agrobacterium*-mediated gene transfer by infiltration of adult *Arabidopsis* plants. C. R. Acad. Sci. Paris Sci. Vie, 316, 1194-1199., or a method described in Zyprian E, Kado Cl, *Agrobacterium*-mediated plant transformation by novel mini-T vectors in conjunction with a high-copy vir region helper plasmid. Plant Molecular Biology, 1990, 15(2), 245-256. can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which the above expression vector or an expression cassette containing no expression vector, but a target gene is introduced include cells of each tissue of plant organs such as flowers, leaves, and roots, calluses, and suspension-cultured cells. At this time, an appropriate expression vector may be constructed according to the types of plant to be produced or a versatile expression vector may be constructed in advance and then introduced into plant cells.

Plants into which an expression vector is introduced or in other words, plants required to increase the production of biomass are not particularly limited. Specifically, through overexpression of the above-described protein phosphatase 2C gene, effects of increasing the production of biomass can be expected for all plants. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana* (*Arabidopsis thaliana*), rapeseed (*Brassica rapa, Brassica napus, Brassica campestris*), cabbage (*Brassica oleracea* var. *capitata*), *napa* (*Brassica rapa* var *pekinensis*), ging-geng-cai (*Brassica rapa* var *chinensis*), turnip (*Brassica rapa* var. *rapa*), turnip greens (*Brassica rapa* var. *hakabura*), potherb mustard (*Brassica rapa* var *lancinifolia*), komatsuna (*Brassica rapa* var *peruviridis*), pak Choi (*Brassica rapa* var. *chinensis*), daikon (*Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), *Wisteria* (*Wisteria floribunda*), peanuts (*Arachis hypogaea*), bird's foot trefoil (*Lotus corniculatus* var *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var *gourda*), and the like.

Family Rosaceae: almond (*Amygdalus communis*), rose (*Rosa*), strawberry (*Fragaria*), cherry (*Prunus*), apple (*Malus pumila* var *domestica*), and the like.

Family Caryophyllaceae: carnation (*Dianthus caryophyllus*) and the like.

Family Salicaceae: poplar (*Populus trichocarpa, Populus nigra*, or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), *miscanthus* (Japanese silver grass) (*Miscanthus virgatum*), *sorghum* (*Sorghum*) and switch grass (*Panicum*), and the like.

Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. This is because the costs for biofuel such as bioethanol, biodiesel, biomethanol, bioDME, bioGTL (BTL), and biobutanol can be reduced by increasing the production of biomass using energy crops.

Also, as described above, protein phosphatase 2C genes that can be used in the present invention can be isolated from various plants and used. Such protein phosphatase 2C genes can be appropriately selected and used, depending on the types of target plant required to increase the biomass production. Specifically, when a plant required to increase the biomass production is a monocotyledon, a protein phosphatase 2C gene that is isolated from a monocotyledon is preferably over-expressed. In particular, when a plant required to increase the biomass production is rice, the rice-derived protein phosphatase 2C gene (SEQ ID NO: 6) is preferably over-expressed.

In addition, in the present invention, even when a plant required to increase the biomass production is a monocotyledon, a dicotyledon-derived protein phosphatase 2C gene may be over-expressed. Specifically, for example, the *Arabidopsis thaliana*-derived protein phosphatase 2C gene (SEQ ID NO: 4) may be introduced into not only dicotyledons, but also a variety of plants that are classified as monocotyledons, so that the gene is over-expressed.

Other Steps and Methods

After the above transformation, a step of selecting proper transformants from plants can be performed by a conventionally known method. Such selection method is not particularly limited. For example, selection can be made based on drug resistance such as hygromycin resistance. Alternatively, after the growth of transformants, plants are directly weighed or the any organs or tissues thereof are weighed, the weights are compared with those of wild-type plants, and then plants with significantly increased weights thereof may be selected.

Also, progeny plants can be obtained from transformed plants obtained by transformation according to a conventional method. Progeny plants retaining a trait such that the protein phosphatase 2C gene is over-expressed are selected based on the amount of biomass. Therefore, a stable plant line capable of producing an increased amount of biomass because of having the above trait can be produced. Also, plant cells or reproductive materials, such as seeds, fruits, stocks, calluses, tubers, cut ears, or lumps, may be obtained from a transformed plant or an offspring plant thereof. A stable plant line capable of producing an increased amount of biomass because of having the above trait can be mass-produced therefrom based on such materials.

In addition, examples of the term "plant(s)" in the present invention include at least any of grown plants, plant cells, plant tissues, calluses, and seeds. Specifically, in the present invention, any forms of plants that can be finally grown to mature plants are regarded as "plants." Also, examples of such plant cells include various forms of plant cells, such as suspended culture cells, protoplasts, and leaf sections. Plants can be obtained through the growth and differentiation of these plant cells. In addition, regeneration of plants from plant cells can be performed using a conventionally known method depending on the type of plant cells.

As explained above, according to the present invention, plants capable of exerting the significantly increased production of biomass and/or seeds per plant compared with wild-type plants can be provided through overexpression of the above described protein phosphatase 2C gene. Here, the term "significantly increased production of biomass" refers to a situation in which the total weight of each plant is statistically significantly increased compared with the same of a wild-type plant. In this case, even when some plant tissues become specifically large and the sizes of the other tissues are equivalent to those of a wild-type plant, it is concluded that the production of biomass is increased if the total weight of the entire plant is large. Also, the term "significantly increased production of seeds" refers to a situation in which the total amount and/or total number of seeds harvested from a plant is statistically significantly high compared with wild-type plants. That is, the term "significantly increased production of seeds" may refer to any of: a case in which the size of each seed is improved; a case where the size per seed is equivalent but the number of seeds is improved; or a case in which the size per seed is improved and the number of seeds is also improved.

According to the present invention, the production of biomass and/or seeds by plants is increased. Hence, improvement in productivity can be achieved in both of the following cases: a case in which a purpose is to produce the whole plant; and a case in which a purpose is to produce some plant tissues (e.g., seeds) or components contained in plants. For example, when a purpose is to produce fats and oils contained in plant seeds, the amounts of fats and oils that can be harvested per area under cultivation can be greatly improved. Here, examples of fats and oils include, but are not particularly limited to, plant-derived fats and oils such as soybean oil, sesame oil, olive oil, coconut oil, rice oil, cottonseed oil, sunflower oil, corn oil, safflower oil, and rapeseed oil. Also, the thus produced fats and oils can be broadly used for household uses or industrial uses and can be further used as raw materials for biodiesel fuel. Hence, according to the present invention, the above fats and oils for household uses or industrial uses, biodiesel fuel, and the like can be produced at low cost with the use of plants over-expressing the above protein phosphatase 2C gene.

EXAMPLES

The present invention will be specifically described in the following reference examples and examples. However, the examples are not intended to limit the technical scope of the present invention.

Example 1

Preparation of Transformants (*Arabidopsis thaliana*) Through Introduction of the PP2C (Protein Phosphatase 2C) Gene (At3g05640 (SEQ ID NO:5))

1. Materials and Methods 1-1. Experimental Materials

As experimental materials, seeds of *Arabidopsis thaliana* mutants (Activation-tag T-DNA lines: Weigel T-DNS lines, Total of 20072 lines) were used. In addition, the seeds were purchased from the Nottingham *Arabidopsis* Stock Centre (NASC). Regarding the seeds used as experimental materials, Weigel, D. et al., 2000, Plant Physiol. 122, 1003-1013 can be referred to.

1-2. Methods 1-2-1. Selection of Salt-Resistant Mutants

Seeds of Weigel T-DNA lines were aseptically sowed on 125 mM or 150 mM NaCl-containing modified MS agar (1%) medium [vitamins in B5 medium, 10 g/1 sucrose, and 8 g/L agar (for bacterial medium; Wako Pure Chemical Industries, Ltd.)] and then cultured at 22° C. under 30-100 $\mu mol/m^2/sec$ illumination (a cycle of 16 hours in the light/8 hours in the dark). Two to 4 weeks after sowing, salt-resistant mutant candidates were selected. In addition, regarding MS medium, see Murashige, T. et al., 1962, Physiol. Plant. 15, 473-497. Also, regarding the B5 medium, see Gamborg, O. L. et al., 1968, Experimental Cell Research 50, 151-158.

1-2-2. DNA Preparation

A site for insertion of T-DNA into the genome of the thus selected salt-resistant *Arabidopsis thaliana* line was determined by a TAIL-PCR method. First, young leaves were harvested from the cultivated *Arabidopsis thaliana* plants and then crushed under liquid nitrogen freezing. DNA was prepared using a DNA preparation kit (DNeasy Plant Mini Kit, QIAGEN®) according to the standard protocols included with the kit.

1-2-3. TAIL-PCR Method and Presumption of T-DNA Insertion Site

Three (3) types of specific primer, TL1, TL2, and TL3, were determined to be located near the left T-DNA sequence (T-DNA left border) of an activation-tagging vector (pSKI015: GenBank accession No. AF187951) used in Weigel T-DNA lines. With the use of an arbitrary primer P1 and the following PCR reaction solutions and reaction conditions, TAIL-PCR (supervisors, Isao Shimamoto and Takuji Sasaki, New Edition, Plant PCR Experimental Protocols, 2000, pp. 83-89, Shujunsha, Tokyo, Japan; Liu, Y. G. and Whttier, R. F., 1995, Genomics 25, 674-681; Liu, Y. G. et al., Plant J., 8, 457-463, 1995) was performed, so that genomic DNA adjacent to T-DNA was amplified.

The specific sequences of the primers TL1, TL2, TL3, and P1 are as follows.

```
                                            (SEQ ID NO: 24)
TL1:       5'-TGC TTT CGC CAT TAA ATA GCG ACG G-3'

                                            (SEQ ID NO: 25)
TL2:       5'-CGC TGC GGA CAT CTA CAT TTT TG-3'

                                            (SEQ ID NO: 26)
TL3:       5'-TCC CGG ACA TGA AGC CAT TTA C-3'

                                            (SEQ ID NO: 27)
P1:        5'-NGT CGA SWG ANA WGA A-3'
```

In addition, in SEQ ID NO: 25, “n” represents “a,” “g,” “c,” or “t” (location: 1 and 11), “s” represents “g” or “c” (location: 7), and “w” represents “a” or “t” (location: 8 and 13).

The 1$^{st}$ PCR reaction solution composition and reaction conditions are shown in Table 1 and Table 2, respectively.

TABLE 1

| | | |
|---|---|---|
| Template (genomic DNA) | 10 | ng |
| 10 × PCR buffer (Takara Bio) | 2 | µl |
| 2.5 mM dNTPs (Takara Bio) | 1.6 | µl |
| 1$^{st}$ specific primer (TL1: SEQ ID NO: 24) | 0.5 | pmol |
| Arbitrary primer 1 (SEQ ID NO: 27) | 100 | pmol |
| TaKaRa Ex Taq (Takara Bio) | 1.0 | unit |
| Total | 20 | µl |

TABLE 2

| | |
|---|---|
| #1: | 94° C. (30 seconds)/95° C. (30 seconds) |
| #2: | 5 cycles of 94° C. (30 seconds)/65° C. (30 seconds)/72° C. (1 minute) |
| #3: | 1 cycle of 94° C. (30 seconds)/25° C. (1 minute)→raised to 72° C. within 3 minutes/72° C. (3 minutes) |
| #4: | 94° C. (15 seconds)/65° C. (30 seconds)/72° C. (1 minute), 94° C. (15 seconds)/68° C. (30 seconds)/72° C. (1 minute), and 15 cycles of 94° C. (15 seconds)/44° C. (30 seconds)/72° C. (1 minute) |
| #5: | 72° C. (3 minutes) |

The 2$^{nd}$ PCR reaction solution composition and reaction conditions are shown in Table 3 and Table 4, respectively.

TABLE 3

| | | |
|---|---|---|
| Template (50-fold dilution of the 1$^{st}$ PCR product) | 1 | µl |
| 10 × PCR buffer (Takara Bio) | 2 | µl |
| 2.5 mM dNTPs (Takara Bio) | 1.5 | µl |
| 2$^{nd}$ specific primer (TL2: SEQ ID NO: 25) | 5 | pmol |
| Arbitrary primer 1 (SEQ ID NO: 27) | 100 | pmol |
| TaKaRa Ex Taq (Takara Bio) | 0.8 | unit |
| Total | 20 | µl |

TABLE 4

| | |
|---|---|
| #6: | 94° C. (15 seconds)/64° C. (30 seconds)/72° C. (1 minute), 94° C. (15 seconds)/64° C. (30 seconds)/72° C. (1 minute), and 12 cycles of 94° C. (15 seconds)/44° C. (30 seconds)/72° C. (1 minute) |
| #5: | 72° C. (5 minutes) |

The 3$^{rd}$ PCR reaction solution composition and reaction conditions are shown in Table 5 and Table 6, respectively.

TABLE 5

| | | |
|---|---|---|
| Template (50-fold dilution of the 2$^{nd}$ PCR product) | 1 | µl |
| 10 × PCR buffer (Takara Bio) | 5 | µl |
| 2.5 mM dNTPs (Takara Bio) | 0.5 | µl |
| 3$^{rd}$ specific primer (TL3: SEQ ID NO: 26) | 10 | pmol |
| Arbitrary primer 1 (SEQ ID NO: 27) | 100 | pmol |
| TaKaRa Ex Taq (Takara Bio) | 1.5 | unit |
| Total | 50 | µl |

TABLE 6

| | |
|---|---|
| #7: | 20 cycles of 94° C. (30 seconds)/44° C. (30 seconds)/72° C. (1 minute) |
| #5: | 72° C. (3 minutes) |

Subsequently, the 2$^{nd}$ and the 3$^{rd}$ reaction products were subjected to agarose gel electrophoresis and then the presence or the absence of amplification and the specificity of reaction products were confirmed. Also, the 3$^{rd}$ amplification products were subjected to a sequencing reaction directly using a BigDye Terminator Cycle Sequencing Kit Ver. 3.1 (Applied Biosystems) and the specific primer TL3. Thus, a nucleotide sequence was determined using an ABI PRISM 3100 Genetic Analyzer (Applied Biosystems). As a result, 498-bp sequence information was obtained (SEQ ID NO: 28).

The *Arabidopsis* Information Resource (TAIR on world wide web at arabidopsis.org) was subjected to a BLAST search for the thus obtained sequence. Thus, the insertion site was found to be the gene of [AGI (*Arabidopsis* Genome Initiative gene code) code: At3g05630] of *Arabidopsis thaliana* chromosome 3.

1-2-4. Prediction of Activated Genes

Activated genes were predicted from the sequence of a presumed open reading frame (ORF) gene existing within a 10-Kb range near the T-DNA insertion site (At3g05630) revealed in 1-2-3.

1-2-5. Obtainment of Predicted Genes

For amplification of a fragment containing the ORF region of PP2C (protein phosphatase 2C) gene (At3g05640 (SEQ ID NO:5)) predicted to be activated in 1-2-4, PCR primers 5640PF1 and 5640PR1 were designed and synthesized based on the sequence information disclosed at the TAIR (on world wide web at arabidopsis.org/home). In addition, these primers were designed, so that a restriction enzyme site (BsrG I or Sal I) required for introduction into expression vectors was added to the terminus of each primer.

```
5640PF1 (SEQ ID NO: 29):
5'-ACG CGT CGA CAT GGG ACA TTT CTC TTC CAT GTT

CAA CGG-3'

5640PR1 (SEQ ID NO: 30):
5'-TGT ACA TGT ACA CTA TAG AGA TGG CGA CGA CGA

TGA AGA ATG G-3'
```

According to the method described in 1-2-2, a template DNA was prepared from wild-type *Arabidopsis thaliana* (ecotype Col-0). Phusion High-Fidelity DNA Polymerase (New England BioLabs: NEB) was used as an enzyme and the above 5640PF1 and 5640PR1 were used as primers. The relevant PCR reaction solution composition and reaction conditions are shown in Table 7 and Table 8, respectively.

TABLE 7

| | |
|---|---|
| Template (genomic DNA) | 60 ng |
| 10 × HF buffer (NEB) | 5 μl |
| 10 mM dNTPs (NEB) | 1.0 μl |
| Each primer | 20 pmol |
| Phusion High-Fidelity DNA Polymerase | 1.0 unit |
| Total | 50 μl |

TABLE 8

| | |
|---|---|
| #1: | 98° C. (30 seconds) |
| #2: | 15 cycles of 98° C. (10 seconds)/55° C. (30 seconds)/72° C. (30 seconds) |
| #5: | 72° C. (10 minutes) |

PCR amplification products were subjected to electrophoresis with 2% agarose gel (TAE buffer) and then fragments were stained with ethidium bromide. A gel containing target fragments was excised using a scalpel. Target DNA fragments were eluted and purified using GFX PCR DNA and a GEL Band Purification Kit (Amersham). Adenin was added to the thus obtained DNA fragment using an A-Addition Kit (QIAGEN®). The amplified DNA to which adenine had been added was ligated to a TA-Cloning pCR2.1 vector using a TOPO TA Cloning Kit (Invitrogen®) and then transformed into competent cells (*E. coli* TOP 10) included with the kit. After transformation, cells were cultured in LB medium supplemented with 50 μl/ml kanamycin and then transformants were selected. Colonies that had appeared were subjected to liquid culture in LB medium supplemented with 50 μl/ml kanamycin. Plasmid DNA was prepared from the thus obtained microorganisms using a Plasmid Mini Kit (QIAGEN®). The thus obtained fragment containing ORF of the PP2C (protein phosphatase 2C) gene (At3g05640 (SEQ ID NO:5)) was cloned into a vector, followed by determination of the nucleotide sequence and sequence analysis.

1-2-6. Construction of Plant Expression Vector

A fragment containing ORF of the PP2C (protein phosphatase 2C) gene (At3g05640 (SEQ ID NO:5)) was inserted into a plant expression vector pBI121 containing an omega sequence from tobacco mosaic virus. Thus, a construct was prepared.

First, the pCR2.1 vector, in which a fragment containing ORF of the PP2C (protein phosphatase 2C) gene (At3g05640 (SEQ ID NO:5)) had been cloned in 1-2-5, was treated with restriction enzymes Sal I and BsrG I.

Next, similarly pBI121 containing an omega sequence was treated with restriction enzymes Sal I and BsrG I. The products digested with these restriction enzymes were subjected to 0.8% agarose gel electrophoresis. A fragment of about 2700 bp containing ORF of the PP2C (protein phosphatase 2C) gene (At3g05640 (SEQ ID NO:5)) and pBI121 containing the omega sequence were each fractioned and purified from the gel using GFX PCR DNA and a GEL Band Purification Kit (Amersham).

For introduction of a fragment containing ORF of the PP2C (protein phosphatase 2C) gene (At3g05640 (SEQ ID NO:5)) using a pBI121 fragment containing the omega sequence as a vector, the vector and the insert were mixed at a ratio of 1:10, followed by an overnight ligation reaction at 16° C. using an equivalent amount of a TaKaRa Ligation kit ver. 2 (Takara Bio Inc.).

The total amount of the reaction solution was added to 100 μl of competent cells (*E. coli* strain DH5α, TOYOBO), so that transformation was performed according to protocols included with the kit. Cells were applied to LB agar medium containing 50 μg/ml kanamycin and then cultured overnight. Colonies that had appeared were subjected to liquid culture in LB medium supplemented with 50 μg/ml kanamycin. Plasmid DNA was prepared from the thus obtained microorganisms using a Plasmid Mini Kit (QIAGEN®).

The thus obtained fragment containing ORF of the PP2C (protein phosphatase 2C) gene (At3g05640 (SEQ ID NO:5)) was subcloned into an expression vector, followed by determination of the nucleotide sequence and sequence analysis.

1-2-7. Gene introduction into *Arabidopsis thaliana* using *Agrobacterium* method The plant expression vector constructed in 1-2-6 was introduced into *Agrobacterium tumefaciens* C58C1 strain by electroporation (Plant Molecular Biology Mannal, Second Edition, B. G Stanton and A. S. Robbert, Kluwer Acdemic Publishers 1994). Subsequently, *Agrobacterium tumefaciens* in which the plant expression vector had been introduced was introduced into wild-type *Arabidopsis thaliana* (ecotype Col-0) by an infiltration method described by Clough et al. (Steven J. Clough and Andrew F. Bent, 1998, The Plant Journal 16, 735-743).

Transformants were selected using kanamycin-containing medium. T1 generation plants were produced by self-pollination from the transformants, so that T2 seeds were obtained.

1-2-8. Confirmation of the Phenotype of Transformant

T2 seeds produced in 1-2-7 were aseptically sowed and then the resulting plants were transplanted into pots (each with a diameter of 50 mm) containing vermiculite mixed soil. As control plants for comparison, *Arabidopsis* plants that had not undergone recombination were transplanted. They were cultivated under conditions of 22° C. and 16 hours in the light/8 hours in the dark, and with a light intensity ranging from about 30 to 45 $\mu mol/m^{-2}/s^{-1}$, for a total of 11 weeks after transplantation. After cultivation, above-ground parts of the plants were placed in paper bags and dried under conditions of 22° C. and humidity of 60% for 2 weeks. The total amounts of biomass and seeds were weighed using an electronic balance.

1-3. Results

Regarding the results of 1-2-8, FIG. 3 shows a photo of the above-ground parts of wild-type plants and transformed plants into which a fragment containing ORF of the PP2C (protein phosphatase 2C) gene (At3g05640 (SEQ ID NO:5)) had been introduced. Also, FIG. 4 and FIG. 5 show the results of measuring the total amounts of biomass and seeds of the above-ground parts of the plants.

Figure 4:
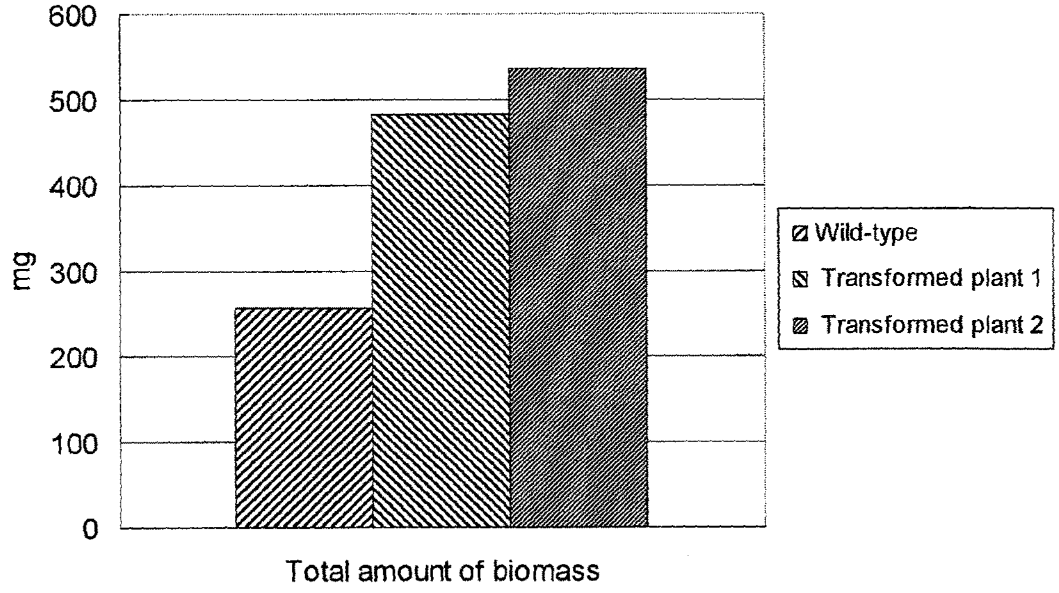
FIG. 4 is a characteristic diagram showing the results of measuring the amounts of biomass of the above-ground parts of wild-type plants and transformed plants into which a fragment containing ORF of the PP2C (protein phosphatase 2C) gene (At3g05640 (SEQ ID NO:5)) was introduced. The result for the wild-type plants is the average value for 12 individual wild-type plants and each result for the transformed plants is the average value for 5 individual transformed plants.
Figure 5:
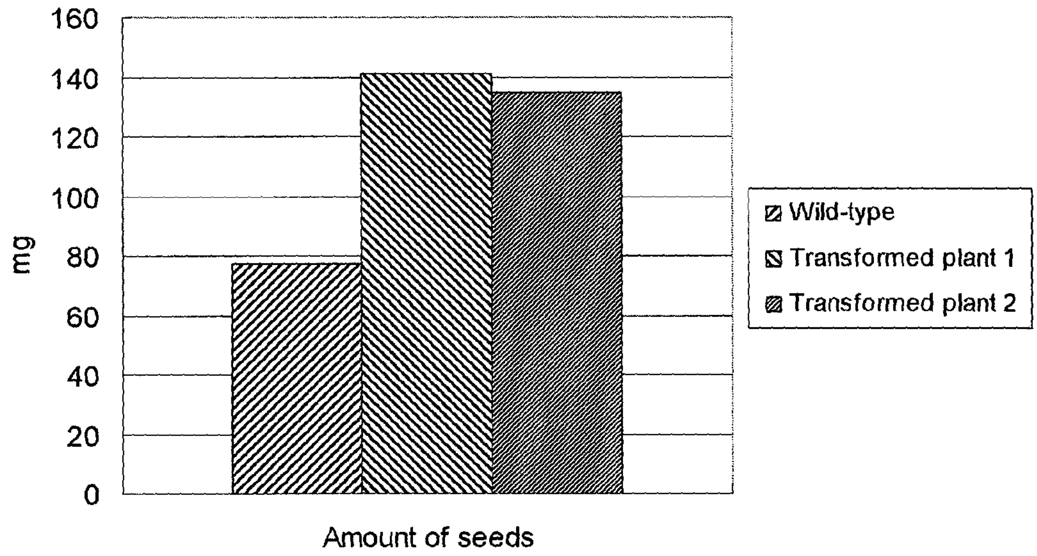
FIG. 5 is a characteristic diagram showing the results of measuring the amounts of seeds of wild-type plants and transformed plants into which a fragment containing ORF of the PP2C (protein phosphatase 2C) gene (At3g05640 (SEQ ID NO:5)) was introduced. The result for wild-type plants is the average value for 12 individual wild-type plants and each result for the transformed plants is the average value for 5 individual transformed plants.

As shown in FIGS. 3, 4, and 5, it was revealed that in the case of transformed plants into which the fragment containing ORF of the PP2C (protein phosphatase 2C) gene (At3g05640 (SEQ ID NO:5)) had been introduced, the total amounts of biomass of the above-ground parts were much higher (about 1.9 to 2.1 times) than the amounts of the same in the cases of wild-type plants. In addition, the amounts of seeds were much greater (by about 1.7 to 1.8 times) than the same in the cases of wild-type plants.

Example 2

Preparation of Transformants (Rice) Through Introduction of the PP2C (Protein Phosphatase 2C) cDNA (At3g05640 (SEQ ID NO:5))

2. Materials and Methods 2-1. Experimental Materials

As experimental materials, *Arabidopsis* transformants into which a fragment containing ORF of the PP2C gene (At3g05640 (SEQ ID NO:5)) prepared in 1 was introduced into *Arabidopsis thaliana* and rice (*Oryza sativa* L. ssp. *japonica* (cv. Nipponbare)) to make transformants as experimental materials.

2-2. Methods 2-2-1. Obtainment of PP2C (Protein Phosphatase 2C) cDNA (At3g05640 (SEQ ID NO:5))

*Arabidopsis* transformants prepared by introduction of a fragment containing ORF of the PP2C gene (At3g05640 (SEQ ID NO:5)) prepared in 1 were grown until the plants reached 4 weeks of age. Total RNA was isolated from the above-ground parts, then RT-PCR was performed using TaqMan Reverse Transcription Reagents (Applied Biosystems), so that cDNA was prepared.

PCR was performed using the following primers that had been designed based on the nucleotide sequence (SEQ ID NO: 4) of the coding region of PP2C (At3g05640 (SEQ ID NO:5)) and PrimeSTAR HS DNA Polymerease (Takara Bio). The thus amplified fragment was TA-cloned into a pCR-Blunt II-TOPO vector (Invitrogen®).

```
                                        (SEQ ID NO: 31)
AP041-F:      5'-AGGATCCATGGGACATTTCTCTTCCATGT-3'

                                        (SEQ ID NO: 32)
AP041-R:      5'-AGAGCTCCTATAGAGATGGCGACGACG-3'
```

2-2-2. Construction of Plant Expression Vector

A GUS (β-Glucuronidase) portion of pIG121-Hm (Ohat, S. et al., 1990, Plant Cell Physiol. 31, 805-813) was substituted with sGFP (S65T) having an intron fragment of *Ricinus communis*-derived catalase, so that a plant expression vector, pBIsGFP, was constructed. Furthermore, a sequence containing pDEST R4-R3 recombination sites (attR4 and attR3) included in a MultiSite Gateway Three-Fragement Vector Construction Kit (Invitrogen®) was inserted, so that a destination vector, pBI-sGFP-R4R3, was constructed.

A corn-derived ubiquitin gene promoter (SEQ ID NO: 33: Christensen, A. H. and Quail, P. H., Transgenic Research 1996, 5, 213-218), PP2C cDNA (At3g05640 (SEQ ID NO:5)) obtained in 2-2-1, and an *Agrobacterium tumefaciens* Ti plasmid-derived nopaline synthase gene (NOS) terminator (obtained from SEQ ID NO: 34: pIG121-Hm) were cloned by BP reaction to result in donor clones, pDONR P4-P1R, pDONR 221, and DONR P2R-P3, respectively, included in a Multi Site Gateway Three-Fragement Vector Construction Kit (Invitrogen), so that entry clones were prepared.

An LR reaction was performed for each of the thus prepared entry clones and a destination vector, pBI-sGFP-R4R3, so that a plant expression vector containing the corn-derived ubiquitin gene promoter, PP2C cDNA (At3g05640 (SEQ ID NO:5)), and the nopaline synthase gene (NOS) terminator, in such order, was constructed. The nucleotide sequences of the thus obtained expression vectors were determined and sequence analysis was conducted.

2-2-3. Gene Introduction into Rice using *Agrobacterium* Method

The plant expression vectors constructed in 2-2-2 were introduced into an *Agrobacterium tumefaciens* EHA101 strain. Then *Agrobacterium tumefaciens* in which the plant expression vector had been introduced was introduced into rice (*Oryza sativa* L. ssp. *japonica* (cv. Nipponbare)). Specifically, the experiment was conducted under conditions in accordance with the method disclosed in JP Patent No. 3141084.

Transformed rice plants that had grown in hygromycin-containing medium were selected and then T1 seedlings (about 12 cm) were aseptically prepared.

2-2-4. Confirmation of Phenotype of Transformant

T1 plants prepared in 2-2-3 were transplanted in pots with a diameter of about 10 cm containing Kumiai Hitetsu culture soil No. 2 (JA Aichi Keizairen (economic federation)). After acclimatization, the plants were transplanted into 1/5000a Wagner pots containing the same culture soil and then cultivated under conditions of 30° C., 16 hours in the light/8 hours in the dark, and a light intensity of about 100 μmol $m^{-2}s^{-1}$.

As control plants, T1 plants into which a plant expression vector (constructed by ligating 3 multiple cloning sites of a pST-Blue1 vector (Novagen) to a destination vector pBI-sGFP-R4R3) had been introduced were similarly cultivated.

2-3. Results

Figure 6:
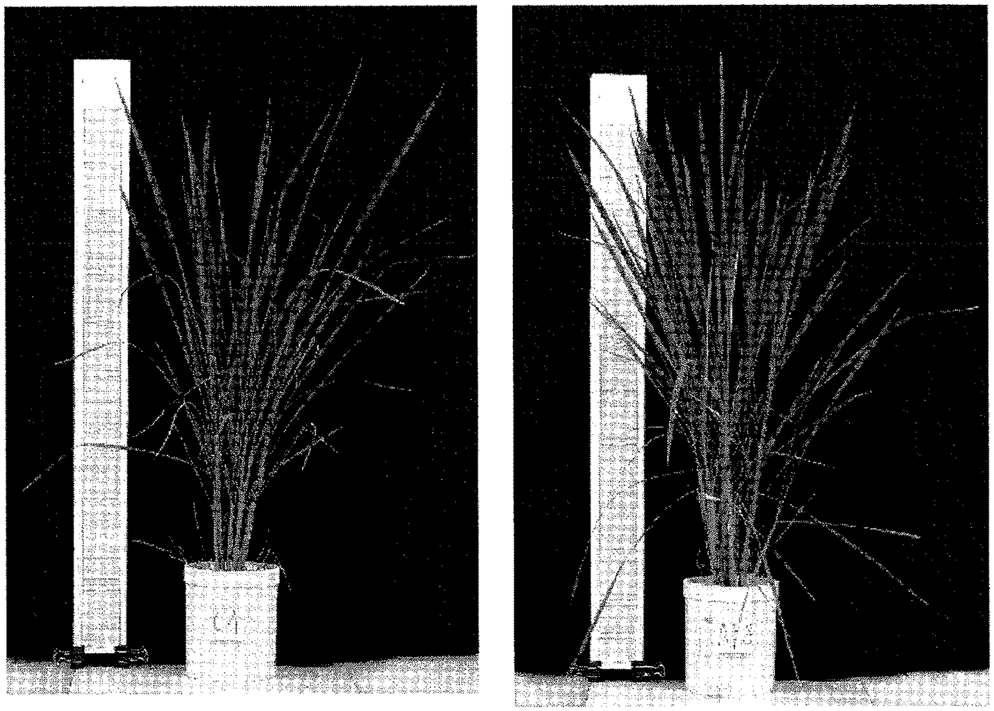
FIG. 6 shows photos showing the above-ground parts of a rice control plant into which a plant expression vector (constructed by ligating 3 multiple cloning sites of a pST-Blue1 vector to pBI-sGFP-R4R3) was introduced and a transformed rice plant into which the coding region of PP2C (protein phosphatase 2C) (At3g05640 (SEQ ID NO:5)) was introduced.

Regarding the results of 2-2-4 above, FIG. 6 shows photos showing a control rice plant and a transformed rice plant prepared by introduction of the coding region of PP2C (protein phosphatase 2C) (At3g05640 (SEQ ID NO:5)). As shown in FIG. 6, in the above-ground parts of the transformed rice plant into which the coding region of PP2C (protein phosphatase 2C) (At3g05640 (SEQ ID NO:5)) had been introduced, the total amount of biomass was improved compared with the control rice plant. It was revealed through the above results that when the *Arabidopsis thaliana*-derived PP2C gene is expressed at a high level in a plant other than *Arabidopsis thaliana*, the production of plant biomass can be increased.

Example 3

Preparation of Transformant (Rice) Through Introduction of PP2C (Protein Phosphatase 2C) cDNA (Os05g0358500 (SEQ ID NO:7))

3. Materials and Methods 3-1. Experimental Materials

As experimental materials, rice (*Oryza sativa* L. ssp. *japonica* (cv. Nipponbare)) was used.

3-2. Methods 3-2-1. Obtainment of Rice PP2C (Protein Phosphatase 2C) cDNA (Os05g0358500 (SEQ ID NO:7))

In this Example, a rice homologous gene (PP2C gene (Os505g0358500 (SEQ ID NO:7)) homologous to PP2C (protein phosphatase 2C) (At3g05640 (SEQ ID NO:5)) used in Examples 1 and 2 was used. The entire sequence was chemically synthesized based on the nucleotide sequence (SEQ ID NO: 6) of the coding region of rice PP2C (Os505g0358500 (SEQ ID NO:7)). A fragment of the chemically synthesized entire sequence was cloned into pDONR 221 that was a donor clone of a MultiSite Gateway Three-Fragment Vector Construction Kit (Invitrogen®).

3-2-2. Construction of Plant Expression Vector

A corn-derived ubiquitin gene promoter (SEQ ID NO: 33: Christensen, A. H. and Quail, P. H., Transgenic Research 1996, 5, 213-218) and an *Agrobacterium tumefaciens* Ti plasmid-derived nopaline synthase gene (NOS) terminator (SEQ ID NO: 34: obtained from pIG121-Hm) were cloned by BP reaction to result in donor clones, pDONR P4-P1R and DONR P2R-P3, respectively, included in a MultiSite Gateway Three-Fragment Vector Construction Kit (Invitrogen®), so that entry clones were prepared.

An LR reaction was performed for pDONR 221 into which the rice PP2C (Os505g0358500 (SEQ ID NO:7)) cDNA sequence prepared in 3-2-1 had been cloned, pDONR P4-P1R into which the above prepared corn-derived ubiquitin gene promoter sequence had been cloned, DONR P2R-P3 into which the nopaline synthase gene (NOS) terminator sequence had been cloned, and the destination vector pBI-sGFP-R4R3 constructed in 2-2-2. Thus, a plant expression vector containing the corn-derived ubiquitin gene promoter, the rice PP2C cDNA (Os05g0358500 (SEQ ID NO:7)), and the nopaline synthase gene (NOS) terminator, in such order, was constructed. The nucleotide sequence of the thus obtained expression vector was determined and then sequence analysis was conducted.

3-2-3. Gene Introduction into Rice Using *Agrobacterium* Method

The plant expression vector constructed in 2-2-2 was introduced into an *Agrobacterium tumefaciens* EHA101 strain. Then *Agrobacterium tumefaciens* in which the plant expression vector had been introduced was introduced into rice (*Oryza sativa* L. ssp. *japonica* (cv. Nipponbare)). Specifically, the experiment was conducted under conditions according to the method disclosed in JP Patent No. 3141084.

Transformed rice plants that had grown in hygromycin-containing medium were selected and then T1 seedlings (about 12 cm) were aseptically prepared.

3-2-4. Confirmation of the Phenotype of Transformant

T1 plants prepared in 3-2-3 were transplanted in pots with a diameter of about 10 cm containing Kumiai Hitetsu culture soil No. 2 (JA Aichi Keizairen (economic federation)). After acclimatization, the plants were transplanted into 1/5000a Wagner pots containing the same culture soil and then cultivated under conditions of 30° C., 16 hours in the light/8 hours in the dark, and a light intensity of about 100 μmol $m^{-2}s^{-1}$.

As control plants, rice plants, into which no gene had been introduced, were regulated to be at almost the same growth stage as that of transformants, transplanted simultaneously with the transplantation of transformants, and then cultivated similarly.

3-3. Results

Figure 7:
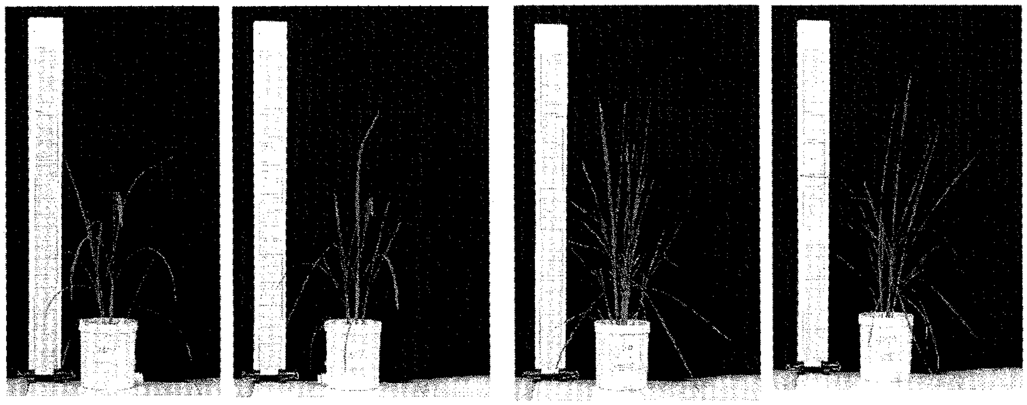
FIG. 7 shows photos showing the above-ground parts of a control rice plant into which no gene was introduced and a transformed rice plant into which the coding region of rice-derived PP2C (protein phosphatase 2C) (Os05g0358500) was introduced.

As the results of 3-2-4 above, FIG. 7 shows photos showing control rice plants and transformed rice plants into which the coding region of rice-derived plant PP2C (protein phosphatase 2C) (Os05g0358500 (SEQ ID NO:7)) had been introduced. As shown in FIG. 7, in the above-ground parts of the transformed rice plants into which the coding region of the rice-derived PP2C (protein phosphatase 2C) (Os505g0358500 (SEQ ID NO:7)) had been introduced, the total amount of biomass was improved compared with the control rice plants. It was revealed by the above results that when the rice-derived PP2C gene is expressed at a high level in a rice plant, the production of rice plant biomass can be increased.

Example 4

Preparation of Transformant (*Arabidopsis thaliana*) Through Introduction of PP2C (Protein Phosphatase 2C) Gene (At5g27930 (SEQ ID NO:36))

4. Materials and Methods 4-1. Experimental Materials

As experimental materials, wild-type *Arabidopsis thaliana* (ecotype Col-0) was used.

4-2. Methods 4-2-1. Obtainment of *Arabidopsis thaliana* PP2C (Protein Phosphatase 2C) Gene (At5g27930 (SEQ ID NO:36))

In this Example, a PP2C (protein phosphatase 2C) gene (At5g27930 (SEQ ID NO:36)) having 3 consensus sequences comprising the amino acid sequences shown in SEQ ID NOS: 1-3 from the N-terminal side in such order was used, instead of PP2C (protein phosphatase 2C) (At3g05640 (SEQ ID NO:5)) used in Examples 1 and 2. For amplification of a fragment containing an ORF region of *Arabidopsis PP*2C (protein phosphatase 2C) gene (At5g27930 (SEQ ID NO:36)), PCR primers, AP042-F5 and AP042-R, were designed and synthesized based on the sequence information disclosed in TAIR (on world wide web at arabidopsis.org/home). Also, PCR primers SalI-AP042-F2 and AP042-BsrGI-R2 were also designed and synthesized so as to add a sequence (restriction enzyme site: BsrG I or Sal I) on the vector side required upon cloning of the thus amplified fragment into the vector using an In-Fusion cloning system (Clontech). The nucleotide sequence of the coding region in the PP2C gene (At5g27930 (SEQ ID NO: 36)) is shown in SEQ ID NO: 35 and the amino acid sequence of the protein encoded by the PP2C gene (At5g27930) is shown in SEQ ID NO: 36.

```
AP042-F5:
                                        (SEQ ID NO: 37)
5'-ATGGGACATTTCTCATCGATGTTC-3'

AP042-R:
                                        (SEQ ID NO: 38)
5'-TTACTTTAAAATCGTCATGGCATGATG-3'

SalI-AP042-F2:
                                        (SEQ ID NO: 39)
5'-AATTACTATTTACAATTACAGTCGACATGGGACATTTCTCATCGATG

TTCAATGGA-3'

AP042-BsrGI-R2:
                                        (SEQ ID NO: 40)
5'-AGCCGGGCGGCCGCTTTACTTGTACATTACTTTAAAATCGTCATGGC

ATGATGATGTTG-3'
```

PCR was performed using template DNA prepared from wild-type *Arabidopsis thaliana* (ecotype Col-0) according to the method of 1-2-2, the above primers, AP042-F5 and AP042-R, and PrimeSTAR HS DNA Polymerase (Takara Bio), so that a fragment containing ORF of the PP2C (protein phosphatase 2C) gene (At5g27930 (SEQ ID NO:36)) was obtained.

4-2-2. Construction of Plant Expression Vector

A fragment containing ORF of the PP2C (protein phosphatase 2C) gene (At5g27930 (SEQ ID NO:36)) was inserted into a plant expression vector pBI121 containing a tobacco mosaic virus-derived omega sequence, so that a construct was prepared.

A fragment containing the PP2C gene (At5g27930 (SEQ ID NO:36)) obtained in 4-2-1 was cloned into a vector using an In-Fusion cloning system (Clontech), so that a construct was prepared. The nucleotide sequence of the thus obtained expression vector in which the fragment containing the PP2C gene (At5g27930 (SEQ ID NO:36)) had been subcloned was determined and sequence analysis was conducted.

4-2-3. Gene Introduction into *Arabidopsis thaliana* Using *Agrobacterium* Method The plant expression vector constructed in 4-2-2 was introduced by electroporation (Plant Molecular Biology Mannal, Second Edition, B. G. Stanton A. S. Robbert, Kluwer Acdemic Publishers 1994) into an *Agrobacterium tumefaciens* C58C1 strain. Subsequently, *Agrobacterium tumefaciens* into which the plant expression vector had been introduced was introduced into wild-type *Arabidopsis thaliana* (ecotype Col-0) by an infiltration method described by Clough et al. (1998, The Plant Journal 16 : 735-743). T1 seeds were obtained by self-pollination.

4-2-4. Confirmation of the Phenotype of Transformant

T1 seeds obtained in 4-2-3 were aseptically sowed in kanamycin-containing medium, so that T1 plants were prepared. Seedlings selected using kanamycin-containing medium were transplanted in pots with a diameter of 50 mm containing vermiculite-mixed soil. As control plants, non-recombinant *Arabidopsis* plants were transplanted. They were cultivated under conditions of 22° C., 16 hours in the light/8 hours in the dark, and a light intensity of about 30-45 $\mu mol\ m^{-2}s^{-1}$.

4-3. Results

Figure 8:
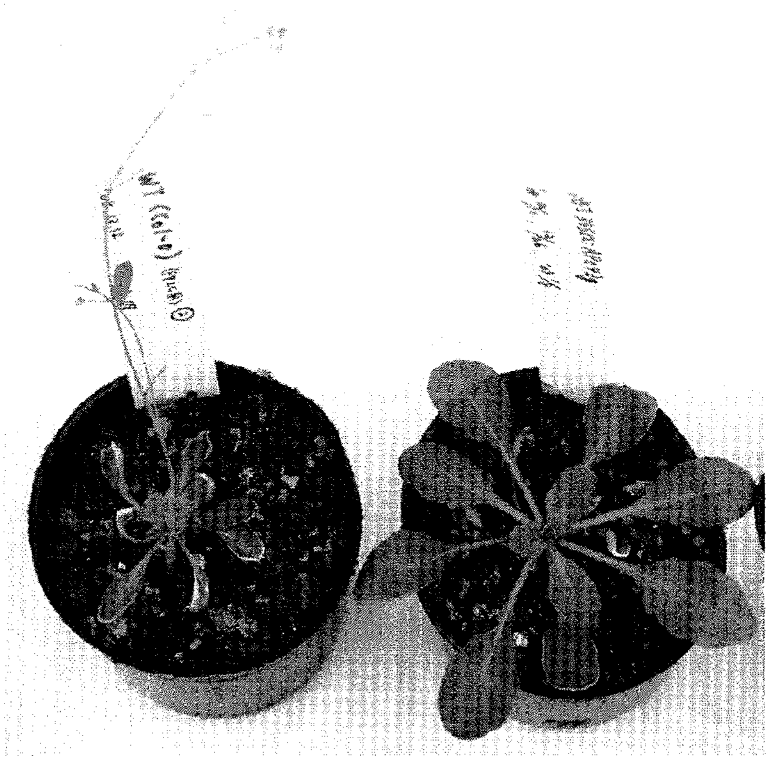
FIG. 8 is a photo showing the above-ground parts of a wild type plant and a transformed plant into which a fragment containing ORF of a PP2C (protein phosphatase 2C) gene (At5g27930 (SEQ ID NO:36)) was introduced.
Figure 9:
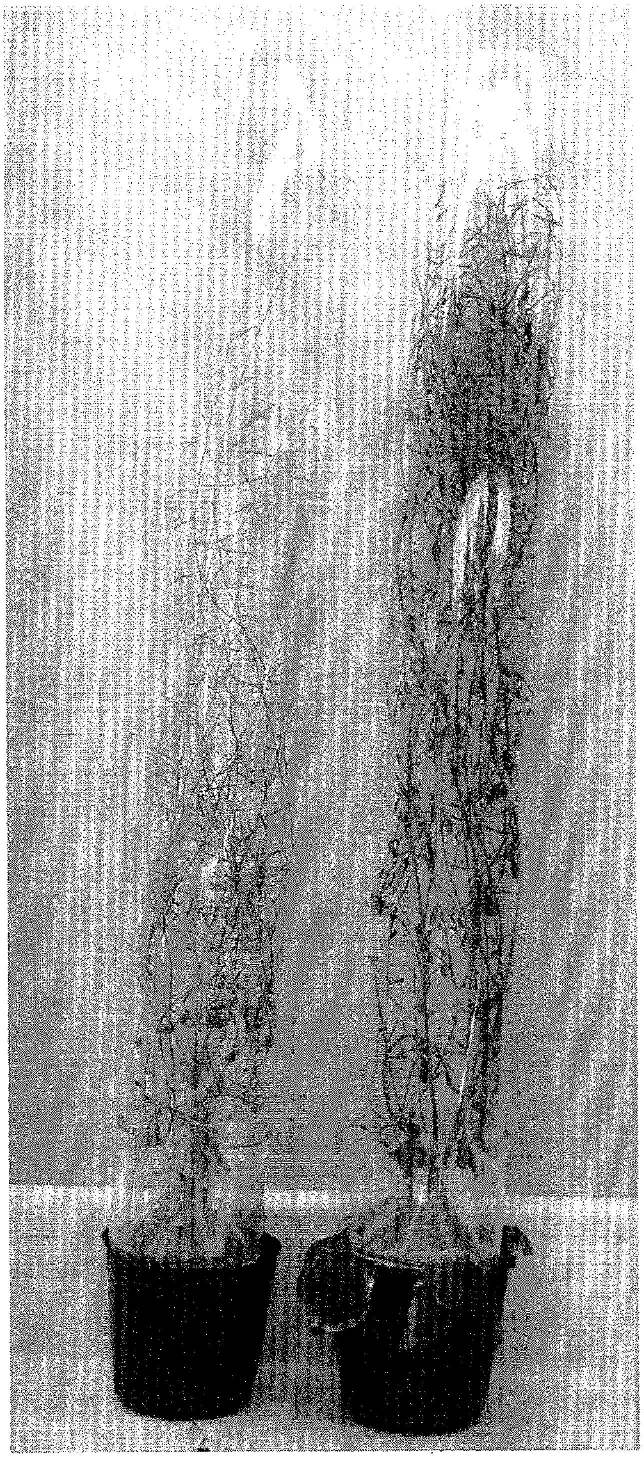
FIG. 9 is a photo showing the above-ground parts of a wild-type plant and a transformed plant into which a fragment containing ORF of a PP2C (protein phosphatase 2C) gene (At5g27930 (SEQ ID NO:36)) was introduced.

As the results of 4-2-4 above, FIGS. 8 and 9 show photos showing the above-ground parts of wild-type plants and transformed plants into which a fragment containing ORF of the PP2C (protein phosphatase 2C) gene (At5g27930 (SEQ ID NO:36)) had been introduced. As shown in FIGS. 8 and 9, in the above-ground parts of the transformed plants into which the fragment containing ORF of the PP2C gene (At5g27930 (SEQ ID NO:36)) had been introduced, the total amount of biomass was improved compared with the wild-type plants. It was revealed by the above results that when the PP2C (protein phosphatase 2C) gene having 3 consensus sequences comprising the amino acid sequences shown in SEQ ID NOS: 1-3 from the N-terminal side in such order is expressed at a high level, the production of the plant biomass can be increased.

Example 5

Preparation of Transformant (*Arabidopsis thaliana*) Through Introduction of PP2C (Protein Phosphatase 2C) Gene (At3g02750 (SEQ ID NO:42))

5. Materials and Methods 5-1. Experimental Materials

As experimental materials, wild-type *Arabidopsis thaliana* (ecotype Col-0) was used.

5-2. Methods 5-2-1. Obtainment of *Arabidopsis thaliana* PP2C (Protein Phosphatase 2C) Gene (At3g02750 (SEQ ID NO:42))

In this Example, a PP2C (protein phosphatase 2C) gene (At3g02750 (SEQ ID NO:42)) having 3 consensus sequences comprising the amino acid sequences shown in SEQ ID NOS: 1-3 from the N-terminal side in such order was used, instead of PP2C (protein phosphatase 2C) (At3g05640 (SEQ ID NO:5)) used in Examples 1 and 2. For amplification of a fragment containing an ORF region of the PP2C (protein phosphatase 2C) gene (At3g02750 (SEQ ID NO:42)), PCR primers, AP036-F4 and AP036-R, were designed and synthesized based on the sequence information disclosed in TAIR (on world wide web at arabidopsis.org/home).

Also, PCR primers, SalI-AP036-F2 and AP036-BsrGI-R2, were designed and synthesized so as to add a sequence (restriction enzyme site: BsrG I or Sal I) on the vector side required upon cloning of the thus amplified fragment into the vector using an In-Fusion cloning system (Clontech). The nucleotide sequence of the coding region in the PP2C gene (At3g02750 (SEQ ID NO:42)) is shown in SEQ ID NO: 41 and the amino acid sequence of the protein encoded by the PP2C gene (At3g02750) is shown in SEQ ID NO: 42.

```
AP036-F4:
                                        (SEQ ID NO: 43)
5'-ATGGGGTCCTGTTTATCTGCAG-3'

AP036-R:
                                        (SEQ ID NO: 44)
5'-TCACTTTCCAGGCACAAATCTTG-3'

SalI-AP036-F2:
                                        (SEQ ID NO: 45)
5'-AATTACTATTTACAATTACAGTCGACATGGGGTCCTGTTTATCTGCA

GAGAGCAGG-3'

AP036-BsrGI-R2:
                                        (SEQ ID NO: 46)
5'-AGCCGGGCGGCCGCTTTACTTGTACATCACTTTCCAGGCACAAATCT

TGGTAAGTT-3'
```

PCR was performed using template DNA prepared from wild-type *Arabidopsis thaliana* (ecotype Col-0) according to the method of 1-2-2, the above primers, and PrimeSTAR HS DNA Polymerase (Takara Bio), so that a fragment containing ORF of the PP2C (protein phosphatase 2C) gene (At3g02750 (SEQ ID NO:42)) was obtained.

5-2-2. Construction of Plant Expression Vector

A fragment containing ORF of the PP2C (protein phosphatase 2C) gene (At3g02750 (SEQ ID NO:42)) was inserted into a plant expression vector pBI121 containing a tobacco mosaic virus-derived omega sequence, so that a construct was prepared.

A fragment containing the PP2C gene (At3g02750 (SEQ ID NO:42)) obtained in 5-2-1 was cloned into a vector using an In-Fusion cloning system (Clontech), so that a construct was prepared. The nucleotide sequence of the thus obtained expression vector in which the fragment containing the PP2C gene (At3g02750 (SEQ ID NO:42)) had been subcloned was determined and sequence analysis was conducted.

5-2-3. Gene Introduction into *Arabidopsis thaliana* Using *Agrobacterium* Method The plant expression vector constructed in 5-2-2 was introduced by electroporation (Plant Molecular Biology Mannal, Second Edition, B. G Stanton A. S. Robbert, Kluwer Acdemic Publishers 1994) into an *Agrobacterium tumefaciens* C58C1 strain. Subsequently, *Agrobacterium tumefaciens* into which the plant expression vector had been introduced was introduced into wild-type *Arabidopsis thaliana* (ecotype Col-0) by an infiltration method described by Clough et al. (1998, The Plant Journal 16: 735-743). T1 seeds were obtained by self-pollination.

5-2-4. Confirmation of the Phenotype of Transformant

T1 seeds obtained in 5-2-3 were aseptically sowed in kanamycin-containing medium, so that T1 plants were prepared. Seedlings selected using kanamycin-containing medium were transplanted in pots with a diameter of 50 mm containing vermiculite-mixed soil. As control plants, non-recombinant *Arabidopsis* plants were transplanted. They were cultivated under conditions of 22° C., 16 hours in the light/8 hours in the dark, and a light intensity of about 30-45 μmol $m^{-2}s^{-1}$.

5-3. Results

Figure 10:
FIG. 10 is a photo showing the above-ground parts of a wild-type plant and transformed plants into which a fragment containing ORF of a PP2C (protein phosphatase 2C) gene (At3g02750 (SEQ ID NO:42)) was introduced.

As the results of 5-2-4 above, FIG. 10 shows a photo showing the above-ground parts of wild-type plants and transformed plants into which a fragment containing ORF of the PP2C (protein phosphatase 2C) gene (At3g02750 (SEQ ID NO:42)) had been introduced. As shown in FIG. 10, in the above-ground parts of the transformed plants into which the fragment containing ORF of the PP2C gene (At3g02750 (SEQ ID NO:42)) had been introduced, the total amount of biomass was improved compared with the wild-type plants. It was revealed by the above results that when the PP2C (protein phosphatase 2C) gene having 3 consensus sequences comprising the amino acid sequences shown in SEQ ID NOS: 1-3 from the N-terminal side in such order is expressed at a high level, the production of the plant biomass can be increased.

Example 6

Preparation of Transformants (*Arabidopsis thaliana*) Through Introduction of PP2C (Protein Phosphatase 2C) Gene (At3g16800 (SEQ ID NO:48))

6. Materials and Methods 6-1. Experimental Materials

As experimental materials, wild-type *Arabidopsis thaliana* (ecotype Col-0) was used.

6-2. Methods 6-2-1. Obtainment of *Arabidopsis thaliana* PP2C (Protein Phosphatase 2C) Gene (At3g16800 (SEQ ID NO:48))

In this Example, a PP2C (protein phosphatase 2C) gene (At3g16800 (SEQ ID NO:48)) having 3 consensus sequences comprising the amino acid sequences shown in SEQ ID NOS: 1-3 from the N-terminal side in such order was used, instead of PP2C (protein phosphatase 2C) (At3g05640 (SEQ ID NO:5)) used in Examples 1 and 2. For amplification of a fragment containing an ORF region of the PP2C (protein phosphatase 2C) gene (At3g16800 (SEQ ID NO:48)), PCR primers, AP040-F4 and AP040-R, were designed and synthesized based on the sequence information disclosed in TAIR (on world wide web at arabidopsis.org/home). Also, PCR primers, SalI-AP040-F2 and AP040-BsrGI-R2, were synthesized and designed so as to add a sequence (restriction enzyme site: BsrG I or Sal I) on the vector side required upon cloning of the thus amplified fragment into the vector using an In-Fusion cloning system (Clontech). The nucleotide sequence of the coding region in the PP2C gene (At3g16800 (SEQ ID NO:48)) is shown in SEQ ID NO: 47 and the amino acid sequence of the protein encoded by the PP2C gene (At3g16800) is shown in SEQ ID NO: 48.

```
AP040-F4:
                                        (SEQ ID NO: 49)
5'-ATGGTGCTTTTACCAGCGTTTTTG-3'

AP040-R:
                                        (SEQ ID NO: 50)
5'-CTAAGAAGGACGAAAGAAGAGAC-3'
```

-continued

```
SalI-AP040-F2:
                                        (SEQ ID NO: 51)
5'-AATTACTATTTACAATTACAGTCGACATGGTGCTTTTACCAGCGTTT

TTGGACGGATTAG-3'

AP040-BsrGI-R2:
                                        (SEQ ID NO: 52)
5'-AGCCGGGCGGCCGCTTTACTTGTACACTAAGAAGGACGAAAGAAGAG

ACAGAGAAC-3'
```

PCR was performed using template DNA prepared from wild-type *Arabidopsis thaliana* (ecotype Col-0) according to the method of 1-2-2, the above primers, and PrimeSTAR HS DNA Polymerase (Takara Bio), so that a fragment containing ORF of the PP2C (protein phosphatase 2C) gene (At3g16800 (SEQ ID NO:48)) was obtained. 6-2-2. Construction of plant expression vector The fragment containing ORF of the PP2C (protein phosphatase 2C) gene (At3g16800 (SEQ ID NO:48)) was inserted to a plant expression vector pBI121 containing a tobacco mosaic virus-derived omega sequence, so that a construct was prepared.

The fragment containing the PP2C gene (At3g16800 (SEQ ID NO:48)) obtained in 6-2-1 was cloned into a vector using an In-Fusion cloning system (Clontech), so that a construct was prepared. The nucleotide sequence of the thus obtained expression vector into which the fragment containing the PP2C gene (At3g16800 (SEQ ID NO:48)) had been subcloned was determined and sequence analysis was conducted.

6-2-3. Gene Introduction into *Arabidopsis thaliana* Using *Agrobacterium* Method The plant expression vector constructed in 6-2-2 was introduced by electroporation (Plant Molecular Biology Mannal, Second Edition, B. G Stanton A. S. Robbert, Kluwer Acdemic Publishers 1994) into an *Agrobacterium tumefaciens* C58C1 strain. Subsequently, *Agrobacterium tumefaciens* into which the plant expression vector had been introduced was introduced into wild-type *Arabidopsis thaliana* (ecotype Col-0) by an infiltration method described by Clough et al. (1998, The Plant Journal 16: 735-743). T1 seeds were obtained by self-pollination.

6-2-4. Confirmation of the Phenotype of Transformant

T1 seeds obtained in 6-2-3 were aseptically sowed in kanamycin-containing medium, so that T1 plants were prepared. Seedlings selected using kanamycin-containing medium were transplanted in pots with a diameter of 50 mm containing vermiculite-mixed soil. As control plants, non-recombinant *Arabidopsis* plants were transplanted. They were cultivated under conditions of 22° C., 16 hours in the light/8 hours in the dark, and a light intensity of about 30-45 μmol $m^{-2}s^{-1}$.

6-3. Results

Figure 11:
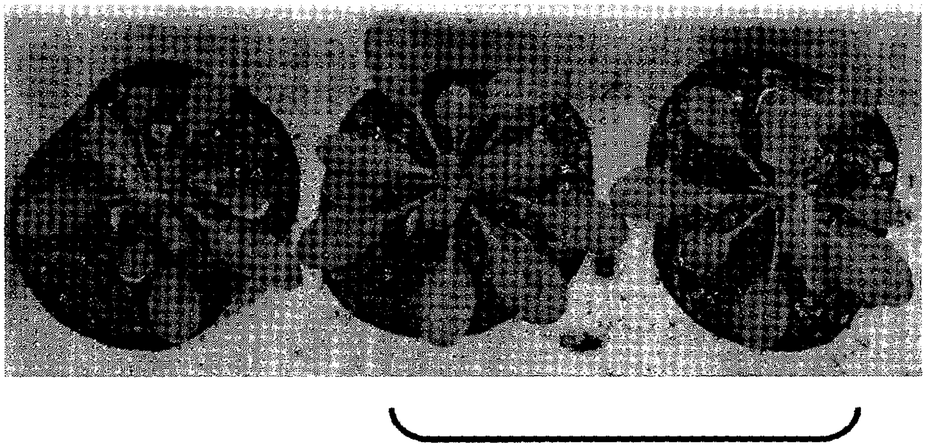
FIG. 11 is a photo showing the above-ground parts of a wild-type plant and transformed plants into which a fragment containing ORF of a PP2C (protein phosphatase 2C) gene (At3g16800 (SEQ ID NO:48)) was introduced.

As the results of 6-2-4 above, FIG. 11 shows a photo showing the above-ground parts of a wild-type plant and transformed plants into which a fragment containing ORF of the PP2C (protein phosphatase 2C) gene (At3g16800 (SEQ ID NO:48)) had been introduced. As shown in FIG. 11, in the above-ground parts of the transformed plants into which the fragment containing ORF of the PP2C gene (At3g16800 (SEQ ID NO:48)) had been introduced, the total amount of biomass was improved compared with the wild-type plant. It was revealed by the above results that when the PP2C (protein phosphatase 2C) gene having 3 consensus sequences comprising the amino acid sequences shown in SEQ ID NOS: 1-3 from the N-terminal side in such order is expressed at a high level, the production of the plant biomass can be increased.

Example 7

Preparation of Transformant (*Arabidopsis thaliana*) Through Introduction of PP2C (Protein Phosphatase 2C) cDNA (Os05g0358500)

7. Materials and Methods 7-1. Experimental Materials

An experimental material, wild-type *Arabidopsis thaliana* (ecotype Col-0) was used.

7-2. Methods 7-2-1. Obtainment of Rice PP2C (Protein Phosphatase 2C) cDNA (Os05g0358500)

In this Example, a rice homologous gene (PP2C gene (Os05g0358500)) homologous to PP2C (protein phosphatase 2C) (At3g05640 (SEQ ID NO:5)) used in Examples 1 and 2 was used. The entire sequence was chemically synthesized based on the nucleotide sequence (SEQ ID NO: 6) of the coding region of rice PP2C (Os05g0358500). A fragment of the chemically synthesized entire sequence was cloned into pDONR 221 that was a donor clone of a MultiSite Gateway Three-Fragement Vector Construction Kit (Invitrogen®).

7-2-2. Construction of Plant Expression Vector

A cauliflower mosaic virus-derived 35S (CaMV35S Ω) promoter (SEQ ID NOS: 58) containing a tobacco mosaic virus-derived omega sequence and an *Agrobacterium tumefaciens* Ti plasmid-derived nopaline synthase gene (NOS) terminator (SEQ ID NOS: 34: obtained from pIG121-Hm) were cloned by BP reaction to result in donor clones, pDONR P4-P1R and DONR P2R-P3, respectively, included in a MultiSite Gateway Three-Fragement Vector Construction Kit (Invitrogen®), so that entry clones were prepared.

An LR reaction was performed for pDONR 221 into which the rice PP2C (Os05g0358500) cDNA sequence prepared in 7-2-1 had been cloned, pDONR P4-P1R into which the above prepared CaMV35S Ω promoter sequence had been cloned, DONR P2R-P3 into which the nopaline synthase gene (NOS) terminator sequence had been cloned, and the destination vector pBI-sGFP-R4R3 constructed in 2-2-2. Thus, a plant expression vector containing the CaMV35S Ω promoter, the rice PP2C cDNA (Os05g0358500), and the nopaline synthase gene (NOS) terminator in such order was constructed. The nucleotide sequence of the thus obtained expression vector was determined and then sequence analysis was conducted.

7-2-3. Gene Introduction into *Arabidopsis thaliana* Using *Agrobacterium* Method The plant expression vector constructed in 7-2-2 was introduced by electroporation (Plant Molecular Biology Mannal, Second Edition, B. G. Stanton A. S. Robbert, Kluwer Acdemic Publishers 1994) into an *Agrobacterium tumefaciens* C58C1 strain. Subsequently, *Agrobacterium tumefaciens* into which the plant expression vector had been introduced was introduced into wild-type *Arabidopsis thaliana* (ecotype Col-0) by an infiltration method described by Clough et al. (1998, The Plant Journal 16: 735-743). T1 seeds were obtained by self-pollination.

7-2-4. Confirmation of the Phenotype of Transformant

T1 seeds obtained in 7-2-3 were aseptically sowed in kanamycin-containing medium, so that T1 plants were prepared. Seedlings selected using kanamycin-containing medium were transplanted in pots with a diameter of 50 mm containing vermiculite-mixed soil. As control plants, non-recombinant *Arabidopsis* plants were transplanted. They were cultivated under conditions of 22° C., 16 hours in the light/8 hours in the dark, and a light intensity of about 30-45 μmol $m^{-2}s^{-1}$.

7-3. Results

Figure 12:
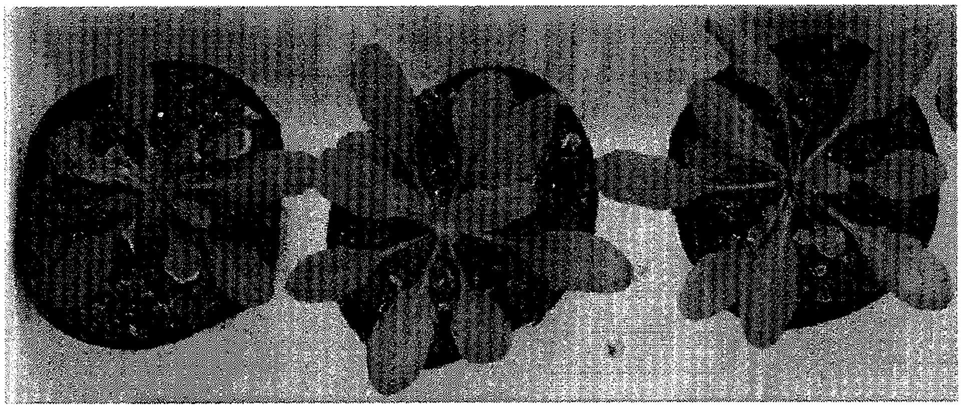
FIG. 12 is a photo showing the above-ground parts of a wild-type plant and transformed plants into which the coding region of a rice-derived PP2C (protein phosphatase 2C) gene (Os05g0358500 (SEQ ID NO: 7)) was introduced.

As the results of 7-2-4 above, FIG. 12 shows a photo showing the above-ground parts of a wild-type plant and transformed plants into which the coding region of the rice-derived PP2C (protein phosphatase 2C) gene (Os05g0358500) had been introduced. As shown in FIG. 12, in the above-ground parts of the transformed plants into which the coding region of the rice-derived PP2C gene (Os05g0358500) had been introduced, the total amount of biomass was improved compared with the wild-type plant. It was revealed by the above results that when the rice-derived PP2C gene is expressed at a high level in *Arabidopsis thaliana*, the production of *Arabidopsis* biomass can be increased.

All publications, patents, and patent applications cited herein are incorporated herein by reference in their entirety.

The invention claimed is:

1. A method for increasing the production of biomass comprising introducing, into a plant, a gene encoding a protein phosphatase 2C which comprises a protein selected from the group consisting of (a) and (b):

(a) a protein comprising SEQ ID NO: 7; and (b) a protein comprising an amino acid sequence that has a deletion of one to five amino acids, a substitution of one to five amino acids, an addition of one to five amino acids, or an insertion of one to five amino acids with respect to SEQ ID NO: 7 and having protein phosphatase 2C activity; and thereby increasing the production of biomass as compared to a wild-type plant.

2. A method for producing a transformed plant comprising introducing, into a plant, a gene encoding a protein phosphatase 2C which comprises a protein selected from the group consisting of (a) and (b):

(a) a protein comprising SEQ ID NO: 7; and (b) a protein comprising an amino acid sequence that has a deletion of one to five amino acids, a substitution of one to five amino acids, an addition of one to five amino acids, or an insertion of one to five amino acids with respect to SEQ ID NO: 7 and having protein phosphatase 2C activity;

thereby producing a transformed plant.

3. The method according to claim 1, wherein the plant is a dicotyledon.

4. The method according to claim 1, wherein the plant is a plant of the family Brassicaceae.

5. The method according to claim 1, wherein the plant is *Arabidopsis thaliana.*

6. The method according to claim 1, wherein the plant is *Brassica rapa.*

7. The method according to claim 1, wherein the plant is a monocotyledon.

8. The method according to claim 1, wherein the plant is a plant of the family Gramineae.

9. The method according to claim 1, wherein the plant is rice.

10. The method according to claim 1, wherein the plant is sugarcane.

11. The method according to claim 2, wherein the plant is a dicotyledon.

12. The method according to claim 2, wherein the plant is a plant of the family Brassicaceae.

13. The method according to claim 2, wherein the plant is *Arabidopsis thaliana.*

14. The method according to claim 2, wherein the plant is *Brassica rapa.*

15. The method according to claim 2, wherein the plant is a monocotyledon.

16. The method according to claim 2, wherein the plant is a plant of the family Gramineae.

17. The method according to claim 2, wherein the plant is rice.

18. The method according to claim 2, wherein the plant is sugarcane.

* * * * *

SEQUENCE LISTING

```
<160> NUMBER OF SEQ ID NOS: 67

<210> SEQ ID NO 1
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
      or preferably L or F
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably V, I or M
<220> FEATURE:
<221> NAME/KEY: misc_feature
<222> LOCATION: (10)..(11)
```

<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid, or preferably S or A
<220> FEATURE:
<221> NAME/KEY: misc_feature
<222> LOCATION: (17)..(17)
<223> OTHER INFORMATION: Xaa can be any naturally occurring amino acid, or preferably K, R, Q or N
<220> FEATURE:
<221> NAME/KEY: misc_feature
<222> LOCATION: (18)..(18)
<223> OTHER INFORMATION: Xaa can be any naturally occurring amino acid

<400> SEQUENCE: 1

```
Xaa Xaa Gly Xaa Phe Asp Gly His Gly Xaa Xaa Gly Xaa Xaa Xaa Xaa
1               5                   10                  15

Xaa Xaa Val
```

<210> SEQ ID NO 2
<211> LENGTH: 27
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid, or preferably G, A or S
<220> FEATURE:
<221> NAME/KEY: misc_feature
<222> LOCATION: (6)..(6)
<223> OTHER INFORMATION: Xaa can be any naturally occurring amino acid, or preferably V, L or I
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid, or preferably I, V, F, M or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid, or preferably G or A
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid, or preferably L, V or I
<220> FEATURE:
<221> NAME/KEY: misc_feature
<222> LOCATION: (16)..(16)
<223> OTHER INFORMATION: Xaa can be any naturally occurring amino acid

```
<220> FEATURE:
<221> NAME/KEY: misc_feature
<222> LOCATION: (17)..(17)
<223> OTHER INFORMATION: Xaa can be any naturally occurring amino acid,
      or preferably I, V or M
<220> FEATURE:
<221> NAME/KEY: misc_feature
<222> LOCATION: (18)..(18)
<223> OTHER INFORMATION: Xaa can be any naturally occurring amino acid,
      or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid,
      or preferably D or H
<220> FEATURE:
<221> NAME/KEY: misc_feature
<222> LOCATION: (26)..(26)
<223> OTHER INFORMATION: Xaa can be any naturally occurring amino acid,
      or preferably V or I
<220> FEATURE:
<221> NAME/KEY: misc_feature
<222> LOCATION: (27)..(27)
<223> OTHER INFORMATION: Xaa can be any naturally occurring amino acid,
      or preferably L, M or I

<400> SEQUENCE: 2

Ser Gly Xaa Thr Xaa Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25


<210> SEQ ID NO 3
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably M, V or F
<220> FEATURE:
<221> NAME/KEY: misc_feature
<222> LOCATION: (5)..(5)
<223> OTHER INFORMATION: Xaa can be any naturally occurring amino acid,
      or preferably S, A or T
<220> FEATURE:
<221> NAME/KEY: misc_feature
<222> LOCATION: (7)..(7)
<223> OTHER INFORMATION: Xaa can be any naturally occurring amino acid,
      or preferably A or S
<220> FEATURE:
<221> NAME/KEY: misc_feature
<222> LOCATION: (8)..(8)
<223> OTHER INFORMATION: Xaa can be any naturally occurring amino acid,
      or preferably F, I or V
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid,
      or preferably K or E
<220> FEATURE:
```

```
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid,
      or preferably V or L
<220> FEATURE:
<221> NAME/KEY: misc_feature
<222> LOCATION: (19)..(19)
<223> OTHER INFORMATION: Xaa can be any naturally occurring amino acid,
      or preferably I or V
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
      or preferably E, Q or D
<220> FEATURE:
<221> NAME/KEY: misc_feature
<222> LOCATION: (24)..(24)
<223> OTHER INFORMATION: Xaa can be any naturally occurring amino acid,
      or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
      or preferably I, L or V
<220> FEATURE:
<221> NAME/KEY: misc_feature
<222> LOCATION: (30)..(30)
<223> OTHER INFORMATION: Xaa can be any naturally occurring amino acid,
      or preferably T or S
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid,
      or preferably D, N or H
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid,
      or preferably F or Y
<220> FEATURE:
<221> NAME/KEY: misc_feature
<222> LOCATION: (36)..(36)
<223> OTHER INFORMATION: Xaa can be any naturally occurring amino acid,
      or preferably L, I, V or F
<220> FEATURE:
<221> NAME/KEY: misc_feature
<222> LOCATION: (37)..(37)
<223> OTHER INFORMATION: Xaa can be any naturally occurring amino acid,
      or preferably V, L or I
<220> FEATURE:
<221> NAME/KEY: misc_feature
<222> LOCATION: (38)..(38)
<223> OTHER INFORMATION: Xaa can be any naturally occurring amino acid,
      or preferably L or V
<220> FEATURE:
```

-continued

```
<221> NAME/KEY: misc_feature
<222> LOCATION: (40)..(40)
<223> OTHER INFORMATION: Xaa can be any naturally occurring amino acid,
      or preferably T or S
<220> FEATURE:
<221> NAME/KEY: misc_feature
<222> LOCATION: (43)..(43)
<223> OTHER INFORMATION: Xaa can be any naturally occurring amino acid,
      or preferably V, I or M
<220> FEATURE:
<221> NAME/KEY: misc_feature
<222> LOCATION: (44)..(44)
<223> OTHER INFORMATION: Xaa can be any naturally occurring amino acid,
      or preferably W or F
<220> FEATURE:
<221> NAME/KEY: misc_feature
<222> LOCATION: (45)..(45)
<223> OTHER INFORMATION: Xaa can be any naturally occurring amino acid,
      or preferably D or E
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid,
      or preferably L, I or M
<220> FEATURE:
<221> NAME/KEY: misc_feature
<222> LOCATION: (48)..(48)
<223> OTHER INFORMATION: Xaa can be any naturally occurring amino acid,
      or preferably S, T or P
<220> FEATURE:
<221> NAME/KEY: misc_feature
<222> LOCATION: (49)..(49)
<223> OTHER INFORMATION: Xaa can be any naturally occurring amino acid,
      or preferably N or S
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid,
      or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid,
      or preferably L, V, I or M
<220> FEATURE:
<221> NAME/KEY: misc_feature
<222> LOCATION: (56)..(56)
<223> OTHER INFORMATION: Xaa can be any naturally occurring amino acid,
      or preferably I or V

<400> SEQUENCE: 3

Gly Xaa Ala Xaa Xaa Arg Xaa Xaa Gly Asp Xaa Xaa Xaa Xaa Xaa Xaa
1               5                   10                  15

Gly Xaa Xaa Xaa Xaa Pro Xaa Xaa Xaa Xaa Xaa Xaa Xaa Xaa Xaa Xaa
            20                  25                  30

Xaa Xaa Xaa Xaa Xaa Xaa Ala Xaa Asp Gly Xaa Xaa Xaa Xaa Xaa Xaa
        35                  40                  45

Xaa Xaa Xaa Xaa Xaa Xaa Xaa Xaa
    50                  55
```

<210> SEQ ID NO 4
<211> LENGTH: 1077
<212> TYPE: DNA
<213> ORGANISM: Arabidopsis thaliana
<220> FEATURE:
<221> NAME/KEY: CDS
<222> LOCATION: (1)..(1077)

<400> SEQUENCE: 4

```
atg gga cat ttc tct tcc atg ttc aac ggt ata gct aga tcc ttc tcg       48
Met Gly His Phe Ser Ser Met Phe Asn Gly Ile Ala Arg Ser Phe Ser
1               5                   10                  15

atc aag aaa gcg aag aac atc aac agc agc aaa agc tac gct aag gaa       96
Ile Lys Lys Ala Lys Asn Ile Asn Ser Ser Lys Ser Tyr Ala Lys Glu
            20                  25                  30

gcc aca gat gaa atg gcg aga gag gcg aag aag aag gaa ctt att ttg      144
Ala Thr Asp Glu Met Ala Arg Glu Ala Lys Lys Lys Glu Leu Ile Leu
        35                  40                  45

aga tcc tct ggt tgc att aat gca gat gga tct aat aac ttg gct tct      192
Arg Ser Ser Gly Cys Ile Asn Ala Asp Gly Ser Asn Asn Leu Ala Ser
    50                  55                  60

gtt ttc tct aga cgc ggt gag aaa ggc gtt aat cag gac tgt gcc atc      240
Val Phe Ser Arg Arg Gly Glu Lys Gly Val Asn Gln Asp Cys Ala Ile
65                  70                  75                  80

gtc tgg gag gga tat ggg tgt caa gaa gac atg ata ttc tgt ggg ata      288
Val Trp Glu Gly Tyr Gly Cys Gln Glu Asp Met Ile Phe Cys Gly Ile
                85                  90                  95

ttc gat gga cat ggt ccc tgg gga cac ttt gtt tct aaa caa gtc aga      336
Phe Asp Gly His Gly Pro Trp Gly His Phe Val Ser Lys Gln Val Arg
            100                 105                 110

aac tca atg cct ata tct ttg ctc tgt aac tgg aaa gag act ctt tct      384
Asn Ser Met Pro Ile Ser Leu Leu Cys Asn Trp Lys Glu Thr Leu Ser
        115                 120                 125

cag acc aca ata gca gaa ccc gat aaa gag cta cag cgg ttt gca atc      432
Gln Thr Thr Ile Ala Glu Pro Asp Lys Glu Leu Gln Arg Phe Ala Ile
    130                 135                 140

tgg aaa tac tca ttc ctc aaa acc tgt gaa gct gtt gat ctg gag ctt      480
Trp Lys Tyr Ser Phe Leu Lys Thr Cys Glu Ala Val Asp Leu Glu Leu
145                 150                 155                 160

gag cat cac cga aag ata gat tct ttc aac agc ggt acg acc gct cta      528
Glu His His Arg Lys Ile Asp Ser Phe Asn Ser Gly Thr Thr Ala Leu
                165                 170                 175

acc att gtg aga cag ggt gat gtt att tat ata gca aac gtc ggg gat      576
Thr Ile Val Arg Gln Gly Asp Val Ile Tyr Ile Ala Asn Val Gly Asp
            180                 185                 190

tca cgt gcg gta ttg gcc aca gtt tca gac gaa gga agc ttg gtc gcg      624
Ser Arg Ala Val Leu Ala Thr Val Ser Asp Glu Gly Ser Leu Val Ala
        195                 200                 205

gtt cag ctc acc gta gat ttc aag cca aac ctg cct cag gag gaa gag      672
Val Gln Leu Thr Val Asp Phe Lys Pro Asn Leu Pro Gln Glu Glu Glu
    210                 215                 220

cgg ata atc gga tgc aac ggg aga gta ttt tgc ctt caa gat gag cca      720
Arg Ile Ile Gly Cys Asn Gly Arg Val Phe Cys Leu Gln Asp Glu Pro
225                 230                 235                 240

ggg gtc cac cgt gta tgg caa cca gta gat gaa tct ccg ggg ctc gca      768
Gly Val His Arg Val Trp Gln Pro Val Asp Glu Ser Pro Gly Leu Ala
                245                 250                 255

atg tca aga gca ttc gga gac tat tgt atc aaa gat tac gga ttg gtc      816
Met Ser Arg Ala Phe Gly Asp Tyr Cys Ile Lys Asp Tyr Gly Leu Val
                260                 265                 270
```

-continued

```
tca gtg cct gaa gtc act cag agg cat ata tcc att aga gac cag ttt      864
Ser Val Pro Glu Val Thr Gln Arg His Ile Ser Ile Arg Asp Gln Phe
        275                 280                 285

ata atc ttg gcc act gat ggg gta tgg gat gtg ata tca aac caa gag      912
Ile Ile Leu Ala Thr Asp Gly Val Trp Asp Val Ile Ser Asn Gln Glu
    290                 295                 300

gcc ata gat att gtt tcc tcg acg gcg gag cgg gca aaa gct gcc aag      960
Ala Ile Asp Ile Val Ser Ser Thr Ala Glu Arg Ala Lys Ala Ala Lys
305                 310                 315                 320

cga ctg gta cag caa gca gtt agg gct tgg aat aga aag aga cgc gga     1008
Arg Leu Val Gln Gln Ala Val Arg Ala Trp Asn Arg Lys Arg Arg Gly
                325                 330                 335

atc gcc atg gat gat atc tct gcc gtg tgc ctc ttc ttc cat tct tca     1056
Ile Ala Met Asp Asp Ile Ser Ala Val Cys Leu Phe Phe His Ser Ser
            340                 345                 350

tcg tcg tcg cca tct cta tag                                         1077
Ser Ser Ser Pro Ser Leu
        355


<210> SEQ ID NO 5
<211> LENGTH: 358
<212> TYPE: PRT
<213> ORGANISM: Arabidopsis thaliana

<400> SEQUENCE: 5

Met Gly His Phe Ser Ser Met Phe Asn Gly Ile Ala Arg Ser Phe Ser
1               5                   10                  15

Ile Lys Lys Ala Lys Asn Ile Asn Ser Ser Lys Ser Tyr Ala Lys Glu
            20                  25                  30

Ala Thr Asp Glu Met Ala Arg Glu Ala Lys Lys Lys Glu Leu Ile Leu
        35                  40                  45

Arg Ser Ser Gly Cys Ile Asn Ala Asp Gly Ser Asn Asn Leu Ala Ser
    50                  55                  60

Val Phe Ser Arg Arg Gly Glu Lys Gly Val Asn Gln Asp Cys Ala Ile
65                  70                  75                  80

Val Trp Glu Gly Tyr Gly Cys Gln Glu Asp Met Ile Phe Cys Gly Ile
                85                  90                  95

Phe Asp Gly His Gly Pro Trp Gly His Phe Val Ser Lys Gln Val Arg
            100                 105                 110

Asn Ser Met Pro Ile Ser Leu Leu Cys Asn Trp Lys Glu Thr Leu Ser
        115                 120                 125

Gln Thr Thr Ile Ala Glu Pro Asp Lys Glu Leu Gln Arg Phe Ala Ile
    130                 135                 140

Trp Lys Tyr Ser Phe Leu Lys Thr Cys Glu Ala Val Asp Leu Glu Leu
145                 150                 155                 160

Glu His His Arg Lys Ile Asp Ser Phe Asn Ser Gly Thr Thr Ala Leu
                165                 170                 175

Thr Ile Val Arg Gln Gly Asp Val Ile Tyr Ile Ala Asn Val Gly Asp
            180                 185                 190

Ser Arg Ala Val Leu Ala Thr Val Ser Asp Glu Gly Ser Leu Val Ala
        195                 200                 205

Val Gln Leu Thr Val Asp Phe Lys Pro Asn Leu Pro Gln Glu Glu Glu
    210                 215                 220

Arg Ile Ile Gly Cys Asn Gly Arg Val Phe Cys Leu Gln Asp Glu Pro
225                 230                 235                 240

Gly Val His Arg Val Trp Gln Pro Val Asp Glu Ser Pro Gly Leu Ala
```

-continued

```
                245                 250                 255

Met Ser Arg Ala Phe Gly Asp Tyr Cys Ile Lys Asp Tyr Gly Leu Val
            260                 265                 270

Ser Val Pro Glu Val Thr Gln Arg His Ile Ser Ile Arg Asp Gln Phe
        275                 280                 285

Ile Ile Leu Ala Thr Asp Gly Val Trp Asp Val Ile Ser Asn Gln Glu
    290                 295                 300

Ala Ile Asp Ile Val Ser Ser Thr Ala Glu Arg Ala Lys Ala Ala Lys
305                 310                 315                 320

Arg Leu Val Gln Gln Ala Val Arg Ala Trp Asn Arg Lys Arg Arg Gly
            325                 330                 335

Ile Ala Met Asp Asp Ile Ser Ala Val Cys Leu Phe Phe His Ser Ser
            340                 345                 350

Ser Ser Ser Pro Ser Leu
        355


<210> SEQ ID NO 6
<211> LENGTH: 1176
<212> TYPE: DNA
<213> ORGANISM: Oryza sativa
<220> FEATURE:
<221> NAME/KEY: CDS
<222> LOCATION: (1)..(1176)

<400> SEQUENCE: 6

atg cgg cac atc tcg tcg ctg ctg cag ggg ctg gcg cgc tcg ctg tcg       48
Met Arg His Ile Ser Ser Leu Leu Gln Gly Leu Ala Arg Ser Leu Ser
1               5                   10                  15

gtg ggg aag gag agg aag ggc ggc gac ggc gac gac ggg aag gcg gcg       96
Val Gly Lys Glu Arg Lys Gly Gly Asp Gly Asp Asp Gly Lys Ala Ala
            20                  25                  30

gcg gcg acg gcg acg gcg gtg ctg agg aca tcg ggg acg ctg tgg ggc      144
Ala Ala Thr Ala Thr Ala Val Leu Arg Thr Ser Gly Thr Leu Trp Gly
        35                  40                  45

gag ggc tct gag acg ttc gcc gcc gtc tgc tcc cgc cgc ggc gag aag      192
Glu Gly Ser Glu Thr Phe Ala Ala Val Cys Ser Arg Arg Gly Glu Lys
    50                  55                  60

ggc atc aac cag gac tgc tcc atc gtc tgc gag gga ttc ggg tgc gag      240
Gly Ile Asn Gln Asp Cys Ser Ile Val Cys Glu Gly Phe Gly Cys Glu
65                  70                  75                  80

gag ggg agc gtg ttg tgc ggc atc ttc gac ggg cac ggg cag tgg ggc      288
Glu Gly Ser Val Leu Cys Gly Ile Phe Asp Gly His Gly Gln Trp Gly
                85                  90                  95

cac tac gtg gcg aag gcg gtg agg gag tcg ctg ccg ccg gcg ctg ctc      336
His Tyr Val Ala Lys Ala Val Arg Glu Ser Leu Pro Pro Ala Leu Leu
            100                 105                 110

cgg cgg tgg cgg gag gcc gtg acg ctg gcg gcg ctc atc gac ggc ggc      384
Arg Arg Trp Arg Glu Ala Val Thr Leu Ala Ala Leu Ile Asp Gly Gly
        115                 120                 125

gag aag cgg ctc tgc gag tgc cgg ccc gac ctg tgg cgc cag tcc tac      432
Glu Lys Arg Leu Cys Glu Cys Arg Pro Asp Leu Trp Arg Gln Ser Tyr
    130                 135                 140

ctg gcc gcc tgc gcc gcc gtc gac gcc gag ctc cgc gcc agc cgc cgc      480
Leu Ala Ala Cys Ala Ala Val Asp Ala Glu Leu Arg Ala Ser Arg Arg
145                 150                 155                 160

ctc gac gcc gtc cac agc ggc tgc acc gcg ctg tcc ctc gtc aag cac      528
Leu Asp Ala Val His Ser Gly Cys Thr Ala Leu Ser Leu Val Lys His
                165                 170                 175

ggc gac ctc ctc gtc gtc gcc aac gtc ggc gac tcg cgc gcc gtc ctg      576
```

-continued

```
Gly Asp Leu Leu Val Val Ala Asn Val Gly Asp Ser Arg Ala Val Leu
            180                 185                 190

gcc acc gcc tcc ccc gac gac ggt ggc ggc gcc cgc ctc gcc gcc gtg      624
Ala Thr Ala Ser Pro Asp Asp Gly Gly Gly Ala Arg Leu Ala Ala Val
        195                 200                 205

cag ctc acc gtc gac ttc aag ccc aac ctg ccc cag gag agg gag agg      672
Gln Leu Thr Val Asp Phe Lys Pro Asn Leu Pro Gln Glu Arg Glu Arg
    210                 215                 220

atc atg gag tgc aac ggg agg gtg cag tgc ctc gcc gac gag ccc ggg      720
Ile Met Glu Cys Asn Gly Arg Val Gln Cys Leu Ala Asp Glu Pro Gly
225                 230                 235                 240

gtg cac cgg gtg tgg cgg ccg gac agg gag ggc cca ggc ctc gcc atg      768
Val His Arg Val Trp Arg Pro Asp Arg Glu Gly Pro Gly Leu Ala Met
                245                 250                 255

tcg cgc gcc ttc ggc gac tac tgc gtc aag gat tac ggc gtc atc tcg      816
Ser Arg Ala Phe Gly Asp Tyr Cys Val Lys Asp Tyr Gly Val Ile Ser
            260                 265                 270

gcg ccg gag gtg acg cac cgc cgg atc acc gcc cag gac cac ttc gtc      864
Ala Pro Glu Val Thr His Arg Arg Ile Thr Ala Gln Asp His Phe Val
        275                 280                 285

atc ctc gcc acc gac ggg gac aaa cat ctc aac ttg ttc gtc ttc gtc      912
Ile Leu Ala Thr Asp Gly Asp Lys His Leu Asn Leu Phe Val Phe Val
    290                 295                 300

tgc gcg gca ggt gtg gga cgt ggt gtc gaa cga gga ggc ggt gca gat      960
Cys Ala Ala Gly Val Gly Arg Gly Val Glu Arg Gly Gly Gly Ala Asp
305                 310                 315                 320

cgt ggc gtc ggc gcc gga gag gga gaa ggc ggc gaa gcg gct cgt cga     1008
Arg Gly Val Gly Ala Gly Glu Gly Glu Gly Gly Glu Ala Ala Arg Arg
                325                 330                 335

gtt cgc cgt ccg ggc atg gag gcg caa gcg ccg ggg cat cgc cgt cga     1056
Val Arg Arg Pro Gly Met Glu Ala Gln Ala Pro Gly His Arg Arg Arg
            340                 345                 350

cga ctg ctc ggc gat ctg cct ctt ctt cca ctc gcc gcc gtc cta aac     1104
Arg Leu Leu Gly Asp Leu Pro Leu Leu Pro Leu Ala Ala Val Leu Asn
        355                 360                 365

aac aca cac gct gac acg cac gca gcc aac aaa aac cgc aca cgc cga     1152
Asn Thr His Ala Asp Thr His Ala Ala Asn Lys Asn Arg Thr Arg Arg
    370                 375                 380

cga caa tgt cgc cgt cgt cgt tga                                     1176
Arg Gln Cys Arg Arg Arg Arg
385                 390


<210> SEQ ID NO 7
<211> LENGTH: 391
<212> TYPE: PRT
<213> ORGANISM: Oryza sativa

<400> SEQUENCE: 7

Met Arg His Ile Ser Ser Leu Leu Gln Gly Leu Ala Arg Ser Leu Ser
1               5                   10                  15

Val Gly Lys Glu Arg Lys Gly Gly Asp Gly Asp Asp Gly Lys Ala Ala
            20                  25                  30

Ala Ala Thr Ala Thr Ala Val Leu Arg Thr Ser Gly Thr Leu Trp Gly
        35                  40                  45

Glu Gly Ser Glu Thr Phe Ala Ala Val Cys Ser Arg Arg Gly Glu Lys
    50                  55                  60

Gly Ile Asn Gln Asp Cys Ser Ile Val Cys Glu Gly Phe Gly Cys Glu
65                  70                  75                  80

Glu Gly Ser Val Leu Cys Gly Ile Phe Asp Gly His Gly Gln Trp Gly
```

-continued 85 90 95

His Tyr Val Ala Lys Ala Val Arg Glu Ser Leu Pro Pro Ala Leu Leu
100 105 110

Arg Arg Trp Arg Glu Ala Val Thr Leu Ala Ala Leu Ile Asp Gly Gly
115 120 125

Glu Lys Arg Leu Cys Glu Cys Arg Pro Asp Leu Trp Arg Gln Ser Tyr
130 135 140

Leu Ala Ala Cys Ala Ala Val Asp Ala Glu Leu Arg Ala Ser Arg Arg
145 150 155 160

Leu Asp Ala Val His Ser Gly Cys Thr Ala Leu Ser Leu Val Lys His
165 170 175

Gly Asp Leu Leu Val Val Ala Asn Val Gly Asp Ser Arg Ala Val Leu
180 185 190

Ala Thr Ala Ser Pro Asp Asp Gly Gly Gly Ala Arg Leu Ala Ala Val
195 200 205

Gln Leu Thr Val Asp Phe Lys Pro Asn Leu Pro Gln Glu Arg Glu Arg
210 215 220

Ile Met Glu Cys Asn Gly Arg Val Gln Cys Leu Ala Asp Glu Pro Gly
225 230 235 240

Val His Arg Val Trp Arg Pro Asp Arg Glu Gly Pro Gly Leu Ala Met
245 250 255

Ser Arg Ala Phe Gly Asp Tyr Cys Val Lys Asp Tyr Gly Val Ile Ser
260 265 270

Ala Pro Glu Val Thr His Arg Arg Ile Thr Ala Gln Asp His Phe Val
275 280 285

Ile Leu Ala Thr Asp Gly Asp Lys His Leu Asn Leu Phe Val Phe Val
290 295 300

Cys Ala Ala Gly Val Gly Arg Gly Val Glu Arg Gly Gly Gly Ala Asp
305 310 315 320

Arg Gly Val Gly Ala Gly Glu Gly Glu Gly Gly Glu Ala Ala Arg Arg
325 330 335

Val Arg Arg Pro Gly Met Glu Ala Gln Ala Pro Gly His Arg Arg Arg
340 345 350

Arg Leu Leu Gly Asp Leu Pro Leu Leu Pro Leu Ala Ala Val Leu Asn
355 360 365

Asn Thr His Ala Asp Thr His Ala Ala Asn Lys Asn Arg Thr Arg Arg
370 375 380

Arg Gln Cys Arg Arg Arg Arg
385 390

<210> SEQ ID NO 8
<211> LENGTH: 1263
<212> TYPE: DNA
<213> ORGANISM: Oryza sativa
<220> FEATURE:
<221> NAME/KEY: CDS
<222> LOCATION: (1)..(1263)

<400> SEQUENCE: 8 atg ggg ata tgc tgc agc aag ggg aag gag gag ctt gag gag gag gga 48
Met Gly Ile Cys Cys Ser Lys Gly Lys Glu Glu Leu Glu Glu Glu Gly
1 5 10 15 ttt cca tgg aag cac gac gcc ttc ttc cac gac cag ctt tgg agc gct 96
Phe Pro Trp Lys His Asp Ala Phe Phe His Asp Gln Leu Trp Ser Ala
20 25 30 ggc gtc tcc atg cac acc aag caa ggc tgg aag ggc gcc aac cag gac 144

-continued

```
Gly Val Ser Met His Thr Lys Gln Gly Trp Lys Gly Ala Asn Gln Asp
        35                  40                  45

gcc atg act acc tgc cag gac ttt gcg ggg cac aag ggc cag ata ttt      192
Ala Met Thr Thr Cys Gln Asp Phe Ala Gly His Lys Gly Gln Ile Phe
    50                  55                  60

tgt gga gtt ttt gat ggg cat ggc cct ctc gga agg gaa gtt gct cgc      240
Cys Gly Val Phe Asp Gly His Gly Pro Leu Gly Arg Glu Val Ala Arg
65                  70                  75                  80

cat gtc cgc gac gtc ctt cca gtg aaa cta tcc tcc tct ttg gca ctg      288
His Val Arg Asp Val Leu Pro Val Lys Leu Ser Ser Ser Leu Ala Leu
                85                  90                  95

aag act gaa caa gat cca tcc agc aac aca gat aag gaa acc ttg gaa      336
Lys Thr Glu Gln Asp Pro Ser Ser Asn Thr Asp Lys Glu Thr Leu Glu
            100                 105                 110

aag tca gat tgc acc tca ttg agc gat aca agc aat gag aag caa ttg      384
Lys Ser Asp Cys Thr Ser Leu Ser Asp Thr Ser Asn Glu Lys Gln Leu
        115                 120                 125

tta tcc acc tgg aag aac ata ttt gtc aag aca ttt gag gat gtt gat      432
Leu Ser Thr Trp Lys Asn Ile Phe Val Lys Thr Phe Glu Asp Val Asp
    130                 135                 140

gag gat ctg agg caa cat tct gga att gac tgc att tgt agt ggc aca      480
Glu Asp Leu Arg Gln His Ser Gly Ile Asp Cys Ile Cys Ser Gly Thr
145                 150                 155                 160

act gct gtc act gtc gtt agg cag ggt gat cac ctg atc att gca aat      528
Thr Ala Val Thr Val Val Arg Gln Gly Asp His Leu Ile Ile Ala Asn
                165                 170                 175

ttg ggc gat tca cgt gcg gtt ctt tgc acc cga gac agc aag gac cgc      576
Leu Gly Asp Ser Arg Ala Val Leu Cys Thr Arg Asp Ser Lys Asp Arg
            180                 185                 190

cca att tca gtc caa cta acc act gac ctg aaa cca aat ctt cca agc      624
Pro Ile Ser Val Gln Leu Thr Thr Asp Leu Lys Pro Asn Leu Pro Ser
        195                 200                 205

gaa gct gag aga atc ctg aat tcc aag ggg cgg gtt ttc gcc atg gac      672
Glu Ala Glu Arg Ile Leu Asn Ser Lys Gly Arg Val Phe Ala Met Asp
    210                 215                 220

gat gag ccg gac gtg cct agg atg tgg cta cca gac caa gac gcg ccg      720
Asp Glu Pro Asp Val Pro Arg Met Trp Leu Pro Asp Gln Asp Ala Pro
225                 230                 235                 240

ggc ctc gcc atg gca agg gca ttt gga gat ttc tgc ttg aag agt cat      768
Gly Leu Ala Met Ala Arg Ala Phe Gly Asp Phe Cys Leu Lys Ser His
                245                 250                 255

gga cta atc tgt aca cca gaa gtc tac tac agg aag cta tct gca aaa      816
Gly Leu Ile Cys Thr Pro Glu Val Tyr Tyr Arg Lys Leu Ser Ala Lys
            260                 265                 270

gat gac ttc ttg gta ctt gct act gac ggg ata tgg gac gtg ctg tcg      864
Asp Asp Phe Leu Val Leu Ala Thr Asp Gly Ile Trp Asp Val Leu Ser
        275                 280                 285

aac aag gag gtg atc aag atc gta tcg tcg gct act gac cat tcc aag      912
Asn Lys Glu Val Ile Lys Ile Val Ser Ser Ala Thr Asp His Ser Lys
    290                 295                 300

gcc gcc aag cag ctc gtc gag cgg gcg gtg cgc acg tgg cgg cgc aag      960
Ala Ala Lys Gln Leu Val Glu Arg Ala Val Arg Thr Trp Arg Arg Lys
305                 310                 315                 320

ttc ccg acg tcg atg gtc gac gac tgc gcc gtg gtg tgc ctc ttc ttg     1008
Phe Pro Thr Ser Met Val Asp Asp Cys Ala Val Val Cys Leu Phe Leu
                325                 330                 335

aag cct tca ccg tcg tcg tcg gag agc acc ccc ggg gac gcg aaa cct     1056
Lys Pro Ser Pro Ser Ser Ser Glu Ser Thr Pro Gly Asp Ala Lys Pro
            340                 345                 350
```

-continued

```
cct cag gcc gtg tcg ttc acg ggc agc ttc cga aag gtc ctg ggc ggc      1104
Pro Gln Ala Val Ser Phe Thr Gly Ser Phe Arg Lys Val Leu Gly Gly
        355                 360                 365

ggc ggc ggc gag gcg gag gag ggg acg aat gta tgg aga gct ctg gag      1152
Gly Gly Gly Glu Ala Glu Glu Gly Thr Asn Val Trp Arg Ala Leu Glu
    370                 375                 380

ggg gtg gct cgg gtg aac tcg gtg gtg agg ctg ccg cgg atg ggc gcc      1200
Gly Val Ala Arg Val Asn Ser Val Val Arg Leu Pro Arg Met Gly Ala
385                 390                 395                 400

gtg ctg agc tgg cgg cgg cgg tcg acg tcg ctg gag gaa gac gac gag      1248
Val Leu Ser Trp Arg Arg Arg Ser Thr Ser Leu Glu Glu Asp Asp Glu
                405                 410                 415

gcg agg att gat tga                                                  1263
Ala Arg Ile Asp
            420


<210> SEQ ID NO 9
<211> LENGTH: 420
<212> TYPE: PRT
<213> ORGANISM: Oryza sativa

<400> SEQUENCE: 9

Met Gly Ile Cys Cys Ser Lys Gly Lys Glu Glu Leu Glu Glu Glu Gly
1               5                   10                  15

Phe Pro Trp Lys His Asp Ala Phe Phe His Asp Gln Leu Trp Ser Ala
            20                  25                  30

Gly Val Ser Met His Thr Lys Gln Gly Trp Lys Gly Ala Asn Gln Asp
        35                  40                  45

Ala Met Thr Thr Cys Gln Asp Phe Ala Gly His Lys Gly Gln Ile Phe
    50                  55                  60

Cys Gly Val Phe Asp Gly His Gly Pro Leu Gly Arg Glu Val Ala Arg
65                  70                  75                  80

His Val Arg Asp Val Leu Pro Val Lys Leu Ser Ser Ser Leu Ala Leu
                85                  90                  95

Lys Thr Glu Gln Asp Pro Ser Ser Asn Thr Asp Lys Glu Thr Leu Glu
            100                 105                 110

Lys Ser Asp Cys Thr Ser Leu Ser Asp Thr Ser Asn Glu Lys Gln Leu
        115                 120                 125

Leu Ser Thr Trp Lys Asn Ile Phe Val Lys Thr Phe Glu Asp Val Asp
    130                 135                 140

Glu Asp Leu Arg Gln His Ser Gly Ile Asp Cys Ile Cys Ser Gly Thr
145                 150                 155                 160

Thr Ala Val Thr Val Val Arg Gln Gly Asp His Leu Ile Ile Ala Asn
                165                 170                 175

Leu Gly Asp Ser Arg Ala Val Leu Cys Thr Arg Asp Ser Lys Asp Arg
            180                 185                 190

Pro Ile Ser Val Gln Leu Thr Thr Asp Leu Lys Pro Asn Leu Pro Ser
        195                 200                 205

Glu Ala Glu Arg Ile Leu Asn Ser Lys Gly Arg Val Phe Ala Met Asp
    210                 215                 220

Asp Glu Pro Asp Val Pro Arg Met Trp Leu Pro Asp Gln Asp Ala Pro
225                 230                 235                 240

Gly Leu Ala Met Ala Arg Ala Phe Gly Asp Phe Cys Leu Lys Ser His
                245                 250                 255

Gly Leu Ile Cys Thr Pro Glu Val Tyr Tyr Arg Lys Leu Ser Ala Lys
            260                 265                 270
```

-continued

```
Asp Asp Phe Leu Val Leu Ala Thr Asp Gly Ile Trp Asp Val Leu Ser
        275                 280                 285

Asn Lys Glu Val Ile Lys Ile Val Ser Ser Ala Thr Asp His Ser Lys
    290                 295                 300

Ala Ala Lys Gln Leu Val Glu Arg Ala Val Arg Thr Trp Arg Arg Lys
305                 310                 315                 320

Phe Pro Thr Ser Met Val Asp Asp Cys Ala Val Val Cys Leu Phe Leu
                325                 330                 335

Lys Pro Ser Pro Ser Ser Ser Glu Ser Thr Pro Gly Asp Ala Lys Pro
            340                 345                 350

Pro Gln Ala Val Ser Phe Thr Gly Ser Phe Arg Lys Val Leu Gly Gly
        355                 360                 365

Gly Gly Gly Glu Ala Glu Glu Gly Thr Asn Val Trp Arg Ala Leu Glu
    370                 375                 380

Gly Val Ala Arg Val Asn Ser Val Val Arg Leu Pro Arg Met Gly Ala
385                 390                 395                 400

Val Leu Ser Trp Arg Arg Arg Ser Thr Ser Leu Glu Glu Asp Asp Glu
                405                 410                 415

Ala Arg Ile Asp
            420


<210> SEQ ID NO 10
<211> LENGTH: 1632
<212> TYPE: DNA
<213> ORGANISM: Oryza sativa
<220> FEATURE:
<221> NAME/KEY: CDS
<222> LOCATION: (1)..(1632)

<400> SEQUENCE: 10

atg gat ggg gtg cct gat gcc caa cgc aca aca tca cca tca atg ata       48
Met Asp Gly Val Pro Asp Ala Gln Arg Thr Thr Ser Pro Ser Met Ile
1               5                   10                  15

aaa caa caa aac tac ttc aac tac ccc tac gca ttc aac tcc att cta       96
Lys Gln Gln Asn Tyr Phe Asn Tyr Pro Tyr Ala Phe Asn Ser Ile Leu
            20                  25                  30

ctc tct acc ccc tcc ttc ctt cct tcc ttc ctt cct agc tac ctc tac      144
Leu Ser Thr Pro Ser Phe Leu Pro Ser Phe Leu Pro Ser Tyr Leu Tyr
        35                  40                  45

gaa gta cca gca gca gaa gaa gca atg ggg atc tgc tgc agc aag ggg      192
Glu Val Pro Ala Ala Glu Glu Ala Met Gly Ile Cys Cys Ser Lys Gly
    50                  55                  60

aag gag gag ctt gag gag gga ttt cca tgg aag cac gac gcc ttc ttc      240
Lys Glu Glu Leu Glu Glu Gly Phe Pro Trp Lys His Asp Ala Phe Phe
65                  70                  75                  80

cac gac cag ctt tgg agc gct ggc gtc tcc atg cac acc aag caa ggc      288
His Asp Gln Leu Trp Ser Ala Gly Val Ser Met His Thr Lys Gln Gly
                85                  90                  95

tgg aag ggc gct aac cag gat gcc atg act acc tgc cag gac ttt gcg      336
Trp Lys Gly Ala Asn Gln Asp Ala Met Thr Thr Cys Gln Asp Phe Ala
            100                 105                 110

ggg cac aag ggc cag ata ttt tgt gga gtt ttt gat ggg cat ggc cct      384
Gly His Lys Gly Gln Ile Phe Cys Gly Val Phe Asp Gly His Gly Pro
        115                 120                 125

ctc gga agg gaa gtt gct cgc cat gtc cgc gac gtc ctt cca atg aaa      432
Leu Gly Arg Glu Val Ala Arg His Val Arg Asp Val Leu Pro Met Lys
    130                 135                 140

cta tcc tcc tct ttg gca ctg aaa act gaa caa gat cca tcc agc aac      480
Leu Ser Ser Ser Leu Ala Leu Lys Thr Glu Gln Asp Pro Ser Ser Asn
```

-continued

```
145                 150                 155                 160

aca gat aag gaa gcc ttg gaa aaa tca gat tgc acc tca ttg agc gat      528
Thr Asp Lys Glu Ala Leu Glu Lys Ser Asp Cys Thr Ser Leu Ser Asp
                165                 170                 175

aca agc aat gag aag caa ttg tta tcc acc tgg aag aac ata ttt gtc      576
Thr Ser Asn Glu Lys Gln Leu Leu Ser Thr Trp Lys Asn Ile Phe Val
            180                 185                 190

aag aca ttt gag gat gta gat gat gat ctg aga caa aat tct gga att      624
Lys Thr Phe Glu Asp Val Asp Asp Asp Leu Arg Gln Asn Ser Gly Ile
        195                 200                 205

gac tgc att tgt agt ggc aca act gct gtc act gtc gtc agg cag ggt      672
Asp Cys Ile Cys Ser Gly Thr Thr Ala Val Thr Val Val Arg Gln Gly
    210                 215                 220

gat cac ctg atc att gca aat ttg ggc gat tca cgt gcg gtt ctt tgc      720
Asp His Leu Ile Ile Ala Asn Leu Gly Asp Ser Arg Ala Val Leu Cys
225                 230                 235                 240

acc cga gat agc aag gac cgc cca att cca gtt caa cta acc act gac      768
Thr Arg Asp Ser Lys Asp Arg Pro Ile Pro Val Gln Leu Thr Thr Asp
                245                 250                 255

ctg aaa cca aat ctt cca agc gaa gct gag aga atc ctg aat tgt aag      816
Leu Lys Pro Asn Leu Pro Ser Glu Ala Glu Arg Ile Leu Asn Cys Lys
            260                 265                 270

ggg cgg gtt ttt gcc atg gac gac gag ccg gac gtg tct agg atg tgg      864
Gly Arg Val Phe Ala Met Asp Asp Glu Pro Asp Val Ser Arg Met Trp
        275                 280                 285

cta cca gac caa gac gcg ccg ggc ctc gcc atg gca agg gca ttt gga      912
Leu Pro Asp Gln Asp Ala Pro Gly Leu Ala Met Ala Arg Ala Phe Gly
    290                 295                 300

gat ttc tgc ttg aag agt cat gga ctt atc tgt aca cca gaa gtc tat      960
Asp Phe Cys Leu Lys Ser His Gly Leu Ile Cys Thr Pro Glu Val Tyr
305                 310                 315                 320

tac agg aag cta tcc gaa aaa gat gaa ttc ttg gta ctt gct act gac     1008
Tyr Arg Lys Leu Ser Glu Lys Asp Glu Phe Leu Val Leu Ala Thr Asp
                325                 330                 335

ggg ata tgg gac gtg cta tcg aac aag gaa gtg atc aag atc gta tcg     1056
Gly Ile Trp Asp Val Leu Ser Asn Lys Glu Val Ile Lys Ile Val Ser
            340                 345                 350

tcg gct act gac cat tcc aag gcc gcc aag cag ctg gtc gag cgg gcg     1104
Ser Ala Thr Asp His Ser Lys Ala Ala Lys Gln Leu Val Glu Arg Ala
        355                 360                 365

gtg cgc gcg tgg cgg cgc aag ttc ccg acg tca atg gtc gac gac tgc     1152
Val Arg Ala Trp Arg Arg Lys Phe Pro Thr Ser Met Val Asp Asp Cys
    370                 375                 380

gcc gtc gtc tgc ctc ttc ttg aag cct tct ccg tcg tcg gag gag agc     1200
Ala Val Val Cys Leu Phe Leu Lys Pro Ser Pro Ser Ser Glu Glu Ser
385                 390                 395                 400

acc cat gta gac gcg aag gcg cct cag gtc gtg tcg ttc acg ggc agc     1248
Thr His Val Asp Ala Lys Ala Pro Gln Val Val Ser Phe Thr Gly Ser
                405                 410                 415

ttc cgc aag gcc ctg ggt ggt ggc ggc ggc ggc gag gcg gag gag gtg     1296
Phe Arg Lys Ala Leu Gly Gly Gly Gly Gly Gly Glu Ala Glu Glu Val
            420                 425                 430

gaa aag att tat cga cga agt atc cgc act gtc aca cgg gac att tgg     1344
Glu Lys Ile Tyr Arg Arg Ser Ile Arg Thr Val Thr Arg Asp Ile Trp
        435                 440                 445

gac aaa gta tct gca aga ctc gac tgt gat cac ata tcc acg acg cac     1392
Asp Lys Val Ser Ala Arg Leu Asp Cys Asp His Ile Ser Thr Thr His
    450                 455                 460

aac cca gat gaa acg ctg ctt gat tgg tgg gaa aga aga aca gag caa     1440
```

```
Asn Pro Asp Glu Thr Leu Leu Asp Trp Trp Glu Arg Arg Thr Glu Gln
465                 470                 475                 480

aat gac aag gac aag acg aag gga acg cgc tcc att cac atg ctc ctt     1488
Asn Asp Lys Asp Lys Thr Lys Gly Thr Arg Ser Ile His Met Leu Leu
                485                 490                 495

agc tgg gaa atc tgg tgt gaa agg aat agg cgc gtt ttc agg aat aag     1536
Ser Trp Glu Ile Trp Cys Glu Arg Asn Arg Arg Val Phe Arg Asn Lys
            500                 505                 510

gag ctc gct atc tca caa ttg gtg acc aaa atc ctt gat gaa atc aat     1584
Glu Leu Ala Ile Ser Gln Leu Val Thr Lys Ile Leu Asp Glu Ile Asn
        515                 520                 525

gtc tgg att gca tgc ggg gcg aag aat tta gcg aga ata gtg ttg taa     1632
Val Trp Ile Ala Cys Gly Ala Lys Asn Leu Ala Arg Ile Val Leu
    530                 535                 540


<210> SEQ ID NO 11
<211> LENGTH: 543
<212> TYPE: PRT
<213> ORGANISM: Oryza sativa

<400> SEQUENCE: 11

Met Asp Gly Val Pro Asp Ala Gln Arg Thr Thr Ser Pro Ser Met Ile
1               5                   10                  15

Lys Gln Gln Asn Tyr Phe Asn Tyr Pro Tyr Ala Phe Asn Ser Ile Leu
            20                  25                  30

Leu Ser Thr Pro Ser Phe Leu Pro Ser Phe Leu Pro Ser Tyr Leu Tyr
        35                  40                  45

Glu Val Pro Ala Ala Glu Glu Ala Met Gly Ile Cys Cys Ser Lys Gly
    50                  55                  60

Lys Glu Glu Leu Glu Glu Gly Phe Pro Trp Lys His Asp Ala Phe Phe
65                  70                  75                  80

His Asp Gln Leu Trp Ser Ala Gly Val Ser Met His Thr Lys Gln Gly
                85                  90                  95

Trp Lys Gly Ala Asn Gln Asp Ala Met Thr Thr Cys Gln Asp Phe Ala
            100                 105                 110

Gly His Lys Gly Gln Ile Phe Cys Gly Val Phe Asp Gly His Gly Pro
        115                 120                 125

Leu Gly Arg Glu Val Ala Arg His Val Arg Asp Val Leu Pro Met Lys
    130                 135                 140

Leu Ser Ser Ser Leu Ala Leu Lys Thr Glu Gln Asp Pro Ser Ser Asn
145                 150                 155                 160

Thr Asp Lys Glu Ala Leu Glu Lys Ser Asp Cys Thr Ser Leu Ser Asp
                165                 170                 175

Thr Ser Asn Glu Lys Gln Leu Leu Ser Thr Trp Lys Asn Ile Phe Val
            180                 185                 190

Lys Thr Phe Glu Asp Val Asp Asp Asp Leu Arg Gln Asn Ser Gly Ile
        195                 200                 205

Asp Cys Ile Cys Ser Gly Thr Thr Ala Val Thr Val Val Arg Gln Gly
    210                 215                 220

Asp His Leu Ile Ile Ala Asn Leu Gly Asp Ser Arg Ala Val Leu Cys
225                 230                 235                 240

Thr Arg Asp Ser Lys Asp Arg Pro Ile Pro Val Gln Leu Thr Thr Asp
                245                 250                 255

Leu Lys Pro Asn Leu Pro Ser Glu Ala Glu Arg Ile Leu Asn Cys Lys
            260                 265                 270

Gly Arg Val Phe Ala Met Asp Asp Glu Pro Asp Val Ser Arg Met Trp
```

```
        275                 280                 285

Leu Pro Asp Gln Asp Ala Pro Gly Leu Ala Met Ala Arg Ala Phe Gly
    290                 295                 300

Asp Phe Cys Leu Lys Ser His Gly Leu Ile Cys Thr Pro Glu Val Tyr
305                 310                 315                 320

Tyr Arg Lys Leu Ser Glu Lys Asp Glu Phe Leu Val Leu Ala Thr Asp
                325                 330                 335

Gly Ile Trp Asp Val Leu Ser Asn Lys Glu Val Ile Lys Ile Val Ser
            340                 345                 350

Ser Ala Thr Asp His Ser Lys Ala Ala Lys Gln Leu Val Glu Arg Ala
        355                 360                 365

Val Arg Ala Trp Arg Arg Lys Phe Pro Thr Ser Met Val Asp Asp Cys
    370                 375                 380

Ala Val Val Cys Leu Phe Leu Lys Pro Ser Pro Ser Ser Glu Glu Ser
385                 390                 395                 400

Thr His Val Asp Ala Lys Ala Pro Gln Val Val Ser Phe Thr Gly Ser
                405                 410                 415

Phe Arg Lys Ala Leu Gly Gly Gly Gly Gly Gly Glu Ala Glu Glu Val
            420                 425                 430

Glu Lys Ile Tyr Arg Arg Ser Ile Arg Thr Val Thr Arg Asp Ile Trp
        435                 440                 445

Asp Lys Val Ser Ala Arg Leu Asp Cys Asp His Ile Ser Thr Thr His
    450                 455                 460

Asn Pro Asp Glu Thr Leu Leu Asp Trp Trp Glu Arg Arg Thr Glu Gln
465                 470                 475                 480

Asn Asp Lys Asp Lys Thr Lys Gly Thr Arg Ser Ile His Met Leu Leu
                485                 490                 495

Ser Trp Glu Ile Trp Cys Glu Arg Asn Arg Arg Val Phe Arg Asn Lys
            500                 505                 510

Glu Leu Ala Ile Ser Gln Leu Val Thr Lys Ile Leu Asp Glu Ile Asn
        515                 520                 525

Val Trp Ile Ala Cys Gly Ala Lys Asn Leu Ala Arg Ile Val Leu
    530                 535                 540


<210> SEQ ID NO 12
<211> LENGTH: 1557
<212> TYPE: DNA
<213> ORGANISM: Oryza sativa
<220> FEATURE:
<221> NAME/KEY: CDS
<222> LOCATION: (1)..(1557)

<400> SEQUENCE: 12

atg gtg gag gcc gcc gcg ggg cgc cgg tcg ggg gcc aac cgt cgg cgg       48
Met Val Glu Ala Ala Ala Gly Arg Arg Ser Gly Ala Asn Arg Arg Arg
1               5                   10                  15

cct agc ggc ggg ggc gag cgg cgg cgg cag cag cag cag cac cag cgc       96
Pro Ser Gly Gly Gly Glu Arg Arg Arg Gln Gln Gln Gln His Gln Arg
            20                  25                  30

ctc gtc gcg gtc gcg gtg gcc gcg cgc gtc gtc atg gtg gcg ccc gcg      144
Leu Val Ala Val Ala Val Ala Ala Arg Val Val Met Val Ala Pro Ala
        35                  40                  45

gcc acg ccc gcg ccc gcg gcg ggg ggt ggc ggg ggc tgc gtc gag gac      192
Ala Thr Pro Ala Pro Ala Ala Gly Gly Gly Gly Gly Cys Val Glu Asp
    50                  55                  60

atc ctc ggg tgc ctc ctc ggc gtg ctg cgc gcg ctc ggc gtc acg tgg      240
Ile Leu Gly Cys Leu Leu Gly Val Leu Arg Ala Leu Gly Val Thr Trp
```

-continued

```
65                  70                  75                  80

gcg gcg gcg gcg agg ccg cag agg cag cag ccg cgc ctg gcg gcg cag      288
Ala Ala Ala Ala Arg Pro Gln Arg Gln Gln Pro Arg Leu Ala Ala Gln
                85                  90                  95

acg ccg cga ggg ccc gcg cct ggg gcg gat ggg cgc cgc gcc gcc gcc      336
Thr Pro Arg Gly Pro Ala Pro Gly Ala Asp Gly Arg Arg Ala Ala Ala
            100                 105                 110

gag ctg agg ggg atc ccc ggc cgg atc gcg ggg aac ggg gcc tgc gcc      384
Glu Leu Arg Gly Ile Pro Gly Arg Ile Ala Gly Asn Gly Ala Cys Ala
        115                 120                 125

gtc gcg tcg ctc tac acg ctg cag ggg aag aaa ggc gtc aac caa gac      432
Val Ala Ser Leu Tyr Thr Leu Gln Gly Lys Lys Gly Val Asn Gln Asp
    130                 135                 140

gcc atg atc gtc tgg gag aat ttc tgt tca aga gag gat acc att ttt      480
Ala Met Ile Val Trp Glu Asn Phe Cys Ser Arg Glu Asp Thr Ile Phe
145                 150                 155                 160

tgt ggt gtt ttt gat ggc cat gga cca aac ggc cat ttg gtt gct aag      528
Cys Gly Val Phe Asp Gly His Gly Pro Asn Gly His Leu Val Ala Lys
                165                 170                 175

agg gtg aga gat ctt ctg ccc att aag ctt ggt gcg gat ttg ggg acg      576
Arg Val Arg Asp Leu Leu Pro Ile Lys Leu Gly Ala Asp Leu Gly Thr
            180                 185                 190

gat gaa gga cga cag aca tcc act agc agc atc aaa agc aat gga gat      624
Asp Glu Gly Arg Gln Thr Ser Thr Ser Ser Ile Lys Ser Asn Gly Asp
        195                 200                 205

gaa aca gga tcc cct gga aac atg ggc aga gat gct gag cag aac gga      672
Glu Thr Gly Ser Pro Gly Asn Met Gly Arg Asp Ala Glu Gln Asn Gly
    210                 215                 220

gag tac cca gag atc ttc aca gca ttg aga act tca ttt ttg agg gcg      720
Glu Tyr Pro Glu Ile Phe Thr Ala Leu Arg Thr Ser Phe Leu Arg Ala
225                 230                 235                 240

ttc aat gtc atg gat aga gat ctc aag tta cat aaa agt ata gat tgt      768
Phe Asn Val Met Asp Arg Asp Leu Lys Leu His Lys Ser Ile Asp Cys
                245                 250                 255

ttt ttc agt gga aca aca gca gtg gca gtg ctc aag cag gga cgg aat      816
Phe Phe Ser Gly Thr Thr Ala Val Ala Val Leu Lys Gln Gly Arg Asn
            260                 265                 270

ctt ata att ggt aac ctc ggg gac tcg cgg gcc atc tta ggc aca aga      864
Leu Ile Ile Gly Asn Leu Gly Asp Ser Arg Ala Ile Leu Gly Thr Arg
        275                 280                 285

gat aaa gat aat cag ctt atg gct gtc caa ttg aca gtt gat ctc aaa      912
Asp Lys Asp Asn Gln Leu Met Ala Val Gln Leu Thr Val Asp Leu Lys
    290                 295                 300

cct aac att cca agt gaa gca cag cga atc agg caa cgc agg ggc agg      960
Pro Asn Ile Pro Ser Glu Ala Gln Arg Ile Arg Gln Arg Arg Gly Arg
305                 310                 315                 320

ata ttt gca ctt cct gag gag cca gag gtt gct cgt gtt tgg ctt ccg     1008
Ile Phe Ala Leu Pro Glu Glu Pro Glu Val Ala Arg Val Trp Leu Pro
                325                 330                 335

aag tac aac tcc cct gga ctg gcc atg gct agg gca ttt gga gac ttc     1056
Lys Tyr Asn Ser Pro Gly Leu Ala Met Ala Arg Ala Phe Gly Asp Phe
            340                 345                 350

tgt ctc aag gat tat ggt cta atc tct atg cct gaa gtc tcg tac cac     1104
Cys Leu Lys Asp Tyr Gly Leu Ile Ser Met Pro Glu Val Ser Tyr His
        355                 360                 365

cgt atc aca gaa aag gat gag ttt gtt gta ttg gct act gat ggg gtt     1152
Arg Ile Thr Glu Lys Asp Glu Phe Val Val Leu Ala Thr Asp Gly Val
    370                 375                 380

tgg gat gtg ctg tca aac act gaa gtt gtt agt att gtc aac aga gct     1200
```

-continued

```
Trp Asp Val Leu Ser Asn Thr Glu Val Val Ser Ile Val Asn Arg Ala
385                 390                 395                 400

act tct cgg gcc tct gca gca cga ttg cta gtc gaa tca gct cac cgt      1248
Thr Ser Arg Ala Ser Ala Ala Arg Leu Leu Val Glu Ser Ala His Arg
                405                 410                 415

gcc tgg cgt gca cgt ttc ccc act tct aaa att gat gat tgt gct gtg      1296
Ala Trp Arg Ala Arg Phe Pro Thr Ser Lys Ile Asp Asp Cys Ala Val
            420                 425                 430

gtc tgc cta ttc ctg gat aca gac gaa tta agt gaa aca tcc agt tct      1344
Val Cys Leu Phe Leu Asp Thr Asp Glu Leu Ser Glu Thr Ser Ser Ser
        435                 440                 445

atg gcc cgc gat atg aca aat gct gta gaa gtt agc agt ggg cag cac      1392
Met Ala Arg Asp Met Thr Asn Ala Val Glu Val Ser Ser Gly Gln His
    450                 455                 460

tcc aat act atc caa ttg agc act gga gta tct tca gat gtt gtt act      1440
Ser Asn Thr Ile Gln Leu Ser Thr Gly Val Ser Ser Asp Val Val Thr
465                 470                 475                 480

gca gtt cta aca gat ggt gat gat ctg tct gct gtt gat gca gtt gca      1488
Ala Val Leu Thr Asp Gly Asp Asp Leu Ser Ala Val Asp Ala Val Ala
                485                 490                 495

aag ctg gtt act ctc acg gat ttg ccg aac aat gct tca ggc gca acg      1536
Lys Leu Val Thr Leu Thr Asp Leu Pro Asn Asn Ala Ser Gly Ala Thr
            500                 505                 510

caa agc atc acc acc aag tga                                          1557
Gln Ser Ile Thr Thr Lys
        515


<210> SEQ ID NO 13
<211> LENGTH: 518
<212> TYPE: PRT
<213> ORGANISM: Oryza sativa

<400> SEQUENCE: 13

Met Val Glu Ala Ala Ala Gly Arg Arg Ser Gly Ala Asn Arg Arg Arg
1               5                   10                  15

Pro Ser Gly Gly Gly Glu Arg Arg Arg Gln Gln Gln Gln His Gln Arg
            20                  25                  30

Leu Val Ala Val Ala Val Ala Ala Arg Val Val Met Val Ala Pro Ala
        35                  40                  45

Ala Thr Pro Ala Pro Ala Ala Gly Gly Gly Gly Gly Cys Val Glu Asp
    50                  55                  60

Ile Leu Gly Cys Leu Leu Gly Val Leu Arg Ala Leu Gly Val Thr Trp
65                  70                  75                  80

Ala Ala Ala Ala Arg Pro Gln Arg Gln Gln Pro Arg Leu Ala Ala Gln
                85                  90                  95

Thr Pro Arg Gly Pro Ala Pro Gly Ala Asp Gly Arg Arg Ala Ala Ala
            100                 105                 110

Glu Leu Arg Gly Ile Pro Gly Arg Ile Ala Gly Asn Gly Ala Cys Ala
        115                 120                 125

Val Ala Ser Leu Tyr Thr Leu Gln Gly Lys Lys Gly Val Asn Gln Asp
    130                 135                 140

Ala Met Ile Val Trp Glu Asn Phe Cys Ser Arg Glu Asp Thr Ile Phe
145                 150                 155                 160

Cys Gly Val Phe Asp Gly His Gly Pro Asn Gly His Leu Val Ala Lys
                165                 170                 175

Arg Val Arg Asp Leu Leu Pro Ile Lys Leu Gly Ala Asp Leu Gly Thr
            180                 185                 190
```

```
Asp Glu Gly Arg Gln Thr Ser Thr Ser Ser Ile Lys Ser Asn Gly Asp
        195                 200                 205

Glu Thr Gly Ser Pro Gly Asn Met Gly Arg Asp Ala Glu Gln Asn Gly
    210                 215                 220

Glu Tyr Pro Glu Ile Phe Thr Ala Leu Arg Thr Ser Phe Leu Arg Ala
225                 230                 235                 240

Phe Asn Val Met Asp Arg Asp Leu Lys Leu His Lys Ser Ile Asp Cys
                245                 250                 255

Phe Phe Ser Gly Thr Thr Ala Val Ala Val Leu Lys Gln Gly Arg Asn
            260                 265                 270

Leu Ile Ile Gly Asn Leu Gly Asp Ser Arg Ala Ile Leu Gly Thr Arg
        275                 280                 285

Asp Lys Asp Asn Gln Leu Met Ala Val Gln Leu Thr Val Asp Leu Lys
    290                 295                 300

Pro Asn Ile Pro Ser Glu Ala Gln Arg Ile Arg Gln Arg Arg Gly Arg
305                 310                 315                 320

Ile Phe Ala Leu Pro Glu Glu Pro Glu Val Ala Arg Val Trp Leu Pro
                325                 330                 335

Lys Tyr Asn Ser Pro Gly Leu Ala Met Ala Arg Ala Phe Gly Asp Phe
            340                 345                 350

Cys Leu Lys Asp Tyr Gly Leu Ile Ser Met Pro Glu Val Ser Tyr His
        355                 360                 365

Arg Ile Thr Glu Lys Asp Glu Phe Val Val Leu Ala Thr Asp Gly Val
    370                 375                 380

Trp Asp Val Leu Ser Asn Thr Glu Val Val Ser Ile Val Asn Arg Ala
385                 390                 395                 400

Thr Ser Arg Ala Ser Ala Ala Arg Leu Leu Val Glu Ser Ala His Arg
                405                 410                 415

Ala Trp Arg Ala Arg Phe Pro Thr Ser Lys Ile Asp Asp Cys Ala Val
            420                 425                 430

Val Cys Leu Phe Leu Asp Thr Asp Glu Leu Ser Glu Thr Ser Ser Ser
        435                 440                 445

Met Ala Arg Asp Met Thr Asn Ala Val Glu Val Ser Ser Gly Gln His
    450                 455                 460

Ser Asn Thr Ile Gln Leu Ser Thr Gly Val Ser Ser Asp Val Val Thr
465                 470                 475                 480

Ala Val Leu Thr Asp Gly Asp Asp Leu Ser Ala Val Asp Ala Val Ala
                485                 490                 495

Lys Leu Val Thr Leu Thr Asp Leu Pro Asn Asn Ala Ser Gly Ala Thr
            500                 505                 510

Gln Ser Ile Thr Thr Lys
        515
```

<210> SEQ ID NO 14
<211> LENGTH: 1383
<212> TYPE: DNA
<213> ORGANISM: Oryza sativa
<220> FEATURE:
<221> NAME/KEY: CDS
<222> LOCATION: (1)..(1383)

<400> SEQUENCE: 14

```
atg gtg gcg gtg acc ggg ggc agg ccc ccc ggc ctg cag gat gcg ccg       48
Met Val Ala Val Thr Gly Gly Arg Pro Pro Gly Leu Gln Asp Ala Pro
1               5                   10                  15

ggg gca cca cca cca gca cca gca gca gag gct gtg ccg tcg cgc ccg       96
```

-continued

```
Gly Ala Pro Pro Pro Ala Pro Ala Ala Glu Ala Val Pro Ser Arg Pro
            20                  25                  30

ctc gcg cgg gac gcg act tac gga ggc cgc gtg tac ggt ggc gta gga      144
Leu Ala Arg Asp Ala Thr Tyr Gly Gly Arg Val Tyr Gly Gly Val Gly
        35                  40                  45

gga gga gga tgc tgc ctc gag ttc ctc gac tgc gtg ctc cgg gcg atg      192
Gly Gly Gly Cys Cys Leu Glu Phe Leu Asp Cys Val Leu Arg Ala Met
    50                  55                  60

ggc gtc gcc acc ccg gcc gag atc atg ccc ccc gcg gac ttc agg tgg      240
Gly Val Ala Thr Pro Ala Glu Ile Met Pro Pro Ala Asp Phe Arg Trp
65                  70                  75                  80

gcc gcg cgc ccg atg cgg cgg cgc cgc cgc ggg ggc tcc tcg tcc tcc      288
Ala Ala Arg Pro Met Arg Arg Arg Arg Arg Gly Gly Ser Ser Ser Ser
                85                  90                  95

tcc tcc tcg ccg cgc gac cgc gag ccg agg gac ggc cgg atc gcc gcc      336
Ser Ser Ser Pro Arg Asp Arg Glu Pro Arg Asp Gly Arg Ile Ala Ala
            100                 105                 110

aac ggc gcc tcc gct gcc gcc tcg ctc tac acg atg cgg ggc aac aag      384
Asn Gly Ala Ser Ala Ala Ala Ser Leu Tyr Thr Met Arg Gly Asn Lys
        115                 120                 125

ggc gtc aac cag gac gcc atg ctt gtc tgg gag aat ttc tgt tca aag      432
Gly Val Asn Gln Asp Ala Met Leu Val Trp Glu Asn Phe Cys Ser Lys
    130                 135                 140

gaa gat aca att ttt tgt ggt gtt ttt gat ggc cat gga cca tat ggc      480
Glu Asp Thr Ile Phe Cys Gly Val Phe Asp Gly His Gly Pro Tyr Gly
145                 150                 155                 160

cat ttg gtg tcc aag agg gtc aga gat ctc ctc cct ata aag ttg agt      528
His Leu Val Ser Lys Arg Val Arg Asp Leu Leu Pro Ile Lys Leu Ser
                165                 170                 175

gca aat tta gga aga gat gga cac aaa gaa act tca act aac att gtc      576
Ala Asn Leu Gly Arg Asp Gly His Lys Glu Thr Ser Thr Asn Ile Val
            180                 185                 190

aca agc agc atg act gaa ggt ggt ggc acc gaa cgc atg gat aga gat      624
Thr Ser Ser Met Thr Glu Gly Gly Gly Thr Glu Arg Met Asp Arg Asp
        195                 200                 205

act gaa act ccc ctg gga acg gag gag aat gga gac tac ccc gag atg      672
Thr Glu Thr Pro Leu Gly Thr Glu Glu Asn Gly Asp Tyr Pro Glu Met
    210                 215                 220

ttt gct gca tta aga act tca tta tta agg gca ttt tat gta atg gac      720
Phe Ala Ala Leu Arg Thr Ser Leu Leu Arg Ala Phe Tyr Val Met Asp
225                 230                 235                 240

agg gat ctt aag ttt cat aaa acc att gac tct gtg ttc agt ggt act      768
Arg Asp Leu Lys Phe His Lys Thr Ile Asp Ser Val Phe Ser Gly Thr
                245                 250                 255

aca gca gtc aca gtg atc aag cag gga cat gat ctc ctg att gga aac      816
Thr Ala Val Thr Val Ile Lys Gln Gly His Asp Leu Leu Ile Gly Asn
            260                 265                 270

ttg ggg gat tct aga gct gtc ttg gga act aga gat gaa tat gac cag      864
Leu Gly Asp Ser Arg Ala Val Leu Gly Thr Arg Asp Glu Tyr Asp Gln
        275                 280                 285

ttt ttt gct gta caa ttg aca gtt gac ctg aag cct acc att cca agt      912
Phe Phe Ala Val Gln Leu Thr Val Asp Leu Lys Pro Thr Ile Pro Ser
    290                 295                 300

gaa gct gca cga att agg gaa cga agt ggc aga ata ttc tct ctg cca      960
Glu Ala Ala Arg Ile Arg Glu Arg Ser Gly Arg Ile Phe Ser Leu Pro
305                 310                 315                 320

gat gag cca gat gtt gct cgt gtt tgg ctt ccg aag tac aac atg cca     1008
Asp Glu Pro Asp Val Ala Arg Val Trp Leu Pro Lys Tyr Asn Met Pro
                325                 330                 335
```

-continued

```
ggg ttg gcc atg gca aga gca ttt gga gac ttt tgt cta aag gat tat      1056
Gly Leu Ala Met Ala Arg Ala Phe Gly Asp Phe Cys Leu Lys Asp Tyr
            340                 345                 350

ggt cta att tct atg cct gat gtt tcc tac cac cgc atc act gaa aag      1104
Gly Leu Ile Ser Met Pro Asp Val Ser Tyr His Arg Ile Thr Glu Lys
        355                 360                 365

gat gaa ttt gtt gtg ttg gca act gat ggg gtg tgg gat gta ctt tcc      1152
Asp Glu Phe Val Val Leu Ala Thr Asp Gly Val Trp Asp Val Leu Ser
    370                 375                 380

aac tca gaa gtt gtt agc att gtc agc caa gcc aag tca gaa gcc tca      1200
Asn Ser Glu Val Val Ser Ile Val Ser Gln Ala Lys Ser Glu Ala Ser
385                 390                 395                 400

gcg gca cga ttt gtt gtt gaa tcg gct caa cgt gca tgg aga aca cgg      1248
Ala Ala Arg Phe Val Val Glu Ser Ala Gln Arg Ala Trp Arg Thr Arg
                405                 410                 415

ttc ccc aca tca aaa att gat gac tgc gct gtt gtc tgc ctg ttc ttg      1296
Phe Pro Thr Ser Lys Ile Asp Asp Cys Ala Val Val Cys Leu Phe Leu
            420                 425                 430

aat aca gat gct aga aat aaa ccc ccc ggt tca gga atc aaa gat ttg      1344
Asn Thr Asp Ala Arg Asn Lys Pro Pro Gly Ser Gly Ile Lys Asp Leu
        435                 440                 445

gcc aat gcc ata gaa ctg ggt ggt ggt aat ctt tct tga                  1383
Ala Asn Ala Ile Glu Leu Gly Gly Gly Asn Leu Ser
    450                 455                 460


<210> SEQ ID NO 15
<211> LENGTH: 460
<212> TYPE: PRT
<213> ORGANISM: Oryza sativa

<400> SEQUENCE: 15

Met Val Ala Val Thr Gly Gly Arg Pro Pro Gly Leu Gln Asp Ala Pro
1               5                   10                  15

Gly Ala Pro Pro Pro Ala Pro Ala Ala Glu Ala Val Pro Ser Arg Pro
            20                  25                  30

Leu Ala Arg Asp Ala Thr Tyr Gly Gly Arg Val Tyr Gly Gly Val Gly
        35                  40                  45

Gly Gly Gly Cys Cys Leu Glu Phe Leu Asp Cys Val Leu Arg Ala Met
    50                  55                  60

Gly Val Ala Thr Pro Ala Glu Ile Met Pro Pro Ala Asp Phe Arg Trp
65                  70                  75                  80

Ala Ala Arg Pro Met Arg Arg Arg Arg Arg Gly Gly Ser Ser Ser Ser
                85                  90                  95

Ser Ser Ser Pro Arg Asp Arg Glu Pro Arg Asp Gly Arg Ile Ala Ala
            100                 105                 110

Asn Gly Ala Ser Ala Ala Ala Ser Leu Tyr Thr Met Arg Gly Asn Lys
        115                 120                 125

Gly Val Asn Gln Asp Ala Met Leu Val Trp Glu Asn Phe Cys Ser Lys
    130                 135                 140

Glu Asp Thr Ile Phe Cys Gly Val Phe Asp Gly His Gly Pro Tyr Gly
145                 150                 155                 160

His Leu Val Ser Lys Arg Val Arg Asp Leu Leu Pro Ile Lys Leu Ser
                165                 170                 175

Ala Asn Leu Gly Arg Asp Gly His Lys Glu Thr Ser Thr Asn Ile Val
            180                 185                 190

Thr Ser Ser Met Thr Glu Gly Gly Gly Thr Glu Arg Met Asp Arg Asp
        195                 200                 205
```

```
Thr Glu Thr Pro Leu Gly Thr Glu Glu Asn Gly Asp Tyr Pro Glu Met
    210                 215                 220

Phe Ala Ala Leu Arg Thr Ser Leu Leu Arg Ala Phe Tyr Val Met Asp
225                 230                 235                 240

Arg Asp Leu Lys Phe His Lys Thr Ile Asp Ser Val Phe Ser Gly Thr
                245                 250                 255

Thr Ala Val Thr Val Ile Lys Gln Gly His Asp Leu Leu Ile Gly Asn
            260                 265                 270

Leu Gly Asp Ser Arg Ala Val Leu Gly Thr Arg Asp Glu Tyr Asp Gln
        275                 280                 285

Phe Phe Ala Val Gln Leu Thr Val Asp Leu Lys Pro Thr Ile Pro Ser
    290                 295                 300

Glu Ala Ala Arg Ile Arg Glu Arg Ser Gly Arg Ile Phe Ser Leu Pro
305                 310                 315                 320

Asp Glu Pro Asp Val Ala Arg Val Trp Leu Pro Lys Tyr Asn Met Pro
                325                 330                 335

Gly Leu Ala Met Ala Arg Ala Phe Gly Asp Phe Cys Leu Lys Asp Tyr
            340                 345                 350

Gly Leu Ile Ser Met Pro Asp Val Ser Tyr His Arg Ile Thr Glu Lys
        355                 360                 365

Asp Glu Phe Val Val Leu Ala Thr Asp Gly Val Trp Asp Val Leu Ser
    370                 375                 380

Asn Ser Glu Val Val Ser Ile Val Ser Gln Ala Lys Ser Glu Ala Ser
385                 390                 395                 400

Ala Ala Arg Phe Val Val Glu Ser Ala Gln Arg Ala Trp Arg Thr Arg
                405                 410                 415

Phe Pro Thr Ser Lys Ile Asp Asp Cys Ala Val Val Cys Leu Phe Leu
            420                 425                 430

Asn Thr Asp Ala Arg Asn Lys Pro Pro Gly Ser Gly Ile Lys Asp Leu
        435                 440                 445

Ala Asn Ala Ile Glu Leu Gly Gly Gly Asn Leu Ser
    450                 455                 460


<210> SEQ ID NO 16
<211> LENGTH: 1299
<212> TYPE: DNA
<213> ORGANISM: Oryza sativa
<220> FEATURE:
<221> NAME/KEY: CDS
<222> LOCATION: (1)..(1299)

<400> SEQUENCE: 16

atg ggg aca tgc ctt acg acg gcg gag cag cgg gcc atg gag gtg ccg       48
Met Gly Thr Cys Leu Thr Thr Ala Glu Gln Arg Ala Met Glu Val Pro
1               5                   10                  15

gct gcg tcg gtg aag gga gga ggg ggc agg agg agt gac gag gag gcg       96
Ala Ala Ser Val Lys Gly Gly Gly Gly Arg Arg Ser Asp Glu Glu Ala
            20                  25                  30

ccc ggc agg atc gcg ggt aac ggc gcg ggg aat gtg gcc tgc ctg ttc      144
Pro Gly Arg Ile Ala Gly Asn Gly Ala Gly Asn Val Ala Cys Leu Phe
        35                  40                  45

act cgg cag ggg aag aag ggc acc aac cag gat gcc atg gtc gcg tgg      192
Thr Arg Gln Gly Lys Lys Gly Thr Asn Gln Asp Ala Met Val Ala Trp
    50                  55                  60

gag aac tat aac gga aga tca gac acg gta ttt tgt gga gtt ttt gat      240
Glu Asn Tyr Asn Gly Arg Ser Asp Thr Val Phe Cys Gly Val Phe Asp
65                  70                  75                  80
```

-continued

```
ggc cac ggt cca cat ggc cat ctc att gct agg aaa gta aga gat att      288
Gly His Gly Pro His Gly His Leu Ile Ala Arg Lys Val Arg Asp Ile
                85                  90                  95

ctc cct tcg aga ctc tgt gat ttg ata tat gaa gac tgt ggg gat agt      336
Leu Pro Ser Arg Leu Cys Asp Leu Ile Tyr Glu Asp Cys Gly Asp Ser
            100                 105                 110

cca acc agc aat tca gat gtc tca act ctg gaa gag aat tta tct ccg      384
Pro Thr Ser Asn Ser Asp Val Ser Thr Leu Glu Glu Asn Leu Ser Pro
        115                 120                 125

tat gca gat gca gag tgc aga tct ccc aca ttg gct gga caa aaa gaa      432
Tyr Ala Asp Ala Glu Cys Arg Ser Pro Thr Leu Ala Gly Gln Lys Glu
    130                 135                 140

cat caa gaa ttc ttc aac gca atg aaa gaa tct ttc aga aag gct ttt      480
His Gln Glu Phe Phe Asn Ala Met Lys Glu Ser Phe Arg Lys Ala Phe
145                 150                 155                 160

aaa aat gtg gat aag gag ctc aaa tta caa cgg aac att gat agc att      528
Lys Asn Val Asp Lys Glu Leu Lys Leu Gln Arg Asn Ile Asp Ser Ile
                165                 170                 175

tgc agt gga act act gca gtt act tta atc aag caa ggt cat gat ctt      576
Cys Ser Gly Thr Thr Ala Val Thr Leu Ile Lys Gln Gly His Asp Leu
            180                 185                 190

att gtt ggg aat cta ggt gac tct aga gct gta tta ggc acc aga gat      624
Ile Val Gly Asn Leu Gly Asp Ser Arg Ala Val Leu Gly Thr Arg Asp
        195                 200                 205

cag aac gat aag ttg gtt gct cat cag ttg act gtt gac ctg aaa cct      672
Gln Asn Asp Lys Leu Val Ala His Gln Leu Thr Val Asp Leu Lys Pro
    210                 215                 220

gat cat cca agg gag gct agg agg atc aga cgg tgt aat ggg agg gtc      720
Asp His Pro Arg Glu Ala Arg Arg Ile Arg Arg Cys Asn Gly Arg Val
225                 230                 235                 240

ttt gct cat cag gat gaa cca gat gtg gct cgc ctt tgg ctt cct aat      768
Phe Ala His Gln Asp Glu Pro Asp Val Ala Arg Leu Trp Leu Pro Asn
                245                 250                 255

tgc aac tct cct gga ctg gca atg gcc cga gct ttt ggt gac ttt tgt      816
Cys Asn Ser Pro Gly Leu Ala Met Ala Arg Ala Phe Gly Asp Phe Cys
            260                 265                 270

cta aag gat ttt ggg ttg atc tca gta cct gat gtc acc tat agg caa      864
Leu Lys Asp Phe Gly Leu Ile Ser Val Pro Asp Val Thr Tyr Arg Gln
        275                 280                 285

att act gaa aaa gac gag ttt att gtc ctg gcg aca gat ggg gtg tgg      912
Ile Thr Glu Lys Asp Glu Phe Ile Val Leu Ala Thr Asp Gly Val Trp
    290                 295                 300

gat gtt ctc tcc aac cag gaa gtg gtg gat gtt gtt gcc tca tgc tct      960
Asp Val Leu Ser Asn Gln Glu Val Val Asp Val Val Ala Ser Cys Ser
305                 310                 315                 320

ggt cgt ttc gct gca gct cgt tct gtt gtt gat tta gca aat gag act     1008
Gly Arg Phe Ala Ala Ala Arg Ser Val Val Asp Leu Ala Asn Glu Thr
                325                 330                 335

tgg agg ttc aaa tac cca acc tca aaa act gat gat tgt gca gtg gtc     1056
Trp Arg Phe Lys Tyr Pro Thr Ser Lys Thr Asp Asp Cys Ala Val Val
            340                 345                 350

tgt ctt ttc ctg aac aag tat gaa gtt acc ggt ggt tta tca ggg caa     1104
Cys Leu Phe Leu Asn Lys Tyr Glu Val Thr Gly Gly Leu Ser Gly Gln
        355                 360                 365

cct gga tat agt cca agg atg cct gcc cta tca ggt att acc cgg ccc     1152
Pro Gly Tyr Ser Pro Arg Met Pro Ala Leu Ser Gly Ile Thr Arg Pro
    370                 375                 380

aat agt aaa agg gtt act cct gac gac gtc gat gat ggt agt gac tca     1200
Asn Ser Lys Arg Val Thr Pro Asp Asp Val Asp Asp Gly Ser Asp Ser
385                 390                 395                 400
```

```
aac gta agc gga gat gag agg tcc ttg gat ggt ttc act cga ttg aac      1248
Asn Val Ser Gly Asp Glu Arg Ser Leu Asp Gly Phe Thr Arg Leu Asn
                405                 410                 415

aca ttg ttg gca cta cca aag ttt ggt gac aca agt cca act aag aaa      1296
Thr Leu Leu Ala Leu Pro Lys Phe Gly Asp Thr Ser Pro Thr Lys Lys
            420                 425                 430

tga                                                                  1299


<210> SEQ ID NO 17
<211> LENGTH: 432
<212> TYPE: PRT
<213> ORGANISM: Oryza sativa

<400> SEQUENCE: 17

Met Gly Thr Cys Leu Thr Thr Ala Glu Gln Arg Ala Met Glu Val Pro
1               5                   10                  15

Ala Ala Ser Val Lys Gly Gly Gly Gly Arg Arg Ser Asp Glu Glu Ala
            20                  25                  30

Pro Gly Arg Ile Ala Gly Asn Gly Ala Gly Asn Val Ala Cys Leu Phe
        35                  40                  45

Thr Arg Gln Gly Lys Lys Gly Thr Asn Gln Asp Ala Met Val Ala Trp
    50                  55                  60

Glu Asn Tyr Asn Gly Arg Ser Asp Thr Val Phe Cys Gly Val Phe Asp
65                  70                  75                  80

Gly His Gly Pro His Gly His Leu Ile Ala Arg Lys Val Arg Asp Ile
                85                  90                  95

Leu Pro Ser Arg Leu Cys Asp Leu Ile Tyr Glu Asp Cys Gly Asp Ser
            100                 105                 110

Pro Thr Ser Asn Ser Asp Val Ser Thr Leu Glu Glu Asn Leu Ser Pro
        115                 120                 125

Tyr Ala Asp Ala Glu Cys Arg Ser Pro Thr Leu Ala Gly Gln Lys Glu
    130                 135                 140

His Gln Glu Phe Phe Asn Ala Met Lys Glu Ser Phe Arg Lys Ala Phe
145                 150                 155                 160

Lys Asn Val Asp Lys Glu Leu Lys Leu Gln Arg Asn Ile Asp Ser Ile
                165                 170                 175

Cys Ser Gly Thr Thr Ala Val Thr Leu Ile Lys Gln Gly His Asp Leu
            180                 185                 190

Ile Val Gly Asn Leu Gly Asp Ser Arg Ala Val Leu Gly Thr Arg Asp
        195                 200                 205

Gln Asn Asp Lys Leu Val Ala His Gln Leu Thr Val Asp Leu Lys Pro
    210                 215                 220

Asp His Pro Arg Glu Ala Arg Arg Ile Arg Arg Cys Asn Gly Arg Val
225                 230                 235                 240

Phe Ala His Gln Asp Glu Pro Asp Val Ala Arg Leu Trp Leu Pro Asn
                245                 250                 255

Cys Asn Ser Pro Gly Leu Ala Met Ala Arg Ala Phe Gly Asp Phe Cys
            260                 265                 270

Leu Lys Asp Phe Gly Leu Ile Ser Val Pro Asp Val Thr Tyr Arg Gln
        275                 280                 285

Ile Thr Glu Lys Asp Glu Phe Ile Val Leu Ala Thr Asp Gly Val Trp
    290                 295                 300

Asp Val Leu Ser Asn Gln Glu Val Val Asp Val Val Ala Ser Cys Ser
305                 310                 315                 320
```

-continued

```
Gly Arg Phe Ala Ala Ala Arg Ser Val Val Asp Leu Ala Asn Glu Thr
                325                 330                 335

Trp Arg Phe Lys Tyr Pro Thr Ser Lys Thr Asp Asp Cys Ala Val Val
            340                 345                 350

Cys Leu Phe Leu Asn Lys Tyr Glu Val Thr Gly Gly Leu Ser Gly Gln
        355                 360                 365

Pro Gly Tyr Ser Pro Arg Met Pro Ala Leu Ser Gly Ile Thr Arg Pro
    370                 375                 380

Asn Ser Lys Arg Val Thr Pro Asp Asp Val Asp Asp Gly Ser Asp Ser
385                 390                 395                 400

Asn Val Ser Gly Asp Glu Arg Ser Leu Asp Gly Phe Thr Arg Leu Asn
                405                 410                 415

Thr Leu Leu Ala Leu Pro Lys Phe Gly Asp Thr Ser Pro Thr Lys Lys
            420                 425                 430


<210> SEQ ID NO 18
<211> LENGTH: 1284
<212> TYPE: DNA
<213> ORGANISM: Oryza sativa
<220> FEATURE:
<221> NAME/KEY: CDS
<222> LOCATION: (1)..(1284)

<400> SEQUENCE: 18

atg ggg aac tgc gtg gcg agg agc ggg acg gcg gtg gat gcg ggt ggt       48
Met Gly Asn Cys Val Ala Arg Ser Gly Thr Ala Val Asp Ala Gly Gly
1               5                   10                  15

gat gga ggg gag gat ggg aag agg cgg agg agg agg tgg aag gcg ccg       96
Asp Gly Gly Glu Asp Gly Lys Arg Arg Arg Arg Arg Trp Lys Ala Pro
            20                  25                  30

cgg gaa gat cag ctc ggg atg gtg ccc ggc cgg atc ttc tcc aac gac      144
Arg Glu Asp Gln Leu Gly Met Val Pro Gly Arg Ile Phe Ser Asn Asp
        35                  40                  45

ggc cgc agc cgg acg gcg acg gtg tac acg cag caa ggg cgc aag ggg      192
Gly Arg Ser Arg Thr Ala Thr Val Tyr Thr Gln Gln Gly Arg Lys Gly
    50                  55                  60

atc aac cag gac gcc atg ctc gtc tgg gat ggg ttc ggc ggc gag gac      240
Ile Asn Gln Asp Ala Met Leu Val Trp Asp Gly Phe Gly Gly Glu Asp
65                  70                  75                  80

gac ggc gtg ctg tgc ggg gtg ttc gac ggg cac ggg ccg cac ggg cac      288
Asp Gly Val Leu Cys Gly Val Phe Asp Gly His Gly Pro His Gly His
                85                  90                  95

gtg gtg gcg cgg agg gtc cgc gac tcg ctg ccg ctg agg ctc atg tcc      336
Val Val Ala Arg Arg Val Arg Asp Ser Leu Pro Leu Arg Leu Met Ser
            100                 105                 110

gcg gcg cgc gac agc ggg gcg gac atg ccg gcc gcc gca tgg agg aag      384
Ala Ala Arg Asp Ser Gly Ala Asp Met Pro Ala Ala Ala Trp Arg Lys
        115                 120                 125

gcc ttc gcg cgc gcc tac aag gcc atg gac aag gac ctc cgg tcg cac      432
Ala Phe Ala Arg Ala Tyr Lys Ala Met Asp Lys Asp Leu Arg Ser His
    130                 135                 140

cct tcc ctc gat tgc ttc tgc agc gga agc act gcc gtc acc gtc ctc      480
Pro Ser Leu Asp Cys Phe Cys Ser Gly Ser Thr Ala Val Thr Val Leu
145                 150                 155                 160

aag ctc ggc tcg gat ctc tac atg gcc aac att ggg gac tcg cgc gcc      528
Lys Leu Gly Ser Asp Leu Tyr Met Ala Asn Ile Gly Asp Ser Arg Ala
                165                 170                 175

gtg ctc ggc tcc agg gag gcc acc ggc ggc ggc atg gtc gcc gtg cag      576
Val Leu Gly Ser Arg Glu Ala Thr Gly Gly Gly Met Val Ala Val Gln
            180                 185                 190
```

```
ctc acc gtt gat ctc aag ccg gat gtc ccc agc gaa gcg gag agg atc      624
Leu Thr Val Asp Leu Lys Pro Asp Val Pro Ser Glu Ala Glu Arg Ile
        195                 200                 205

aag aag tgc agg ggc agg gtg ttc gcg ctg cag gac gag ccg gag gtg      672
Lys Lys Cys Arg Gly Arg Val Phe Ala Leu Gln Asp Glu Pro Glu Val
    210                 215                 220

cca agg gtc tgg ctg ccg ttc gac gac gcg ccg ggc ctc gcg atg gcg      720
Pro Arg Val Trp Leu Pro Phe Asp Asp Ala Pro Gly Leu Ala Met Ala
225                 230                 235                 240

cga gcg ttc ggg gac ttc tgc ctg aaa gat tac ggg gtc atc tcg gtg      768
Arg Ala Phe Gly Asp Phe Cys Leu Lys Asp Tyr Gly Val Ile Ser Val
                245                 250                 255

ccg gaa ttc ttc cac tgg tct ctc aca gaa aag gac cag ttc gtc att      816
Pro Glu Phe Phe His Trp Ser Leu Thr Glu Lys Asp Gln Phe Val Ile
            260                 265                 270

ctt gca tcg gat ggg gta tgg gat gtc ctc agc aat caa gag gct gtt      864
Leu Ala Ser Asp Gly Val Trp Asp Val Leu Ser Asn Gln Glu Ala Val
        275                 280                 285

gat ata gtg tcc gcg tcc cca agc aga tca aag gct gca aaa tcc ctt      912
Asp Ile Val Ser Ala Ser Pro Ser Arg Ser Lys Ala Ala Lys Ser Leu
    290                 295                 300

gtt gag gca gcc act cgt gaa tgg aaa acc aaa tat cca aca tcc aaa      960
Val Glu Ala Ala Thr Arg Glu Trp Lys Thr Lys Tyr Pro Thr Ser Lys
305                 310                 315                 320

atc gat gat tgc gcg gtt gtt tgc tta tat ttg gat gga aaa atg gac     1008
Ile Asp Asp Cys Ala Val Val Cys Leu Tyr Leu Asp Gly Lys Met Asp
                325                 330                 335

cat gag cgt gac tca act gcc tca ttg gac aac atc agt att gaa gag     1056
His Glu Arg Asp Ser Thr Ala Ser Leu Asp Asn Ile Ser Ile Glu Glu
            340                 345                 350

ggt tca gtt gca gat cct aat gaa cct cag gag cag gag ccc acc tta     1104
Gly Ser Val Ala Asp Pro Asn Glu Pro Gln Glu Gln Glu Pro Thr Leu
        355                 360                 365

act cgg aat ttc aca gtt agg aca gtt gca ggc agc acg caa gag aag     1152
Thr Arg Asn Phe Thr Val Arg Thr Val Ala Gly Ser Thr Gln Glu Lys
    370                 375                 380

acc tta gca ggg gtg gat gcg agg att gct ggt gta gcg aac gac caa     1200
Thr Leu Ala Gly Val Asp Ala Arg Ile Ala Gly Val Ala Asn Asp Gln
385                 390                 395                 400

aat tgg tca ggt ctc gat gga gtg aca cgg gta aac tca ctt gtt cag     1248
Asn Trp Ser Gly Leu Asp Gly Val Thr Arg Val Asn Ser Leu Val Gln
                405                 410                 415

ctt cct agg ttt tct gaa gag agg gca att ggc tga                     1284
Leu Pro Arg Phe Ser Glu Glu Arg Ala Ile Gly
            420                 425


<210> SEQ ID NO 19
<211> LENGTH: 427
<212> TYPE: PRT
<213> ORGANISM: Oryza sativa

<400> SEQUENCE: 19

Met Gly Asn Cys Val Ala Arg Ser Gly Thr Ala Val Asp Ala Gly Gly
1               5                   10                  15

Asp Gly Gly Glu Asp Gly Lys Arg Arg Arg Arg Arg Trp Lys Ala Pro
            20                  25                  30

Arg Glu Asp Gln Leu Gly Met Val Pro Gly Arg Ile Phe Ser Asn Asp
        35                  40                  45

Gly Arg Ser Arg Thr Ala Thr Val Tyr Thr Gln Gln Gly Arg Lys Gly
```

```
    50                  55                  60

Ile Asn Gln Asp Ala Met Leu Val Trp Asp Gly Phe Gly Gly Glu Asp
65                  70                  75                  80

Asp Gly Val Leu Cys Gly Val Phe Asp Gly His Gly Pro His Gly His
                85                  90                  95

Val Val Ala Arg Arg Val Arg Asp Ser Leu Pro Leu Arg Leu Met Ser
            100                 105                 110

Ala Ala Arg Asp Ser Gly Ala Asp Met Pro Ala Ala Ala Trp Arg Lys
        115                 120                 125

Ala Phe Ala Arg Ala Tyr Lys Ala Met Asp Lys Asp Leu Arg Ser His
    130                 135                 140

Pro Ser Leu Asp Cys Phe Cys Ser Gly Ser Thr Ala Val Thr Val Leu
145                 150                 155                 160

Lys Leu Gly Ser Asp Leu Tyr Met Ala Asn Ile Gly Asp Ser Arg Ala
                165                 170                 175

Val Leu Gly Ser Arg Glu Ala Thr Gly Gly Gly Met Val Ala Val Gln
            180                 185                 190

Leu Thr Val Asp Leu Lys Pro Asp Val Pro Ser Glu Ala Glu Arg Ile
        195                 200                 205

Lys Lys Cys Arg Gly Arg Val Phe Ala Leu Gln Asp Glu Pro Glu Val
    210                 215                 220

Pro Arg Val Trp Leu Pro Phe Asp Asp Ala Pro Gly Leu Ala Met Ala
225                 230                 235                 240

Arg Ala Phe Gly Asp Phe Cys Leu Lys Asp Tyr Gly Val Ile Ser Val
                245                 250                 255

Pro Glu Phe Phe His Trp Ser Leu Thr Glu Lys Asp Gln Phe Val Ile
            260                 265                 270

Leu Ala Ser Asp Gly Val Trp Asp Val Leu Ser Asn Gln Glu Ala Val
        275                 280                 285

Asp Ile Val Ser Ala Ser Pro Ser Arg Ser Lys Ala Ala Lys Ser Leu
    290                 295                 300

Val Glu Ala Ala Thr Arg Glu Trp Lys Thr Lys Tyr Pro Thr Ser Lys
305                 310                 315                 320

Ile Asp Asp Cys Ala Val Val Cys Leu Tyr Leu Asp Gly Lys Met Asp
                325                 330                 335

His Glu Arg Asp Ser Thr Ala Ser Leu Asp Asn Ile Ser Ile Glu Glu
            340                 345                 350

Gly Ser Val Ala Asp Pro Asn Glu Pro Gln Glu Gln Glu Pro Thr Leu
        355                 360                 365

Thr Arg Asn Phe Thr Val Arg Thr Val Ala Gly Ser Thr Gln Glu Lys
    370                 375                 380

Thr Leu Ala Gly Val Asp Ala Arg Ile Ala Gly Val Ala Asn Asp Gln
385                 390                 395                 400

Asn Trp Ser Gly Leu Asp Gly Val Thr Arg Val Asn Ser Leu Val Gln
                405                 410                 415

Leu Pro Arg Phe Ser Glu Glu Arg Ala Ile Gly
            420                 425


<210> SEQ ID NO 20
<211> LENGTH: 1596
<212> TYPE: DNA
<213> ORGANISM: Oryza sativa
<220> FEATURE:
<221> NAME/KEY: CDS
<222> LOCATION: (1)..(1596)
```

<400> SEQUENCE: 20

```
atg ggc tcc tgc ctc tcc tcc gac ctg cct ccc cgc gcc ggc gcc ggc       48
Met Gly Ser Cys Leu Ser Ser Asp Leu Pro Pro Arg Ala Gly Ala Gly
1               5                   10                  15

gcg gga gcg tca ccc ggg tgg ccg cag cgg tgg cgg agg agg agg cag       96
Ala Gly Ala Ser Pro Gly Trp Pro Gln Arg Trp Arg Arg Arg Arg Gln
            20                  25                  30

cgg ggg gtg gag cgg ggc ggg gct gtt tcc ggc ggc ggc ggc ggc gtc      144
Arg Gly Val Glu Arg Gly Gly Ala Val Ser Gly Gly Gly Gly Gly Val
        35                  40                  45

ttc tcc atc ggc gtc ggc ggc aag aag ctg cac cac ggc ggc gga gga      192
Phe Ser Ile Gly Val Gly Gly Lys Lys Leu His His Gly Gly Gly Gly
    50                  55                  60

gga ggg gag atg acg gag gag gag ctc gcg aag gtc gag ggg agg gtg      240
Gly Gly Glu Met Thr Glu Glu Glu Leu Ala Lys Val Glu Gly Arg Val
65                  70                  75                  80

tgc gtc aac ggc gcg agc gcg gcg gcg tgc ctg cac acg cag cag ggg      288
Cys Val Asn Gly Ala Ser Ala Ala Ala Cys Leu His Thr Gln Gln Gly
                85                  90                  95

cgg aag ggc acc aac cag gac gcc atg gtc gtg tgg gag aac ttt aat      336
Arg Lys Gly Thr Asn Gln Asp Ala Met Val Val Trp Glu Asn Phe Asn
            100                 105                 110

aca agt gat agt gtc ttc tgt ggt gtg ttt gat ggt cat ggt cca tat      384
Thr Ser Asp Ser Val Phe Cys Gly Val Phe Asp Gly His Gly Pro Tyr
        115                 120                 125

ggt cat ttt gtt gcc aag aag gtc aga gat tct ctt cct gtc aaa ata      432
Gly His Phe Val Ala Lys Lys Val Arg Asp Ser Leu Pro Val Lys Ile
    130                 135                 140

cgc aca cta tgg aaa acc agt gcc aac gag gac act agt tcc cac caa      480
Arg Thr Leu Trp Lys Thr Ser Ala Asn Glu Asp Thr Ser Ser His Gln
145                 150                 155                 160

aat gga agc att tct gga agt gtt aat tca gaa gag tca cct gtt gtt      528
Asn Gly Ser Ile Ser Gly Ser Val Asn Ser Glu Glu Ser Pro Val Val
                165                 170                 175

gat gat gaa tgg ggt gaa tat gct gat gac agc gag aag ctt cct gag      576
Asp Asp Glu Trp Gly Glu Tyr Ala Asp Asp Ser Glu Lys Leu Pro Glu
            180                 185                 190

atg ttt ctt cca ctt aag cag tct tat ttt aag gct ttc aaa ttg atg      624
Met Phe Leu Pro Leu Lys Gln Ser Tyr Phe Lys Ala Phe Lys Leu Met
        195                 200                 205

gac aag gaa ctc aaa atg cac cct aca gtt gat tgc ttt tgc agt gga      672
Asp Lys Glu Leu Lys Met His Pro Thr Val Asp Cys Phe Cys Ser Gly
    210                 215                 220

tca aca gca gtc acg tta gta aaa cag gga ttg gat ctt gtg gtt ggg      720
Ser Thr Ala Val Thr Leu Val Lys Gln Gly Leu Asp Leu Val Val Gly
225                 230                 235                 240

aac ctt ggg gac tcg aga gca ata atg ggg aca cga gat gct gcc aat      768
Asn Leu Gly Asp Ser Arg Ala Ile Met Gly Thr Arg Asp Ala Ala Asn
                245                 250                 255

aat cta act gct gta caa ctc aca gtt gat ttg aag cct aac ctt cca      816
Asn Leu Thr Ala Val Gln Leu Thr Val Asp Leu Lys Pro Asn Leu Pro
            260                 265                 270

agg gaa gct gcg agg atc cag cag tgt agg gga aga gtt ttt gct ctt      864
Arg Glu Ala Ala Arg Ile Gln Gln Cys Arg Gly Arg Val Phe Ala Leu
        275                 280                 285

cag gat gaa cca gaa gtt gcc aga gta tgg ttg cca aat aat gac tct      912
Gln Asp Glu Pro Glu Val Ala Arg Val Trp Leu Pro Asn Asn Asp Ser
    290                 295                 300
```

-continued

```
cct gga ttg gca atg gca aga gct ttt gga gac ttc tgc ctt aaa gat      960
Pro Gly Leu Ala Met Ala Arg Ala Phe Gly Asp Phe Cys Leu Lys Asp
305                 310                 315                 320

tat ggt tta ata tct gtt cca cag ata tcc tat cgt cgt ctt act gaa     1008
Tyr Gly Leu Ile Ser Val Pro Gln Ile Ser Tyr Arg Arg Leu Thr Glu
                325                 330                 335

aag gat gag ttc ata ata ctg gcc act gat ggg gtt tgg gac gtc ctc     1056
Lys Asp Glu Phe Ile Ile Leu Ala Thr Asp Gly Val Trp Asp Val Leu
            340                 345                 350

tca aac aag gag gct gtt gac ata gta gcc gca gct cca tct cgt gca     1104
Ser Asn Lys Glu Ala Val Asp Ile Val Ala Ala Ala Pro Ser Arg Ala
        355                 360                 365

acg gct gcc agg gct ctt gtc gac tgt gct gtc aga tca tgg aga ttg     1152
Thr Ala Ala Arg Ala Leu Val Asp Cys Ala Val Arg Ser Trp Arg Leu
    370                 375                 380

aag ttc cca aca tcc aag agc gat gac tgc gct gtt gtg tgc cta ttc     1200
Lys Phe Pro Thr Ser Lys Ser Asp Asp Cys Ala Val Val Cys Leu Phe
385                 390                 395                 400

tta gac cat gca aag tca cct gac ttg att caa gag aac gag agc gag     1248
Leu Asp His Ala Lys Ser Pro Asp Leu Ile Gln Glu Asn Glu Ser Glu
                405                 410                 415

gaa gaa act aca gag gat gtt gca atc cca gac acc gtt gct aag gtt     1296
Glu Glu Thr Thr Glu Asp Val Ala Ile Pro Asp Thr Val Ala Lys Val
            420                 425                 430

gac caa gac att gca caa gga gat gca cat atc tcc agt gaa gag caa     1344
Asp Gln Asp Ile Ala Gln Gly Asp Ala His Ile Ser Ser Glu Glu Gln
        435                 440                 445

atc acc gag cca gca ttg cag cac tcc tac aca tta agg gat gtt gat     1392
Ile Thr Glu Pro Ala Leu Gln His Ser Tyr Thr Leu Arg Asp Val Asp
    450                 455                 460

gag att gta ccg gta gag gag cct cca gtc tca aag gaa cct gaa aga     1440
Glu Ile Val Pro Val Glu Glu Pro Pro Val Ser Lys Glu Pro Glu Arg
465                 470                 475                 480

tgt gga tct gcc cgc agc ctt gct gat tgt ata tcc aca aac gag gag     1488
Cys Gly Ser Ala Arg Ser Leu Ala Asp Cys Ile Ser Thr Asn Glu Glu
                485                 490                 495

gag gaa tgg tca gca ctc gaa ggt gtg acg cgg gtc aat tcc ctc ttg     1536
Glu Glu Trp Ser Ala Leu Glu Gly Val Thr Arg Val Asn Ser Leu Leu
            500                 505                 510

aac ctt ccc aga ata ctt tca ggc gag aag aga tca acc agc tgg agg     1584
Asn Leu Pro Arg Ile Leu Ser Gly Glu Lys Arg Ser Thr Ser Trp Arg
        515                 520                 525

aag cgg cga tga                                                     1596
Lys Arg Arg
    530


<210> SEQ ID NO 21
<211> LENGTH: 531
<212> TYPE: PRT
<213> ORGANISM: Oryza sativa

<400> SEQUENCE: 21

Met Gly Ser Cys Leu Ser Ser Asp Leu Pro Pro Arg Ala Gly Ala Gly
1               5                   10                  15

Ala Gly Ala Ser Pro Gly Trp Pro Gln Arg Trp Arg Arg Arg Arg Gln
            20                  25                  30

Arg Gly Val Glu Arg Gly Gly Ala Val Ser Gly Gly Gly Gly Gly Val
        35                  40                  45

Phe Ser Ile Gly Val Gly Gly Lys Lys Leu His His Gly Gly Gly Gly
    50                  55                  60
```

-continued

```
Gly Gly Glu Met Thr Glu Glu Glu Leu Ala Lys Val Glu Gly Arg Val
65                  70                  75                  80

Cys Val Asn Gly Ala Ser Ala Ala Ala Cys Leu His Thr Gln Gln Gly
                85                  90                  95

Arg Lys Gly Thr Asn Gln Asp Ala Met Val Val Trp Glu Asn Phe Asn
            100                 105                 110

Thr Ser Asp Ser Val Phe Cys Gly Val Phe Asp Gly His Gly Pro Tyr
        115                 120                 125

Gly His Phe Val Ala Lys Lys Val Arg Asp Ser Leu Pro Val Lys Ile
    130                 135                 140

Arg Thr Leu Trp Lys Thr Ser Ala Asn Glu Asp Thr Ser Ser His Gln
145                 150                 155                 160

Asn Gly Ser Ile Ser Gly Ser Val Asn Ser Glu Glu Ser Pro Val Val
                165                 170                 175

Asp Asp Glu Trp Gly Glu Tyr Ala Asp Asp Ser Glu Lys Leu Pro Glu
            180                 185                 190

Met Phe Leu Pro Leu Lys Gln Ser Tyr Phe Lys Ala Phe Lys Leu Met
        195                 200                 205

Asp Lys Glu Leu Lys Met His Pro Thr Val Asp Cys Phe Cys Ser Gly
    210                 215                 220

Ser Thr Ala Val Thr Leu Val Lys Gln Gly Leu Asp Leu Val Val Gly
225                 230                 235                 240

Asn Leu Gly Asp Ser Arg Ala Ile Met Gly Thr Arg Asp Ala Ala Asn
                245                 250                 255

Asn Leu Thr Ala Val Gln Leu Thr Val Asp Leu Lys Pro Asn Leu Pro
            260                 265                 270

Arg Glu Ala Ala Arg Ile Gln Gln Cys Arg Gly Arg Val Phe Ala Leu
        275                 280                 285

Gln Asp Glu Pro Glu Val Ala Arg Val Trp Leu Pro Asn Asn Asp Ser
    290                 295                 300

Pro Gly Leu Ala Met Ala Arg Ala Phe Gly Asp Phe Cys Leu Lys Asp
305                 310                 315                 320

Tyr Gly Leu Ile Ser Val Pro Gln Ile Ser Tyr Arg Arg Leu Thr Glu
                325                 330                 335

Lys Asp Glu Phe Ile Ile Leu Ala Thr Asp Gly Val Trp Asp Val Leu
            340                 345                 350

Ser Asn Lys Glu Ala Val Asp Ile Val Ala Ala Ala Pro Ser Arg Ala
        355                 360                 365

Thr Ala Ala Arg Ala Leu Val Asp Cys Ala Val Arg Ser Trp Arg Leu
    370                 375                 380

Lys Phe Pro Thr Ser Lys Ser Asp Asp Cys Ala Val Val Cys Leu Phe
385                 390                 395                 400

Leu Asp His Ala Lys Ser Pro Asp Leu Ile Gln Glu Asn Glu Ser Glu
                405                 410                 415

Glu Glu Thr Thr Glu Asp Val Ala Ile Pro Asp Thr Val Ala Lys Val
            420                 425                 430

Asp Gln Asp Ile Ala Gln Gly Asp Ala His Ile Ser Ser Glu Glu Gln
        435                 440                 445

Ile Thr Glu Pro Ala Leu Gln His Ser Tyr Thr Leu Arg Asp Val Asp
    450                 455                 460

Glu Ile Val Pro Val Glu Glu Pro Pro Val Ser Lys Glu Pro Glu Arg
465                 470                 475                 480
```

-continued

```
Cys Gly Ser Ala Arg Ser Leu Ala Asp Cys Ile Ser Thr Asn Glu Glu
                485                 490                 495

Glu Glu Trp Ser Ala Leu Glu Gly Val Thr Arg Val Asn Ser Leu Leu
            500                 505                 510

Asn Leu Pro Arg Ile Leu Ser Gly Glu Lys Arg Ser Thr Ser Trp Arg
        515                 520                 525

Lys Arg Arg
    530


<210> SEQ ID NO 22
<211> LENGTH: 1170
<212> TYPE: DNA
<213> ORGANISM: Oryza sativa
<220> FEATURE:
<221> NAME/KEY: CDS
<222> LOCATION: (1)..(1170)

<400> SEQUENCE: 22

atg ggg atc tgt gca tct tca gag cag ctg gag cat gtt cat gag aca       48
Met Gly Ile Cys Ala Ser Ser Glu Gln Leu Glu His Val His Glu Thr
1               5                   10                  15

gat gag agc att gtg tat gtg aag gat gag caa gga agg ggg ggt agg       96
Asp Glu Ser Ile Val Tyr Val Lys Asp Glu Gln Gly Arg Gly Gly Arg
            20                  25                  30

ggg gtg gag agt ggg ggg gct agg aag gtg gcc tcc ctc ttc tcc cag      144
Gly Val Glu Ser Gly Gly Ala Arg Lys Val Ala Ser Leu Phe Ser Gln
        35                  40                  45

agg ggc aag aaa ggc ccc aac cag gac tct gtc atc ctc tgc cag gga      192
Arg Gly Lys Lys Gly Pro Asn Gln Asp Ser Val Ile Leu Cys Gln Gly
    50                  55                  60

ttc ggc atg gag gac ggc gtg ttc tgc ggc gtg ttc gac ggc cat ggc      240
Phe Gly Met Glu Asp Gly Val Phe Cys Gly Val Phe Asp Gly His Gly
65                  70                  75                  80

cgg tgc ggg caa ttc atc agc aag ctg gtg cgg gac tac ctc ccg ttc      288
Arg Cys Gly Gln Phe Ile Ser Lys Leu Val Arg Asp Tyr Leu Pro Phe
                85                  90                  95

atg atc ctg agc cac cgg aac gcg ctg ctc ctg gcc gac gcc gcc gcc      336
Met Ile Leu Ser His Arg Asn Ala Leu Leu Leu Ala Asp Ala Ala Ala
            100                 105                 110

gac gac gac gac gac gcc gcg ttc agc gac gac gcg gcg gcg tcg tcg      384
Asp Asp Asp Asp Asp Ala Ala Phe Ser Asp Asp Ala Ala Ala Ser Ser
        115                 120                 125

tcc gcg gac agc agc ggc aac tcg tcg ccg cag ccg tcg gcg tcg gcg      432
Ser Ala Asp Ser Ser Gly Asn Ser Ser Pro Gln Pro Ser Ala Ser Ala
    130                 135                 140

tcg gcg cag atg ctg gag gag tgg agg cag gcg tgc gcc agc gcg ttc      480
Ser Ala Gln Met Leu Glu Glu Trp Arg Gln Ala Cys Ala Ser Ala Phe
145                 150                 155                 160

gcc gcc atg gac ggc gag ctc aag ctc cag ccg aac ctc gac tgc gcg      528
Ala Ala Met Asp Gly Glu Leu Lys Leu Gln Pro Asn Leu Asp Cys Ala
                165                 170                 175

ttc agc ggc acg acg gcg gtg tgc gcc atc aag cag ggc agg gac ctc      576
Phe Ser Gly Thr Thr Ala Val Cys Ala Ile Lys Gln Gly Arg Asp Leu
            180                 185                 190

atc atc gcc aac ctc ggc gac tcg agg gcg gtg ctc gcc acc atg tcg      624
Ile Ile Ala Asn Leu Gly Asp Ser Arg Ala Val Leu Ala Thr Met Ser
        195                 200                 205

gac acc ggc tac ctc cag gcg gtg cag ctg acg gtg gac cac aag ccg      672
Asp Thr Gly Tyr Leu Gln Ala Val Gln Leu Thr Val Asp His Lys Pro
    210                 215                 220
```

```
agc gtg ccg gag gag gcg gcg agg atc aag cgg agc ggg ggg agg gtg       720
Ser Val Pro Glu Glu Ala Ala Arg Ile Lys Arg Ser Gly Gly Arg Val
225                 230                 235                 240

ttc ggg ctg aag gac gag ccg ggg gtg atg cgg gtg tgg ctc ccc ggc       768
Phe Gly Leu Lys Asp Glu Pro Gly Val Met Arg Val Trp Leu Pro Gly
                245                 250                 255

gag aac tcg ccg ggg ctc gcc atg gcg agg tcg ctg ggc gac atg agg       816
Glu Asn Ser Pro Gly Leu Ala Met Ala Arg Ser Leu Gly Asp Met Arg
            260                 265                 270

ctg aag cgg cac ggc gtg atc ccg gcg ccg gag gtg acg tcg cgg cgc       864
Leu Lys Arg His Gly Val Ile Pro Ala Pro Glu Val Thr Ser Arg Arg
        275                 280                 285

gtg acg ggc gcc gac ctg ttc atg gtg ctc gcc acg gac ggg gtg tgg       912
Val Thr Gly Ala Asp Leu Phe Met Val Leu Ala Thr Asp Gly Val Trp
    290                 295                 300

gac gtg ctg agc aac gag gag gtg gtg tcc atc gtg tgc gcg acg ccg       960
Asp Val Leu Ser Asn Glu Glu Val Val Ser Ile Val Cys Ala Thr Pro
305                 310                 315                 320

cgg aag cag cac gcg tcg aag gcg gtg gtg gag gcc gcc gtg cag cgg      1008
Arg Lys Gln His Ala Ser Lys Ala Val Val Glu Ala Ala Val Gln Arg
                325                 330                 335

tgg cgg gcc aag ttc ccg acg tcc agg gtg gac gac tgc tcc gcc gtc      1056
Trp Arg Ala Lys Phe Pro Thr Ser Arg Val Asp Asp Cys Ser Ala Val
            340                 345                 350

tgc ctc ttc ctc cac gac cac acc ctc ggc acg gcc gcc gcc gcc tcc      1104
Cys Leu Phe Leu His Asp His Thr Leu Gly Thr Ala Ala Ala Ala Ser
        355                 360                 365

gcc gca gcc gcc gcg gcc gcc aga aag gcg cgc agg gcc tcc acc gcc      1152
Ala Ala Ala Ala Ala Ala Ala Arg Lys Ala Arg Arg Ala Ser Thr Ala
    370                 375                 380

acg ccg ccg gcg agc tga                                              1170
Thr Pro Pro Ala Ser
385


<210> SEQ ID NO 23
<211> LENGTH: 389
<212> TYPE: PRT
<213> ORGANISM: Oryza sativa

<400> SEQUENCE: 23

Met Gly Ile Cys Ala Ser Ser Glu Gln Leu Glu His Val His Glu Thr
1               5                   10                  15

Asp Glu Ser Ile Val Tyr Val Lys Asp Glu Gln Gly Arg Gly Gly Arg
            20                  25                  30

Gly Val Glu Ser Gly Gly Ala Arg Lys Val Ala Ser Leu Phe Ser Gln
        35                  40                  45

Arg Gly Lys Lys Gly Pro Asn Gln Asp Ser Val Ile Leu Cys Gln Gly
    50                  55                  60

Phe Gly Met Glu Asp Gly Val Phe Cys Gly Val Phe Asp Gly His Gly
65                  70                  75                  80

Arg Cys Gly Gln Phe Ile Ser Lys Leu Val Arg Asp Tyr Leu Pro Phe
                85                  90                  95

Met Ile Leu Ser His Arg Asn Ala Leu Leu Leu Ala Asp Ala Ala Ala
            100                 105                 110

Asp Asp Asp Asp Asp Ala Ala Phe Ser Asp Asp Ala Ala Ala Ser Ser
        115                 120                 125

Ser Ala Asp Ser Ser Gly Asn Ser Ser Pro Gln Pro Ser Ala Ser Ala
    130                 135                 140
```

-continued

```
Ser Ala Gln Met Leu Glu Glu Trp Arg Gln Ala Cys Ala Ser Ala Phe
145                 150                 155                 160

Ala Ala Met Asp Gly Glu Leu Lys Leu Gln Pro Asn Leu Asp Cys Ala
                165                 170                 175

Phe Ser Gly Thr Thr Ala Val Cys Ala Ile Lys Gln Gly Arg Asp Leu
            180                 185                 190

Ile Ile Ala Asn Leu Gly Asp Ser Arg Ala Val Leu Ala Thr Met Ser
        195                 200                 205

Asp Thr Gly Tyr Leu Gln Ala Val Gln Leu Thr Val Asp His Lys Pro
    210                 215                 220

Ser Val Pro Glu Glu Ala Ala Arg Ile Lys Arg Ser Gly Gly Arg Val
225                 230                 235                 240

Phe Gly Leu Lys Asp Glu Pro Gly Val Met Arg Val Trp Leu Pro Gly
                245                 250                 255

Glu Asn Ser Pro Gly Leu Ala Met Ala Arg Ser Leu Gly Asp Met Arg
            260                 265                 270

Leu Lys Arg His Gly Val Ile Pro Ala Pro Glu Val Thr Ser Arg Arg
        275                 280                 285

Val Thr Gly Ala Asp Leu Phe Met Val Leu Ala Thr Asp Gly Val Trp
    290                 295                 300

Asp Val Leu Ser Asn Glu Glu Val Val Ser Ile Val Cys Ala Thr Pro
305                 310                 315                 320

Arg Lys Gln His Ala Ser Lys Ala Val Val Glu Ala Ala Val Gln Arg
                325                 330                 335

Trp Arg Ala Lys Phe Pro Thr Ser Arg Val Asp Asp Cys Ser Ala Val
            340                 345                 350

Cys Leu Phe Leu His Asp His Thr Leu Gly Thr Ala Ala Ala Ala Ser
        355                 360                 365

Ala Ala Ala Ala Ala Ala Ala Arg Lys Ala Arg Arg Ala Ser Thr Ala
    370                 375                 380

Thr Pro Pro Ala Ser
385
```

<210> SEQ ID NO 24
<211> LENGTH: 25
<212> TYPE: DNA
<213> ORGANISM: Artificial
<220> FEATURE:
<223> OTHER INFORMATION: Synthetic DNA

<400> SEQUENCE: 24
tgctttcgcc attaaatagc gacgg 25

<210> SEQ ID NO 25
<211> LENGTH: 23
<212> TYPE: DNA
<213> ORGANISM: Artificial
<220> FEATURE:
<223> OTHER INFORMATION: Synthetic DNA

<400> SEQUENCE: 25
cgctgcggac atctacattt ttg 23

<210> SEQ ID NO 26
<211> LENGTH: 22
<212> TYPE: DNA
<213> ORGANISM: Artificial
<220> FEATURE:
<223> OTHER INFORMATION: Synthetic DNA

<400> SEQUENCE: 26
tcccggacat gaagccattt ac 22

<210> SEQ ID NO 27
<211> LENGTH: 16
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 27
ngtcgaswga nawgaa 16

<210> SEQ ID NO 28
<211> LENGTH: 498
<212> TYPE: DNA
<213> ORGANISM: Arabidopsis thaliana
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 28
taaccttacg ctttgctcgg tcccagacgc aagattacat ctctttctat ggnttgagat 60
cgnacggacg gctgtttgag gacggtccaa ttgccactag ccagatttac gtgcatagca 120
agttaatgat tgttgatgac cggatcgcag tgatcggatc ttctaatata aacgatagga 180
gcttactagg ttcacgagac tctgaggtac tttcaaaaat ccaattcatt ctttattgca 240
gcaaaacaga gttatgtatt catttgaatc aatcatgttt cagatcggtg ttgtgattga 300
agacaaagaa ttcgtggaat cttcgatgaa cggaatgaag tggatggccg ggaagttctc 360
ttacagtctt agatgttcct tgtggtcaga gcatctcggc cttcacgccg gagaggtaat 420
tttaaaaaat ttctagaaac gcctactact atacattttt gacttcagaa acctttattt 480
tcatctcact cgaccaaa 498

<210> SEQ ID NO 29
<211> LENGTH: 39
<212> TYPE: DNA
<213> ORGANISM: Artificial
<220> FEATURE:
<223> OTHER INFORMATION: Synthetic DNA

<400> SEQUENCE: 29
acgcgtcgac atgggacatt tctcttccat gttcaacgg 39

<210> SEQ ID NO 30
<211> LENGTH: 43
<212> TYPE: DNA
<213> ORGANISM: Artificial
<220> FEATURE:
<223> OTHER INFORMATION: Synthetic DNA

<400> SEQUENCE: 30
tgtacatgta cactatagag atggcgacga cgatgaagaa tgg 43

<210> SEQ ID NO 31
<211> LENGTH: 29
<212> TYPE: DNA
<213> ORGANISM: Artificial
<220> FEATURE:
<223> OTHER INFORMATION: Synthetic DNA

<400> SEQUENCE: 31
aggatccatg ggacatttct cttccatgt 29

<210> SEQ ID NO 32
<211> LENGTH: 27
<212> TYPE: DNA
<213> ORGANISM: Artificial
<220> FEATURE:
<223> OTHER INFORMATION: Synthetic DNA

<400> SEQUENCE: 32
agagctccta tagagatggc gacgacg 27

<210> SEQ ID NO 33
<211> LENGTH: 1992
<212> TYPE: DNA
<213> ORGANISM: Zea mays

<400> SEQUENCE: 33
ctgcagtgca gcgtgacccg gtcgtgcccc tctctagaga taatgagcat tgcatgtcta 60
agttataaaa aattaccaca tatttttttt gtcacacttg tttgaagtgc agtttatcta 120
tctttataca tatatttaaa ctttactcta cgaataatat aatctatagt actacaataa 180
tatcagtgtt ttagagaatc atataaatga acagttagac atggtctaaa ggacaattga 240
gtattttgac aacaggactc tacagtttta tctttttagt gtgcatgtgt tctccttttt 300
ttttgcaaat agcttcacct atataatact tcatccattt tattagtaca tccatttagg 360
gtttagggtt aatggttttt atagactaat ttttttagta catctatttt attctatttt 420
agcctctaaa ttaagaaaac taaaactcta ttttagtttt tttatttaat aatttagata 480
taaaatagaa taaaataaag tgactaaaaa ttaaacaaat accctttaag aaattaaaaa 540
aactaaggaa acatttttct tgtttcgagt agataatgcc agcctgttaa acgccgtcga 600
cgagtctaac ggacaccaac cagcgaacca gcagcgtcgc gtcgggccaa gcgaagcaga 660
cggcacggca tctctgtcgc tgcctctgga cccctctcga gagttccgct ccaccgttgg 720
acttgctccg ctgtcggcat ccagaaattg cgtggcggag cggcagacgt gagccggcac 780
ggcaggcggc ctcctcctcc tctcacggca cggcagctac gggggattcc tttcccaccg 840
ctccttcgct ttcccttcct cgcccgccgt aataaataga caccccctcc acaccctctt 900
tccccaacct cgtgttgttc ggagcgcaca cacacacaac cagatctccc ccaaatccac 960
ccgtcggcac ctccgcttca aggtacgccg ctcgtcctcc cccccccccc ctctctacct 1020
tctctagatc ggcgttccgg tccatggtta gggcccggta gttctacttc tgttcatgtt 1080
tgtgttagat ccgtgtttgt gttagatccg tgctgctagc gttcgtacac ggatgcgacc 1140
tgtacgtcag acacgttctg attgctaact tgccagtgtt tctctttggg gaatcctggg 1200
atggctctag ccgttccgca gacgggatcg atttcatgat tttttttgtt tcgttgcata 1260
gggtttggtt tgccctttc ctttatttca atatatgccg tgcacttgtt tgtcgggtca 1320

-continued

```
tcttttcatg cttttttttg tcttggttgt gatgatgtgg tctggttggg cggtcgttct   1380

agatcggagt agaattctgt ttcaaactac ctggtggatt tattaatttt ggatctgtat   1440

gtgtgtgcca tacatattca tagttacgaa ttgaagatga tggatggaaa tatcgatcta   1500

ggataggtat acatgttgat gcgggtttta ctgatgcata tacagagatg ctttttgttc   1560

gcttggttgt gatgatgtgg tgtggttggg cggtcgttca ttcgttctag atcggagtag   1620

aatactgttt caaactacct ggtgtattta ttaattttgg aactgtatgt gtgtgtcata   1680

catcttcata gttacgagtt taagatggat ggaaatatcg atctaggata ggtatacatg   1740

ttgatgtggg ttttactgat gcatatacat gatggcatat gcagcatcta ttcatatgct   1800

ctaaccttga gtacctatct attataataa acaagtatgt tttataatta ttttgatctt   1860

gatatacttg gatgatggca tatgcagcag ctatatgtgg attttttag ccctgccttc   1920

atacgctatt tatttgcttg gtactgtttc ttttgtcgat gctcaccctg ttgtttggtg   1980

ttacttctgc ag                                                        1992
```

```
<210> SEQ ID NO 34
<211> LENGTH: 256
<212> TYPE: DNA
<213> ORGANISM: Zea mays

<400> SEQUENCE: 34

gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atcggg                                                    256
```

```
<210> SEQ ID NO 35
<211> LENGTH: 1122
<212> TYPE: DNA
<213> ORGANISM: Arabidopsis thaliana
<220> FEATURE:
<221> NAME/KEY: CDS
<222> LOCATION: (1)..(1122)

<400> SEQUENCE: 35

atg gga cat ttc tca tcg atg ttc aat gga tta gct cga tca ttt tct       48
Met Gly His Phe Ser Ser Met Phe Asn Gly Leu Ala Arg Ser Phe Ser
1               5                   10                  15

ata aag aaa gtg aag aac aac aat gga aac tgc gac gca aag gaa gct       96
Ile Lys Lys Val Lys Asn Asn Asn Gly Asn Cys Asp Ala Lys Glu Ala
            20                  25                  30

gct gat gag atg gca agc gag gct aag aaa aaa gaa ttg att ctg aaa      144
Ala Asp Glu Met Ala Ser Glu Ala Lys Lys Lys Glu Leu Ile Leu Lys
        35                  40                  45

tcc tct ggt tat gtt aat gta caa gga tct aat aat tta gcc tct ctt      192
Ser Ser Gly Tyr Val Asn Val Gln Gly Ser Asn Asn Leu Ala Ser Leu
    50                  55                  60

ttc tcc aaa cgc ggc gaa aaa ggc gtt aat cag gat tgt gca ctc gtt      240
Phe Ser Lys Arg Gly Glu Lys Gly Val Asn Gln Asp Cys Ala Leu Val
65                  70                  75                  80

tgg gag gga ttt ggg tgc caa gaa gac atg atc ttc tgc ggg ata ttc      288
Trp Glu Gly Phe Gly Cys Gln Glu Asp Met Ile Phe Cys Gly Ile Phe
                85                  90                  95

gat gga cac ggt cca tgg ggt cac tat gta gcc aaa caa gta aga aac      336
```

```
Asp Gly His Gly Pro Trp Gly His Tyr Val Ala Lys Gln Val Arg Asn
            100                 105                 110

tca atg cct ttg tcg ctt ctt tgc aac tgg caa aag att ctt gct cag      384
Ser Met Pro Leu Ser Leu Leu Cys Asn Trp Gln Lys Ile Leu Ala Gln
        115                 120                 125

gcc act cta gaa ccc gag ctc gac ctc gaa ggc tct aat aaa aaa atc      432
Ala Thr Leu Glu Pro Glu Leu Asp Leu Glu Gly Ser Asn Lys Lys Ile
    130                 135                 140

tca aga ttc gac ata tgg aag caa tcc tat cta aaa acg tgt gca acg      480
Ser Arg Phe Asp Ile Trp Lys Gln Ser Tyr Leu Lys Thr Cys Ala Thr
145                 150                 155                 160

gtt gat caa gag ctt gaa cat cac cgc aag atc gat tct tac tat agc      528
Val Asp Gln Glu Leu Glu His His Arg Lys Ile Asp Ser Tyr Tyr Ser
                165                 170                 175

ggc aca aca gct cta acc att gtg aga cag ggt gaa gtt att tat gta      576
Gly Thr Thr Ala Leu Thr Ile Val Arg Gln Gly Glu Val Ile Tyr Val
            180                 185                 190

gca aat gta ggc gat tca aga gcg gta cta gcc atg gag tcg gat gag      624
Ala Asn Val Gly Asp Ser Arg Ala Val Leu Ala Met Glu Ser Asp Glu
        195                 200                 205

gga agc ttg gtt gcg gtt cag ctc acc ctc gat ttc aaa ccg aat cta      672
Gly Ser Leu Val Ala Val Gln Leu Thr Leu Asp Phe Lys Pro Asn Leu
    210                 215                 220

cca cag gag aag gag cgg ata att ggc tgc aaa ggg cgg gtt ttc tgt      720
Pro Gln Glu Lys Glu Arg Ile Ile Gly Cys Lys Gly Arg Val Phe Cys
225                 230                 235                 240

cta gat gat gag ccg gga gtc cat cgt gtg tgg cag cca gac gca gaa      768
Leu Asp Asp Glu Pro Gly Val His Arg Val Trp Gln Pro Asp Ala Glu
                245                 250                 255

aca ccg ggg ctc gca atg tca aga gca ttc gga gac tac tgt att aaa      816
Thr Pro Gly Leu Ala Met Ser Arg Ala Phe Gly Asp Tyr Cys Ile Lys
            260                 265                 270

gag tat gga ttg gtc tca gtc cct gaa gtc act caa aga cac atc tct      864
Glu Tyr Gly Leu Val Ser Val Pro Glu Val Thr Gln Arg His Ile Ser
        275                 280                 285

act aaa gac cac ttc ata atc ttg gcc agt gat ggg ata tgg gat gtg      912
Thr Lys Asp His Phe Ile Ile Leu Ala Ser Asp Gly Ile Trp Asp Val
    290                 295                 300

atc tct aac caa gag gct ata gag att gtc tcc tca acg gct gag cgg      960
Ile Ser Asn Gln Glu Ala Ile Glu Ile Val Ser Ser Thr Ala Glu Arg
305                 310                 315                 320

cct aag gcg gct aag cga tta gta gag caa gcg gtt cgg gct tgg aag     1008
Pro Lys Ala Ala Lys Arg Leu Val Glu Gln Ala Val Arg Ala Trp Lys
                325                 330                 335

aaa aag aga cga gga tac tcc atg gat gat atg tca gtc gtc tgc ctc     1056
Lys Lys Arg Arg Gly Tyr Ser Met Asp Asp Met Ser Val Val Cys Leu
            340                 345                 350

ttc ctc cat tct tct tca tcg tca tct cta tca caa cat cat cat gcc     1104
Phe Leu His Ser Ser Ser Ser Ser Ser Leu Ser Gln His His His Ala
        355                 360                 365

atg acg att tta aag taa                                             1122
Met Thr Ile Leu Lys
    370
```

<210> SEQ ID NO 36
<211> LENGTH: 373
<212> TYPE: PRT
<213> ORGANISM: Arabidopsis thaliana

<400> SEQUENCE: 36

-continued

```
Met Gly His Phe Ser Ser Met Phe Asn Gly Leu Ala Arg Ser Phe Ser
1               5                   10                  15

Ile Lys Lys Val Lys Asn Asn Asn Gly Asn Cys Asp Ala Lys Glu Ala
            20                  25                  30

Ala Asp Glu Met Ala Ser Glu Ala Lys Lys Lys Glu Leu Ile Leu Lys
        35                  40                  45

Ser Ser Gly Tyr Val Asn Val Gln Gly Ser Asn Asn Leu Ala Ser Leu
    50                  55                  60

Phe Ser Lys Arg Gly Glu Lys Gly Val Asn Gln Asp Cys Ala Leu Val
65                  70                  75                  80

Trp Glu Gly Phe Gly Cys Gln Glu Asp Met Ile Phe Cys Gly Ile Phe
                85                  90                  95

Asp Gly His Gly Pro Trp Gly His Tyr Val Ala Lys Gln Val Arg Asn
            100                 105                 110

Ser Met Pro Leu Ser Leu Leu Cys Asn Trp Gln Lys Ile Leu Ala Gln
        115                 120                 125

Ala Thr Leu Glu Pro Glu Leu Asp Leu Glu Gly Ser Asn Lys Lys Ile
    130                 135                 140

Ser Arg Phe Asp Ile Trp Lys Gln Ser Tyr Leu Lys Thr Cys Ala Thr
145                 150                 155                 160

Val Asp Gln Glu Leu Glu His His Arg Lys Ile Asp Ser Tyr Tyr Ser
                165                 170                 175

Gly Thr Thr Ala Leu Thr Ile Val Arg Gln Gly Glu Val Ile Tyr Val
            180                 185                 190

Ala Asn Val Gly Asp Ser Arg Ala Val Leu Ala Met Glu Ser Asp Glu
        195                 200                 205

Gly Ser Leu Val Ala Val Gln Leu Thr Leu Asp Phe Lys Pro Asn Leu
    210                 215                 220

Pro Gln Glu Lys Glu Arg Ile Ile Gly Cys Lys Gly Arg Val Phe Cys
225                 230                 235                 240

Leu Asp Asp Glu Pro Gly Val His Arg Val Trp Gln Pro Asp Ala Glu
                245                 250                 255

Thr Pro Gly Leu Ala Met Ser Arg Ala Phe Gly Asp Tyr Cys Ile Lys
            260                 265                 270

Glu Tyr Gly Leu Val Ser Val Pro Glu Val Thr Gln Arg His Ile Ser
        275                 280                 285

Thr Lys Asp His Phe Ile Ile Leu Ala Ser Asp Gly Ile Trp Asp Val
    290                 295                 300

Ile Ser Asn Gln Glu Ala Ile Glu Ile Val Ser Ser Thr Ala Glu Arg
305                 310                 315                 320

Pro Lys Ala Ala Lys Arg Leu Val Glu Gln Ala Val Arg Ala Trp Lys
                325                 330                 335

Lys Lys Arg Arg Gly Tyr Ser Met Asp Asp Met Ser Val Val Cys Leu
            340                 345                 350

Phe Leu His Ser Ser Ser Ser Ser Ser Leu Ser Gln His His His Ala
        355                 360                 365

Met Thr Ile Leu Lys
    370
```

<210> SEQ ID NO 37
<211> LENGTH: 24
<212> TYPE: DNA
<213> ORGANISM: Artificial
<220> FEATURE:
<223> OTHER INFORMATION: Synthetic DNA -continued

<400> SEQUENCE: 37

```
atgggacatt tctcatcgat gttc                                             24
```

<210> SEQ ID NO 38
<211> LENGTH: 27
<212> TYPE: DNA
<213> ORGANISM: Artificial
<220> FEATURE:
<223> OTHER INFORMATION: Synthetic DNA

<400> SEQUENCE: 38

```
ttactttaaa atcgtcatgg catgatg                                          27
```

<210> SEQ ID NO 39
<211> LENGTH: 56
<212> TYPE: DNA
<213> ORGANISM: Artificial
<220> FEATURE:
<223> OTHER INFORMATION: Synthetic DNA

<400> SEQUENCE: 39

```
aattactatt tacaattaca gtcgacatgg gacatttctc atcgatgttc aatgga         56
```

<210> SEQ ID NO 40
<211> LENGTH: 59
<212> TYPE: DNA
<213> ORGANISM: Artificial
<220> FEATURE:
<223> OTHER INFORMATION: Synthetic DNA

<400> SEQUENCE: 40

```
agccgggcgg ccgctttact tgtacattac tttaaaatcg tcatggcatg atgatgttg      59
```

<210> SEQ ID NO 41
<211> LENGTH: 1584
<212> TYPE: DNA
<213> ORGANISM: Arabidopsis thaliana
<220> FEATURE:
<221> NAME/KEY: CDS
<222> LOCATION: (1)..(1584)

<400> SEQUENCE: 41

```
atg ggg tcc tgt tta tct gca gag agc agg agc cct aga ccg ggc tct       48
Met Gly Ser Cys Leu Ser Ala Glu Ser Arg Ser Pro Arg Pro Gly Ser
1               5                   10                  15

cct tgc tct cct gct ttt agt gtg agg aag agg aag aac tct aag aag       96
Pro Cys Ser Pro Ala Phe Ser Val Arg Lys Arg Lys Asn Ser Lys Lys
            20                  25                  30

cga cct ggt tct agg aac tct tcc ttt gat tac cgg aga gaa gaa ccg      144
Arg Pro Gly Ser Arg Asn Ser Ser Phe Asp Tyr Arg Arg Glu Glu Pro
        35                  40                  45

ttg aat cag gtt ccg ggc cgg atg ttc ttg aat gga tca act gag gtt      192
Leu Asn Gln Val Pro Gly Arg Met Phe Leu Asn Gly Ser Thr Glu Val
    50                  55                  60

gct tgt atc tac act caa caa ggc aag aaa ggg cct aat caa gat gcc      240
Ala Cys Ile Tyr Thr Gln Gln Gly Lys Lys Gly Pro Asn Gln Asp Ala
65                  70                  75                  80

atg gtt gtt tgg gag aat ttt ggt tcg agg aca gat aca atc ttc tgt      288
Met Val Val Trp Glu Asn Phe Gly Ser Arg Thr Asp Thr Ile Phe Cys
                85                  90                  95

gga gtg ttt gat gga cat ggt cca tat ggt cat atg gtt gca aag aga      336
Gly Val Phe Asp Gly His Gly Pro Tyr Gly His Met Val Ala Lys Arg
            100                 105                 110
```

```
gtc aga gac aat ctt cct ctc aaa tta agt gct tat tgg gaa gca aaa      384
Val Arg Asp Asn Leu Pro Leu Lys Leu Ser Ala Tyr Trp Glu Ala Lys
        115                 120                 125

gta cca gtt gaa ggt gtt ctt aag gca atc acc acc gac act gtc aat      432
Val Pro Val Glu Gly Val Leu Lys Ala Ile Thr Thr Asp Thr Val Asn
    130                 135                 140

aat gta acc aac att aac aac cct gaa gat gct gct gct gct gct gct      480
Asn Val Thr Asn Ile Asn Asn Pro Glu Asp Ala Ala Ala Ala Ala Ala
145                 150                 155                 160

ttt gtc act gct gaa gaa gaa cct agg aca tct gct gac atg gag gag      528
Phe Val Thr Ala Glu Glu Glu Pro Arg Thr Ser Ala Asp Met Glu Glu
                165                 170                 175

gag aac aca gaa acc caa ccg gaa ttg ttt caa acg ctg aaa gag tcg      576
Glu Asn Thr Glu Thr Gln Pro Glu Leu Phe Gln Thr Leu Lys Glu Ser
            180                 185                 190

ttt ctt aag gct ttt aaa gtt atg gat aga gag ctt aaa ttc cat gga      624
Phe Leu Lys Ala Phe Lys Val Met Asp Arg Glu Leu Lys Phe His Gly
        195                 200                 205

agt gtt gac tgt ttc tgc agt ggg aca aca gct gta acc ttg atc aag      672
Ser Val Asp Cys Phe Cys Ser Gly Thr Thr Ala Val Thr Leu Ile Lys
    210                 215                 220

cag ggt cag tat ctc gtt gtt gga aat gtt ggg gat tcc aga gct gta      720
Gln Gly Gln Tyr Leu Val Val Gly Asn Val Gly Asp Ser Arg Ala Val
225                 230                 235                 240

atg ggt aca aga gac agt gaa aat act ctt gtc gct gtt caa cta act      768
Met Gly Thr Arg Asp Ser Glu Asn Thr Leu Val Ala Val Gln Leu Thr
                245                 250                 255

gtg gat ctt aag cca aat ctc cca ggt tgg att atc tta tgt gaa tgt      816
Val Asp Leu Lys Pro Asn Leu Pro Gly Trp Ile Ile Leu Cys Glu Cys
            260                 265                 270

atg atg ttg tcc tgt gga tgt atg atg gat cca tta atc atg ttt att      864
Met Met Leu Ser Cys Gly Cys Met Met Asp Pro Leu Ile Met Phe Ile
        275                 280                 285

ggg ttt ttt ttt att ccc tca att gaa ctt gca gct gag gca gag aga      912
Gly Phe Phe Phe Ile Pro Ser Ile Glu Leu Ala Ala Glu Ala Glu Arg
    290                 295                 300

ata aga aag tgt cga gga cga gtg ttt gct ctt aga gat gaa cct gaa      960
Ile Arg Lys Cys Arg Gly Arg Val Phe Ala Leu Arg Asp Glu Pro Glu
305                 310                 315                 320

gtt tgt aga gtt tgg ctg cca aat tgt gac tca cct gga ctt gct atg     1008
Val Cys Arg Val Trp Leu Pro Asn Cys Asp Ser Pro Gly Leu Ala Met
                325                 330                 335

gca cgt gct ttt ggt gac ttt tgc ctt aaa gat ttt ggc cta atc tct     1056
Ala Arg Ala Phe Gly Asp Phe Cys Leu Lys Asp Phe Gly Leu Ile Ser
            340                 345                 350

gtg cct gat gta tct ttc cgt cag tta acc gaa aaa gat gag ttt ata     1104
Val Pro Asp Val Ser Phe Arg Gln Leu Thr Glu Lys Asp Glu Phe Ile
        355                 360                 365

gtg ttg gct aca gat ggg att tgg gat gtt ctc tca aat gaa gat gta     1152
Val Leu Ala Thr Asp Gly Ile Trp Asp Val Leu Ser Asn Glu Asp Val
    370                 375                 380

gtg gcg att gta gct tca gct cca tcg cgc tcc tct gca gca aga gct     1200
Val Ala Ile Val Ala Ser Ala Pro Ser Arg Ser Ser Ala Ala Arg Ala
385                 390                 395                 400

tta gtc gag tct gcg gtc aga gct tgg aga tac aaa tac ccg act tcc     1248
Leu Val Glu Ser Ala Val Arg Ala Trp Arg Tyr Lys Tyr Pro Thr Ser
                405                 410                 415

aaa gtc gat gac tgt gcc gct gtt tgc ttg tat cta gac tcc agc aac     1296
Lys Val Asp Asp Cys Ala Ala Val Cys Leu Tyr Leu Asp Ser Ser Asn
```

```
            420                 425                 430

aca aac gcc ata tct aca gct tct tcc atc tcc aaa ctt gaa gat gga     1344
Thr Asn Ala Ile Ser Thr Ala Ser Ser Ile Ser Lys Leu Glu Asp Gly
        435                 440                 445

gaa gaa gaa gaa cta aaa gcc acg act gag gat gat gat gca tca gga     1392
Glu Glu Glu Glu Leu Lys Ala Thr Thr Glu Asp Asp Asp Ala Ser Gly
    450                 455                 460

cca agc ggt cta ggc cgt tcg agt act gtc agg tcg ggg aaa gag att     1440
Pro Ser Gly Leu Gly Arg Ser Ser Thr Val Arg Ser Gly Lys Glu Ile
465                 470                 475                 480

gct ctc gac gaa agt gaa act gag aag ctg ata aaa gaa gcg gat aac     1488
Ala Leu Asp Glu Ser Glu Thr Glu Lys Leu Ile Lys Glu Ala Asp Asn
            485                 490                 495

ttg gat tca gaa cct gga aca gag tat tct gca ctt gaa ggt gtt gca     1536
Leu Asp Ser Glu Pro Gly Thr Glu Tyr Ser Ala Leu Glu Gly Val Ala
            500                 505                 510

aga gtt aat aca ctt tta aac tta cca aga ttt gtg cct gga aag tga     1584
Arg Val Asn Thr Leu Leu Asn Leu Pro Arg Phe Val Pro Gly Lys
        515                 520                 525


<210> SEQ ID NO 42
<211> LENGTH: 527
<212> TYPE: PRT
<213> ORGANISM: Arabidopsis thaliana

<400> SEQUENCE: 42

Met Gly Ser Cys Leu Ser Ala Glu Ser Arg Ser Pro Arg Pro Gly Ser
1               5                   10                  15

Pro Cys Ser Pro Ala Phe Ser Val Arg Lys Arg Lys Asn Ser Lys Lys
            20                  25                  30

Arg Pro Gly Ser Arg Asn Ser Ser Phe Asp Tyr Arg Arg Glu Glu Pro
        35                  40                  45

Leu Asn Gln Val Pro Gly Arg Met Phe Leu Asn Gly Ser Thr Glu Val
    50                  55                  60

Ala Cys Ile Tyr Thr Gln Gln Gly Lys Lys Gly Pro Asn Gln Asp Ala
65                  70                  75                  80

Met Val Val Trp Glu Asn Phe Gly Ser Arg Thr Asp Thr Ile Phe Cys
                85                  90                  95

Gly Val Phe Asp Gly His Gly Pro Tyr Gly His Met Val Ala Lys Arg
            100                 105                 110

Val Arg Asp Asn Leu Pro Leu Lys Leu Ser Ala Tyr Trp Glu Ala Lys
        115                 120                 125

Val Pro Val Glu Gly Val Leu Lys Ala Ile Thr Thr Asp Thr Val Asn
    130                 135                 140

Asn Val Thr Asn Ile Asn Asn Pro Glu Asp Ala Ala Ala Ala Ala Ala
145                 150                 155                 160

Phe Val Thr Ala Glu Glu Glu Pro Arg Thr Ser Ala Asp Met Glu Glu
                165                 170                 175

Glu Asn Thr Glu Thr Gln Pro Glu Leu Phe Gln Thr Leu Lys Glu Ser
            180                 185                 190

Phe Leu Lys Ala Phe Lys Val Met Asp Arg Glu Leu Lys Phe His Gly
        195                 200                 205

Ser Val Asp Cys Phe Cys Ser Gly Thr Thr Ala Val Thr Leu Ile Lys
    210                 215                 220

Gln Gly Gln Tyr Leu Val Val Gly Asn Val Gly Asp Ser Arg Ala Val
225                 230                 235                 240
```

-continued

```
Met Gly Thr Arg Asp Ser Glu Asn Thr Leu Val Ala Val Gln Leu Thr
                245                 250                 255

Val Asp Leu Lys Pro Asn Leu Pro Gly Trp Ile Ile Leu Cys Glu Cys
            260                 265                 270

Met Met Leu Ser Cys Gly Cys Met Met Asp Pro Leu Ile Met Phe Ile
        275                 280                 285

Gly Phe Phe Phe Ile Pro Ser Ile Glu Leu Ala Ala Glu Ala Glu Arg
    290                 295                 300

Ile Arg Lys Cys Arg Gly Arg Val Phe Ala Leu Arg Asp Glu Pro Glu
305                 310                 315                 320

Val Cys Arg Val Trp Leu Pro Asn Cys Asp Ser Pro Gly Leu Ala Met
                325                 330                 335

Ala Arg Ala Phe Gly Asp Phe Cys Leu Lys Asp Phe Gly Leu Ile Ser
            340                 345                 350

Val Pro Asp Val Ser Phe Arg Gln Leu Thr Glu Lys Asp Glu Phe Ile
        355                 360                 365

Val Leu Ala Thr Asp Gly Ile Trp Asp Val Leu Ser Asn Glu Asp Val
    370                 375                 380

Val Ala Ile Val Ala Ser Ala Pro Ser Arg Ser Ser Ala Ala Arg Ala
385                 390                 395                 400

Leu Val Glu Ser Ala Val Arg Ala Trp Arg Tyr Lys Tyr Pro Thr Ser
                405                 410                 415

Lys Val Asp Asp Cys Ala Ala Val Cys Leu Tyr Leu Asp Ser Ser Asn
            420                 425                 430

Thr Asn Ala Ile Ser Thr Ala Ser Ser Ile Ser Lys Leu Glu Asp Gly
        435                 440                 445

Glu Glu Glu Glu Leu Lys Ala Thr Thr Glu Asp Asp Asp Ala Ser Gly
    450                 455                 460

Pro Ser Gly Leu Gly Arg Ser Ser Thr Val Arg Ser Gly Lys Glu Ile
465                 470                 475                 480

Ala Leu Asp Glu Ser Glu Thr Glu Lys Leu Ile Lys Glu Ala Asp Asn
                485                 490                 495

Leu Asp Ser Glu Pro Gly Thr Glu Tyr Ser Ala Leu Glu Gly Val Ala
            500                 505                 510

Arg Val Asn Thr Leu Leu Asn Leu Pro Arg Phe Val Pro Gly Lys
        515                 520                 525
```

<210> SEQ ID NO 43
<211> LENGTH: 22
<212> TYPE: DNA
<213> ORGANISM: Artificial
<220> FEATURE:
<223> OTHER INFORMATION: Synthetic DNA

<400> SEQUENCE: 43
atggggtcct gtttatctgc ag 22

<210> SEQ ID NO 44
<211> LENGTH: 23
<212> TYPE: DNA
<213> ORGANISM: Artificial
<220> FEATURE:
<223> OTHER INFORMATION: Synthetic DNA

<400> SEQUENCE: 44
tcactttcca ggcacaaatc ttg 23

<210> SEQ ID NO 45
<211> LENGTH: 56
<212> TYPE: DNA
<213> ORGANISM: Artificial
<220> FEATURE:
<223> OTHER INFORMATION: Synthetic DNA

<400> SEQUENCE: 45
aattactatt tacaattaca gtcgacatgg ggtcctgttt atctgcagag agcagg 56

<210> SEQ ID NO 46
<211> LENGTH: 56
<212> TYPE: DNA
<213> ORGANISM: Artificial
<220> FEATURE:
<223> OTHER INFORMATION: Synthetic DNA

<400> SEQUENCE: 46
agccgggcgg ccgctttact tgtacatcac tttccaggca caaatcttgg taagtt 56

<210> SEQ ID NO 47
<211> LENGTH: 1056
<212> TYPE: DNA
<213> ORGANISM: Arabidopsis thaliana
<220> FEATURE:
<221> NAME/KEY: CDS
<222> LOCATION: (1)..(1056)

<400> SEQUENCE: 47

```
atg gtg ctt tta cca gcg ttt ttg gac gga tta gcg aga act gta tcg       48
Met Val Leu Leu Pro Ala Phe Leu Asp Gly Leu Ala Arg Thr Val Ser
1               5                   10                  15

acg aag aaa ggt aaa aaa cta tcg gaa gat gaa gat gga ggg aga gag       96
Thr Lys Lys Gly Lys Lys Leu Ser Glu Asp Glu Asp Gly Gly Arg Glu
            20                  25                  30

atc gca aaa tcg atg att aaa gat tcg aag aag aac tcg acg ttg ctc      144
Ile Ala Lys Ser Met Ile Lys Asp Ser Lys Lys Asn Ser Thr Leu Leu
        35                  40                  45

ggt act tca ggc ttt gtt agc tcc gaa agt tct aag agg ttt acc tct      192
Gly Thr Ser Gly Phe Val Ser Ser Glu Ser Ser Lys Arg Phe Thr Ser
    50                  55                  60

att tgt tct aat aga ggt gag aaa gga atc aac caa gat cgt gca att      240
Ile Cys Ser Asn Arg Gly Glu Lys Gly Ile Asn Gln Asp Arg Ala Ile
65                  70                  75                  80

gtt tgg gag gga ttt ggg tgc caa gaa gac ata aca ttt tgt ggg atg      288
Val Trp Glu Gly Phe Gly Cys Gln Glu Asp Ile Thr Phe Cys Gly Met
                85                  90                  95

ttt gat gga cat gga cca tgg gga cat gtg ata gcc aaa aga gta aaa      336
Phe Asp Gly His Gly Pro Trp Gly His Val Ile Ala Lys Arg Val Lys
            100                 105                 110

aaa tca ttt cca tct tct ctg ctt tgc caa tgg caa caa act ctt gcc      384
Lys Ser Phe Pro Ser Ser Leu Leu Cys Gln Trp Gln Gln Thr Leu Ala
        115                 120                 125

tcc tta tca tcc tcg ccg gaa tgt tcc tct ccg ttt gat ctt tgg aag      432
Ser Leu Ser Ser Ser Pro Glu Cys Ser Ser Pro Phe Asp Leu Trp Lys
    130                 135                 140

caa gct tgc ctg aaa aca ttc tcc atc atc gat ctt gat ctc aag atc      480
Gln Ala Cys Leu Lys Thr Phe Ser Ile Ile Asp Leu Asp Leu Lys Ile
145                 150                 155                 160

agt cct tcc att gat tct tac tgt agc ggc tgc acc gct ctc acc gct      528
Ser Pro Ser Ile Asp Ser Tyr Cys Ser Gly Cys Thr Ala Leu Thr Ala
                165                 170                 175

gtt ttg cag ggt gat cat ctc gtt ata gca aat gcg ggt gac tca cga      576
```

-continued

```
Val Leu Gln Gly Asp His Leu Val Ile Ala Asn Ala Gly Asp Ser Arg
            180                 185                 190

gca gta ata gca aca act tct gat gat gga aac ggt tta gtc ccg gtt      624
Ala Val Ile Ala Thr Thr Ser Asp Asp Gly Asn Gly Leu Val Pro Val
        195                 200                 205

cag ctc tcg gta gac ttt aaa cca aac att ccc gag gaa gca gaa cgg      672
Gln Leu Ser Val Asp Phe Lys Pro Asn Ile Pro Glu Glu Ala Glu Arg
    210                 215                 220

ata aaa caa tcg gat gga cga ttg ttc tgc cta gac gat gaa ccg gga      720
Ile Lys Gln Ser Asp Gly Arg Leu Phe Cys Leu Asp Asp Glu Pro Gly
225                 230                 235                 240

gtg tac cgg gtg ggt atg cct aat gga gga tca ctc ggt tta gct gtt      768
Val Tyr Arg Val Gly Met Pro Asn Gly Gly Ser Leu Gly Leu Ala Val
                245                 250                 255

tca aga gcg ttt gga gat tac tgc ctt aaa gac ttc ggt tta gtc tct      816
Ser Arg Ala Phe Gly Asp Tyr Cys Leu Lys Asp Phe Gly Leu Val Ser
            260                 265                 270

gaa ccg gaa gta aca tac cga aag ata acc gac aag gac cag ttt cta      864
Glu Pro Glu Val Thr Tyr Arg Lys Ile Thr Asp Lys Asp Gln Phe Leu
        275                 280                 285

atc ttg gcc acc gat ggg atg tgg gat gtg atg acg aat aat gag gca      912
Ile Leu Ala Thr Asp Gly Met Trp Asp Val Met Thr Asn Asn Glu Ala
    290                 295                 300

gtg gag ata gta aga gga gtt aaa gag aga aga aag agc gca aag aga      960
Val Glu Ile Val Arg Gly Val Lys Glu Arg Arg Lys Ser Ala Lys Arg
305                 310                 315                 320

ttg gta gag aga gct gtg acg ctt tgg cgt agg aag aga aga agc atc     1008
Leu Val Glu Arg Ala Val Thr Leu Trp Arg Arg Lys Arg Arg Ser Ile
                325                 330                 335

gcc atg gat gat att tct gtt ctc tgt ctc ttc ttt cgt cct tct tag     1056
Ala Met Asp Asp Ile Ser Val Leu Cys Leu Phe Phe Arg Pro Ser
            340                 345                 350


<210> SEQ ID NO 48
<211> LENGTH: 351
<212> TYPE: PRT
<213> ORGANISM: Arabidopsis thaliana

<400> SEQUENCE: 48

Met Val Leu Leu Pro Ala Phe Leu Asp Gly Leu Ala Arg Thr Val Ser
1               5                   10                  15

Thr Lys Lys Gly Lys Lys Leu Ser Glu Asp Glu Asp Gly Gly Arg Glu
            20                  25                  30

Ile Ala Lys Ser Met Ile Lys Asp Ser Lys Lys Asn Ser Thr Leu Leu
        35                  40                  45

Gly Thr Ser Gly Phe Val Ser Ser Glu Ser Ser Lys Arg Phe Thr Ser
    50                  55                  60

Ile Cys Ser Asn Arg Gly Glu Lys Gly Ile Asn Gln Asp Arg Ala Ile
65                  70                  75                  80

Val Trp Glu Gly Phe Gly Cys Gln Glu Asp Ile Thr Phe Cys Gly Met
                85                  90                  95

Phe Asp Gly His Gly Pro Trp Gly His Val Ile Ala Lys Arg Val Lys
            100                 105                 110

Lys Ser Phe Pro Ser Ser Leu Leu Cys Gln Trp Gln Gln Thr Leu Ala
        115                 120                 125

Ser Leu Ser Ser Ser Pro Glu Cys Ser Ser Pro Phe Asp Leu Trp Lys
    130                 135                 140

Gln Ala Cys Leu Lys Thr Phe Ser Ile Ile Asp Leu Asp Leu Lys Ile
```

-continued

```
145                 150                 155                 160

Ser Pro Ser Ile Asp Ser Tyr Cys Ser Gly Cys Thr Ala Leu Thr Ala
                165                 170                 175

Val Leu Gln Gly Asp His Leu Val Ile Ala Asn Ala Gly Asp Ser Arg
            180                 185                 190

Ala Val Ile Ala Thr Thr Ser Asp Asp Gly Asn Gly Leu Val Pro Val
        195                 200                 205

Gln Leu Ser Val Asp Phe Lys Pro Asn Ile Pro Glu Glu Ala Glu Arg
    210                 215                 220

Ile Lys Gln Ser Asp Gly Arg Leu Phe Cys Leu Asp Asp Glu Pro Gly
225                 230                 235                 240

Val Tyr Arg Val Gly Met Pro Asn Gly Gly Ser Leu Gly Leu Ala Val
                245                 250                 255

Ser Arg Ala Phe Gly Asp Tyr Cys Leu Lys Asp Phe Gly Leu Val Ser
            260                 265                 270

Glu Pro Glu Val Thr Tyr Arg Lys Ile Thr Asp Lys Asp Gln Phe Leu
        275                 280                 285

Ile Leu Ala Thr Asp Gly Met Trp Asp Val Met Thr Asn Asn Glu Ala
    290                 295                 300

Val Glu Ile Val Arg Gly Val Lys Glu Arg Arg Lys Ser Ala Lys Arg
305                 310                 315                 320

Leu Val Glu Arg Ala Val Thr Leu Trp Arg Arg Lys Arg Arg Ser Ile
                325                 330                 335

Ala Met Asp Asp Ile Ser Val Leu Cys Leu Phe Phe Arg Pro Ser
            340                 345                 350
```

<210> SEQ ID NO 49
<211> LENGTH: 24
<212> TYPE: DNA
<213> ORGANISM: Artificial
<220> FEATURE:
<223> OTHER INFORMATION: Synthetic DNA

<400> SEQUENCE: 49
atggtgcttt taccagcgtt tttg 24

<210> SEQ ID NO 50
<211> LENGTH: 23
<212> TYPE: DNA
<213> ORGANISM: Artificial
<220> FEATURE:
<223> OTHER INFORMATION: Synthetic DNA

<400> SEQUENCE: 50
ctaagaagga cgaaagaaga gac 23

<210> SEQ ID NO 51
<211> LENGTH: 60
<212> TYPE: DNA
<213> ORGANISM: Artificial
<220> FEATURE:
<223> OTHER INFORMATION: Synthetic DNA

<400> SEQUENCE: 51
aattactatt tacaattaca gtcgacatgg tgcttttacc agcgtttttg gacggattag 60

<210> SEQ ID NO 52
<211> LENGTH: 56
<212> TYPE: DNA
<213> ORGANISM: Artificial

```
<220> FEATURE:
<223> OTHER INFORMATION: Synthetic DNA

<400> SEQUENCE: 52

agccgggcgg ccgctttact tgtacactaa gaaggacgaa agaagagaca gagaac         56


<210> SEQ ID NO 53
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
      or preferably L or F
<220> FEATURE:
<221> NAME/KEY: misc_feature
<222> LOCATION: (4)..(4)
<223> OTHER INFORMATION: Xaa can be any naturally occurring amino acid,
      or preferably V, I or M
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably V or I
<220> FEATURE:
<221> NAME/KEY: misc_feature
<222> LOCATION: (16)..(16)
<223> OTHER INFORMATION: Xaa can be any naturally occurring amino acid,
      or preferably S or A
<220> FEATURE:
<221> NAME/KEY: misc_feature
<222> LOCATION: (17)..(17)
<223> OTHER INFORMATION: Xaa can be any naturally occurring amino acid,
      or preferably K or R
<220> FEATURE:
<221> NAME/KEY: misc_feature
<222> LOCATION: (18)..(18)
<223> OTHER INFORMATION: Xaa can be any naturally occurring amino acid

<400> SEQUENCE: 53

Xaa Cys Gly Xaa Phe Asp Gly His Gly Xaa Xaa Gly Xaa Xaa Xaa Xaa
1               5                   10                  15

Xaa Xaa Val


<210> SEQ ID NO 54
<211> LENGTH: 27
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid,
      or preferably T, C or S
<220> FEATURE:
<221> NAME/KEY: misc_feature
<222> LOCATION: (5)..(5)
<223> OTHER INFORMATION: Xaa can be any naturally occurring amino acid,
      or preferably G, A or S
<220> FEATURE:
<221> NAME/KEY: misc_feature
<222> LOCATION: (6)..(6)
```

<223> OTHER INFORMATION: Xaa can be any naturally occurring amino acid, or preferably V or L
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid, or preferably I, V, F or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid, or preferably G or A
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid, or preferably L, V or I
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid, or preferably I, V or M
<220> FEATURE:
<221> NAME/KEY: misc_feature
<222> LOCATION: (18)..(18)
<223> OTHER INFORMATION: Xaa can be any naturally occurring amino acid, or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid, or preferably D or H
<220> FEATURE:
<221> NAME/KEY: misc_feature
<222> LOCATION: (26)..(26)
<223> OTHER INFORMATION: Xaa can be any naturally occurring amino acid, or preferably V or I
<220> FEATURE:
<221> NAME/KEY: misc_feature
<222> LOCATION: (27)..(27)
<223> OTHER INFORMATION: Xaa can be any naturally occurring amino acid, or preferably L, M or I

<400> SEQUENCE: 54

```
Ser Gly Xaa Thr Xaa Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25
```

<210> SEQ ID NO 55
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:

<221> NAME/KEY: misc_feature
<222> LOCATION: (4)..(4)
<223> OTHER INFORMATION: Xaa can be any naturally occurring amino acid,
or preferably M or V
<220> FEATURE:
<221> NAME/KEY: misc_feature
<222> LOCATION: (5)..(5)
<223> OTHER INFORMATION: Xaa can be any naturally occurring amino acid,
or preferably S or A
<220> FEATURE:
<221> NAME/KEY: misc_feature
<222> LOCATION: (7)..(7)
<223> OTHER INFORMATION: Xaa can be any naturally occurring amino acid,
or preferably A or S
<220> FEATURE:
<221> NAME/KEY: misc_feature
<222> LOCATION: (8)..(8)
<223> OTHER INFORMATION: Xaa can be any naturally occurring amino acid,
or preferably F or L
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid,
or preferably L, I or V
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid,
or preferably Y, F or H
<220> FEATURE:
<221> NAME/KEY: misc_feature
<222> LOCATION: (18)..(18)
<223> OTHER INFORMATION: Xaa can be any naturally occurring amino acid,
or preferably V or L
<220> FEATURE:
<221> NAME/KEY: misc_feature
<222> LOCATION: (19)..(19)
<223> OTHER INFORMATION: Xaa can be any naturally occurring amino acid,
or preferably I or V
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
or preferably E, Q or D
<220> FEATURE:
<221> NAME/KEY: misc_feature
<222> LOCATION: (24)..(24)
<223> OTHER INFORMATION: Xaa can be any naturally occurring amino acid,
or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
or preferably I, L or V
<220> FEATURE:
<221> NAME/KEY: misc_feature
<222> LOCATION: (30)..(30)
<223> OTHER INFORMATION: Xaa can be any naturally occurring amino acid,
or preferably T or S
<220> FEATURE:
<221> NAME/KEY: misc_feature
<222> LOCATION: (31)..(32)
<223> OTHER INFORMATION: Xaa can be any naturally occurring amino acid -continued
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid, or preferably F or Y
<220> FEATURE:
<221> NAME/KEY: misc_feature
<222> LOCATION: (36)..(36)
<223> OTHER INFORMATION: Xaa can be any naturally occurring amino acid, or preferably L, I, V or M
<220> FEATURE:
<221> NAME/KEY: misc_feature
<222> LOCATION: (37)..(37)
<223> OTHER INFORMATION: Xaa can be any naturally occurring amino acid, or preferably V, L or I
<220> FEATURE:
<221> NAME/KEY: misc_feature
<222> LOCATION: (40)..(40)
<223> OTHER INFORMATION: Xaa can be any naturally occurring amino acid, or preferably T or S
<220> FEATURE:
<221> NAME/KEY: misc_feature
<222> LOCATION: (43)..(43)
<223> OTHER INFORMATION: Xaa can be any naturally occurring amino acid, or preferably V, I or M
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid, or preferably L, I, V or M
<220> FEATURE:
<221> NAME/KEY: misc_feature
<222> LOCATION: (48)..(48)
<223> OTHER INFORMATION: Xaa can be any naturally occurring amino acid, or preferably S or T
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid, or preferably E or D
<220> FEATURE:
<221> NAME/KEY: misc_feature
<222> LOCATION: (52)..(52)
<223> OTHER INFORMATION: Xaa can be any naturally occurring amino acid, or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid, or preferably L, V or I
<220> FEATURE:
<221> NAME/KEY: misc_feature
<222> LOCATION: (56)..(56)
<223> OTHER INFORMATION: Xaa can be any naturally occurring amino acid, or preferably I or V

<400> SEQUENCE: 55

```
Gly Leu Ala Xaa Xaa Arg Xaa Xaa Gly Asp Xaa Xaa Xaa Lys Xaa Xaa
1               5                   10                  15

Gly Xaa Xaa Xaa Xaa Pro Xaa Xaa Xaa Xaa Xaa Xaa Xaa Xaa Xaa Xaa
            20                  25                  30
```

```
Asp Xaa Xaa Xaa Xaa Leu Ala Xaa Asp Gly Xaa Trp Asp Xaa Xaa Xaa
        35                  40                  45

Asn Xaa Xaa Xaa Xaa Xaa Xaa Xaa
    50                  55


<210> SEQ ID NO 56
<211> LENGTH: 3261
<212> TYPE: DNA
<213> ORGANISM: Oryza sativa
<220> FEATURE:
<221> NAME/KEY: CDS
<222> LOCATION: (1)..(3261)

<400> SEQUENCE: 56

atg ggc tgc tca cct tct aag gtg tgt tca tgt cca cat tat aag ggc       48
Met Gly Cys Ser Pro Ser Lys Val Cys Ser Cys Pro His Tyr Lys Gly
1               5                   10                  15

agt ttg tgc ttc tgt gac tgt gga tgc ttt gga caa aca cct gac tcc       96
Ser Leu Cys Phe Cys Asp Cys Gly Cys Phe Gly Gln Thr Pro Asp Ser
            20                  25                  30

cca aga gag tca agg gga aaa tca aac cgg gtt agg gga aag aca gat      144
Pro Arg Glu Ser Arg Gly Lys Ser Asn Arg Val Arg Gly Lys Thr Asp
        35                  40                  45

tct agt gct tca gat gct tct tct gat gac cta gag gaa gat gat gat      192
Ser Ser Ala Ser Asp Ala Ser Ser Asp Asp Leu Glu Glu Asp Asp Asp
    50                  55                  60

gga ttg cac caa atg aac att aca agg gac tct aat gtt ggt atc aat      240
Gly Leu His Gln Met Asn Ile Thr Arg Asp Ser Asn Val Gly Ile Asn
65                  70                  75                  80

cga ctc tca agg gtc tca tca caa ttt ctt cca cca gaa ggt tca cgt      288
Arg Leu Ser Arg Val Ser Ser Gln Phe Leu Pro Pro Glu Gly Ser Arg
                85                  90                  95

aaa gtt cga atc cca ttg ggg aat tat gac ctg aga tat tcc tac ttg      336
Lys Val Arg Ile Pro Leu Gly Asn Tyr Asp Leu Arg Tyr Ser Tyr Leu
            100                 105                 110

tct caa aga ggc tac tac cca gaa tca ttg gac aag cca aac caa gac      384
Ser Gln Arg Gly Tyr Tyr Pro Glu Ser Leu Asp Lys Pro Asn Gln Asp
        115                 120                 125

agt ttt tgt ata cat act cca ttt gga aca agc cct gat gac cat ttc      432
Ser Phe Cys Ile His Thr Pro Phe Gly Thr Ser Pro Asp Asp His Phe
    130                 135                 140

ttt ggt gta ttt gat ggc cat gga gaa tat gga gct cag tgc tca caa      480
Phe Gly Val Phe Asp Gly His Gly Glu Tyr Gly Ala Gln Cys Ser Gln
145                 150                 155                 160

ttt gta aag cga aga cta tgc gaa aac ctg ctc aga gat gac cgg ttc      528
Phe Val Lys Arg Arg Leu Cys Glu Asn Leu Leu Arg Asp Asp Arg Phe
                165                 170                 175

cgt act gat gtt gtt cag gct ctt cat tct gct ttc ttg gca aca aat      576
Arg Thr Asp Val Val Gln Ala Leu His Ser Ala Phe Leu Ala Thr Asn
            180                 185                 190

tca cag ctt cat gca gac agc tta gat gat tct atg agt ggt act act      624
Ser Gln Leu His Ala Asp Ser Leu Asp Asp Ser Met Ser Gly Thr Thr
        195                 200                 205

gca gtc act gtg ctg gtg agg ggt aaa act att tac att gcg aat acg      672
Ala Val Thr Val Leu Val Arg Gly Lys Thr Ile Tyr Ile Ala Asn Thr
    210                 215                 220

ggt gat tca cgt gct gtt att gcc gaa aaa aga ggg gaa gat gtt gtt      720
Gly Asp Ser Arg Ala Val Ile Ala Glu Lys Arg Gly Glu Asp Val Val
225                 230                 235                 240

gct gtt gac ctg tcc ata gat caa aca ccc tac agg act gat gag ctt      768
```

-continued

Ala Val Asp Leu Ser Ile Asp Gln Thr Pro Tyr Arg Thr Asp Glu Leu
245 250 255 gaa agg gtc aag gag tgt ggt gct agg gtt atg acg ttg gat cag ata 816
Glu Arg Val Lys Glu Cys Gly Ala Arg Val Met Thr Leu Asp Gln Ile
260 265 270 gag ggg cta aag aac cca gat gta cag tgt tgg ggc acc gag gaa agt 864
Glu Gly Leu Lys Asn Pro Asp Val Gln Cys Trp Gly Thr Glu Glu Ser
275 280 285 gat gac ggt gat cct cca agg ttg tgg gtg caa aat ggc atg tat cca 912
Asp Asp Gly Asp Pro Pro Arg Leu Trp Val Gln Asn Gly Met Tyr Pro
290 295 300 gga act gct ttt act cgc agc att gga gat tct gtc gct gaa tct atc 960
Gly Thr Ala Phe Thr Arg Ser Ile Gly Asp Ser Val Ala Glu Ser Ile
305 310 315 320 ggt gtt gtc gct aat cct gag att ttt atc ctg gag ctc aat gcc aac 1008
Gly Val Val Ala Asn Pro Glu Ile Phe Ile Leu Glu Leu Asn Ala Asn
325 330 335 cat cca ttc ttt gtt ctt gct agt gat gga gtt ttt gag ttt ctt tct 1056
His Pro Phe Phe Val Leu Ala Ser Asp Gly Val Phe Glu Phe Leu Ser
340 345 350 agt caa act gtt gtc gac atg att gct aaa tac aag gat cct cgt gat 1104
Ser Gln Thr Val Val Asp Met Ile Ala Lys Tyr Lys Asp Pro Arg Asp
355 360 365 gcg tgc gct gca att gtt gct gaa tcc tat cgc ctc tgg cta cag tat 1152
Ala Cys Ala Ala Ile Val Ala Glu Ser Tyr Arg Leu Trp Leu Gln Tyr
370 375 380 gaa act cgt aca gat gac att aca ata ata gtt gtt cat att aac ggg 1200
Glu Thr Arg Thr Asp Asp Ile Thr Ile Ile Val Val His Ile Asn Gly
385 390 395 400 tta act gat atg gaa tgt act caa act gta atg aaa gta tct tta caa 1248
Leu Thr Asp Met Glu Cys Thr Gln Thr Val Met Lys Val Ser Leu Gln
405 410 415 cct tcc caa caa gtc gta gaa ttg gta ggc tca gaa tca cca tcg aca 1296
Pro Ser Gln Gln Val Val Glu Leu Val Gly Ser Glu Ser Pro Ser Thr
420 425 430 ata agt ttg aat ccc aag aac cag cgt tcc agg caa gat cta tca cgt 1344
Ile Ser Leu Asn Pro Lys Asn Gln Arg Ser Arg Gln Asp Leu Ser Arg
435 440 445 gct cgg ctg aga gca ctt gaa agt tcc ctg gaa aat ggt cga cta tgg 1392
Ala Arg Leu Arg Ala Leu Glu Ser Ser Leu Glu Asn Gly Arg Leu Trp
450 455 460 gtc cct cca tcc cca tcg cat cgg aag aca tgg gaa gag caa gca cat 1440
Val Pro Pro Ser Pro Ser His Arg Lys Thr Trp Glu Glu Gln Ala His
465 470 475 480 att gag cga ata cta cac gac cat ttc ctc ttc agg aag ctc act gac 1488
Ile Glu Arg Ile Leu His Asp His Phe Leu Phe Arg Lys Leu Thr Asp
485 490 495 tca cag tgc cat gtt tta ctt gat tgc atg caa aga gtt gag gtg aaa 1536
Ser Gln Cys His Val Leu Leu Asp Cys Met Gln Arg Val Glu Val Lys
500 505 510 gct ggg gat ata gtg gtg cag cag ggc ggt gaa ggc gag tgc ttc tat 1584
Ala Gly Asp Ile Val Val Gln Gln Gly Gly Glu Gly Glu Cys Phe Tyr
515 520 525 gta gtt ggg agt ggt gag ttt gaa gtg cta gcc att cag gaa gaa gat 1632
Val Val Gly Ser Gly Glu Phe Glu Val Leu Ala Ile Gln Glu Glu Asp
530 535 540 gga aag gaa gtt aca aag gtt cta cat cgg tat act gct gac aaa cta 1680
Gly Lys Glu Val Thr Lys Val Leu His Arg Tyr Thr Ala Asp Lys Leu
545 550 555 560

-continued

```
tct tct ttt ggg gag cta gca cta atg tat aat aaa cca ctt caa gct      1728
Ser Ser Phe Gly Glu Leu Ala Leu Met Tyr Asn Lys Pro Leu Gln Ala
                565                 570                 575

tca gtc cgt gct gtg act act gga act tta tgg gct cta aag cga gag      1776
Ser Val Arg Ala Val Thr Thr Gly Thr Leu Trp Ala Leu Lys Arg Glu
            580                 585                 590

gat ttt cgg gga att ctg atg tca gag ttt tca aat ata cca tca tta      1824
Asp Phe Arg Gly Ile Leu Met Ser Glu Phe Ser Asn Ile Pro Ser Leu
        595                 600                 605

aag ttg ctc cga tca gtg gag ctg ttt acg aga ttg aca atg ctt caa      1872
Lys Leu Leu Arg Ser Val Glu Leu Phe Thr Arg Leu Thr Met Leu Gln
    610                 615                 620

cta agt caa ctt gct gat tct ctt gtt gaa gta act ttt ggg gat ggt      1920
Leu Ser Gln Leu Ala Asp Ser Leu Val Glu Val Thr Phe Gly Asp Gly
625                 630                 635                 640

caa atg ata gta gac aag aat gat gat gca tct tcc ttg tat att att      1968
Gln Met Ile Val Asp Lys Asn Asp Asp Ala Ser Ser Leu Tyr Ile Ile
                645                 650                 655

caa aga ggt cgt gtg aaa ctt aaa ttg gct gca gat cag gta aat tca      2016
Gln Arg Gly Arg Val Lys Leu Lys Leu Ala Ala Asp Gln Val Asn Ser
            660                 665                 670

gat gcc tgg gat ctt ctt agt tct caa aca aag gtg gcc caa tca agt      2064
Asp Ala Trp Asp Leu Leu Ser Ser Gln Thr Lys Val Ala Gln Ser Ser
        675                 680                 685

cga gaa gat ggt aat tac gtg ttt gag ata gat gaa ggg gga cac ttt      2112
Arg Glu Asp Gly Asn Tyr Val Phe Glu Ile Asp Glu Gly Gly His Phe
    690                 695                 700

gga gag tgg gct ctc ttt ggg gag aca att gct ttt act gct atg tca      2160
Gly Glu Trp Ala Leu Phe Gly Glu Thr Ile Ala Phe Thr Ala Met Ser
705                 710                 715                 720

gtt ggt gat gtg act tgt tct act att gca aag gag aag ttt gac tca      2208
Val Gly Asp Val Thr Cys Ser Thr Ile Ala Lys Glu Lys Phe Asp Ser
                725                 730                 735

att att ggg ccc ttg cca aaa gtt tcc cag tct gat tcc aag ctc aaa      2256
Ile Ile Gly Pro Leu Pro Lys Val Ser Gln Ser Asp Ser Lys Leu Lys
            740                 745                 750

gat tcc ttg gtt cct aaa ggg cat ggt gca gat gat agt tcc ttc agg      2304
Asp Ser Leu Val Pro Lys Gly His Gly Ala Asp Asp Ser Ser Phe Arg
        755                 760                 765

aag gcg cag cta tct gat ttg gaa tgg aaa atg tgc ata tat gcc gct      2352
Lys Ala Gln Leu Ser Asp Leu Glu Trp Lys Met Cys Ile Tyr Ala Ala
    770                 775                 780

gat tgc agt gag att ggt ctt gtc caa cta aga ggt tct gac aag atc      2400
Asp Cys Ser Glu Ile Gly Leu Val Gln Leu Arg Gly Ser Asp Lys Ile
785                 790                 795                 800

aaa agc tta aag agg ttt tac atc aag aga gta aaa gac ctt cat aag      2448
Lys Ser Leu Lys Arg Phe Tyr Ile Lys Arg Val Lys Asp Leu His Lys
                805                 810                 815

gaa aaa cac gta ttt gat gag aag gat ctc atg aaa tct ttg agc caa      2496
Glu Lys His Val Phe Asp Glu Lys Asp Leu Met Lys Ser Leu Ser Gln
            820                 825                 830

tca act tgt gtg cca gaa gtt cta tgt act tgc gct gat caa tcc tac      2544
Ser Thr Cys Val Pro Glu Val Leu Cys Thr Cys Ala Asp Gln Ser Tyr
        835                 840                 845

cta gga ata ctg ctg aat tgt tgc ctt tgt tgc tca ctg gct tca ata      2592
Leu Gly Ile Leu Leu Asn Cys Cys Leu Cys Cys Ser Leu Ala Ser Ile
    850                 855                 860

ctt cat gca cca cta aat gag tcg tct gca cga ttc tat gca gcc tct      2640
Leu His Ala Pro Leu Asn Glu Ser Ser Ala Arg Phe Tyr Ala Ala Ser
865                 870                 875                 880
```

-continued

```
gtc gtc gta gcg cta gaa aat ctc cat cag agg tcc att ctt tac aga     2688
Val Val Val Ala Leu Glu Asn Leu His Gln Arg Ser Ile Leu Tyr Arg
                885                 890                 895

ggt gtt tct gca gac att ctt atg gtc gac cga tca ggg cat ctt caa     2736
Gly Val Ser Ala Asp Ile Leu Met Val Asp Arg Ser Gly His Leu Gln
            900                 905                 910

cta gtt gac ttc agg ttt gca aag aag ttg caa ggt gaa agg act tac     2784
Leu Val Asp Phe Arg Phe Ala Lys Lys Leu Gln Gly Glu Arg Thr Tyr
        915                 920                 925

aca ata tgt ggg att gcc gac tct cta gct cca gag ata gtt ctt ggt     2832
Thr Ile Cys Gly Ile Ala Asp Ser Leu Ala Pro Glu Ile Val Leu Gly
    930                 935                 940

agg ggc cat gga ttt tct gct gac tgg tgg gcg ctg gga gtg ttg att     2880
Arg Gly His Gly Phe Ser Ala Asp Trp Trp Ala Leu Gly Val Leu Ile
945                 950                 955                 960

tat ttc atg ctg caa tca gac atg cca ttt ggc tct tgg agg gag agt     2928
Tyr Phe Met Leu Gln Ser Asp Met Pro Phe Gly Ser Trp Arg Glu Ser
                965                 970                 975

gaa ctg gaa cct ttt gca aag att gcc aag ggt cac ctt gtc atg cca     2976
Glu Leu Glu Pro Phe Ala Lys Ile Ala Lys Gly His Leu Val Met Pro
            980                 985                 990

tca aca ttc agc atc gaa gtt gtt  gac ctt att aca aag  cta ctc gag   3024
Ser Thr Phe Ser Ile Glu Val Val  Asp Leu Ile Thr Lys  Leu Leu Glu
        995                 1000                 1005

gta aac  gaa aat gcg cgc ctt  ggg gcc aag gga gcg  gaa tct gtg      3069
Val Asn  Glu Asn Ala Arg Leu  Gly Ala Lys Gly Ala  Glu Ser Val
    1010                 1015                 1020

aaa aga  cac ccc tgg ttt gat  ggc att gac tgg aaa  caa ata gca      3114
Lys Arg  His Pro Trp Phe Asp  Gly Ile Asp Trp Lys  Gln Ile Ala
    1025                 1030                 1035

gat ggt  act tat aca gta ccc  caa gaa atc acc gat  cgt gtc gac      3159
Asp Gly  Thr Tyr Thr Val Pro  Gln Glu Ile Thr Asp  Arg Val Asp
    1040                 1045                 1050

agc tat  gta gaa act ctt aca  gag gac ttg aca gca  tcc cct tcc      3204
Ser Tyr  Val Glu Thr Leu Thr  Glu Asp Leu Thr Ala  Ser Pro Ser
    1055                 1060                 1065

atg cca  agt gaa gaa aca gct  gat cag gct gct cca  gaa tgg atc      3249
Met Pro  Ser Glu Glu Thr Ala  Asp Gln Ala Ala Pro  Glu Trp Ile
    1070                 1075                 1080

cag gat  tgg tga                                                    3261
Gln Asp  Trp
    1085


<210> SEQ ID NO 57
<211> LENGTH: 1086
<212> TYPE: PRT
<213> ORGANISM: Oryza sativa

<400> SEQUENCE: 57

Met Gly Cys Ser Pro Ser Lys Val Cys Ser Cys Pro His Tyr Lys Gly
1               5                   10                  15

Ser Leu Cys Phe Cys Asp Cys Gly Cys Phe Gly Gln Thr Pro Asp Ser
            20                  25                  30

Pro Arg Glu Ser Arg Gly Lys Ser Asn Arg Val Arg Gly Lys Thr Asp
        35                  40                  45

Ser Ser Ala Ser Asp Ala Ser Ser Asp Asp Leu Glu Glu Asp Asp Asp
    50                  55                  60

Gly Leu His Gln Met Asn Ile Thr Arg Asp Ser Asn Val Gly Ile Asn
65                  70                  75                  80
```

-continued

```
Arg Leu Ser Arg Val Ser Ser Gln Phe Leu Pro Pro Glu Gly Ser Arg
                85                  90                  95

Lys Val Arg Ile Pro Leu Gly Asn Tyr Asp Leu Arg Tyr Ser Tyr Leu
            100                 105                 110

Ser Gln Arg Gly Tyr Tyr Pro Glu Ser Leu Asp Lys Pro Asn Gln Asp
        115                 120                 125

Ser Phe Cys Ile His Thr Pro Phe Gly Thr Ser Pro Asp Asp His Phe
    130                 135                 140

Phe Gly Val Phe Asp Gly His Gly Glu Tyr Gly Ala Gln Cys Ser Gln
145                 150                 155                 160

Phe Val Lys Arg Arg Leu Cys Glu Asn Leu Leu Arg Asp Asp Arg Phe
                165                 170                 175

Arg Thr Asp Val Val Gln Ala Leu His Ser Ala Phe Leu Ala Thr Asn
            180                 185                 190

Ser Gln Leu His Ala Asp Ser Leu Asp Asp Ser Met Ser Gly Thr Thr
        195                 200                 205

Ala Val Thr Val Leu Val Arg Gly Lys Thr Ile Tyr Ile Ala Asn Thr
    210                 215                 220

Gly Asp Ser Arg Ala Val Ile Ala Glu Lys Arg Gly Glu Asp Val Val
225                 230                 235                 240

Ala Val Asp Leu Ser Ile Asp Gln Thr Pro Tyr Arg Thr Asp Glu Leu
                245                 250                 255

Glu Arg Val Lys Glu Cys Gly Ala Arg Val Met Thr Leu Asp Gln Ile
            260                 265                 270

Glu Gly Leu Lys Asn Pro Asp Val Gln Cys Trp Gly Thr Glu Glu Ser
        275                 280                 285

Asp Asp Gly Asp Pro Pro Arg Leu Trp Val Gln Asn Gly Met Tyr Pro
    290                 295                 300

Gly Thr Ala Phe Thr Arg Ser Ile Gly Asp Ser Val Ala Glu Ser Ile
305                 310                 315                 320

Gly Val Val Ala Asn Pro Glu Ile Phe Ile Leu Glu Leu Asn Ala Asn
                325                 330                 335

His Pro Phe Phe Val Leu Ala Ser Asp Gly Val Phe Glu Phe Leu Ser
            340                 345                 350

Ser Gln Thr Val Val Asp Met Ile Ala Lys Tyr Lys Asp Pro Arg Asp
        355                 360                 365

Ala Cys Ala Ala Ile Val Ala Glu Ser Tyr Arg Leu Trp Leu Gln Tyr
    370                 375                 380

Glu Thr Arg Thr Asp Asp Ile Thr Ile Ile Val Val His Ile Asn Gly
385                 390                 395                 400

Leu Thr Asp Met Glu Cys Thr Gln Thr Val Met Lys Val Ser Leu Gln
                405                 410                 415

Pro Ser Gln Gln Val Val Glu Leu Val Gly Ser Glu Ser Pro Ser Thr
            420                 425                 430

Ile Ser Leu Asn Pro Lys Asn Gln Arg Ser Arg Gln Asp Leu Ser Arg
        435                 440                 445

Ala Arg Leu Arg Ala Leu Glu Ser Ser Leu Glu Asn Gly Arg Leu Trp
    450                 455                 460

Val Pro Pro Ser Pro Ser His Arg Lys Thr Trp Glu Glu Gln Ala His
465                 470                 475                 480

Ile Glu Arg Ile Leu His Asp His Phe Leu Phe Arg Lys Leu Thr Asp
                485                 490                 495
```

-continued

```
Ser Gln Cys His Val Leu Leu Asp Cys Met Gln Arg Val Glu Val Lys
            500                 505                 510

Ala Gly Asp Ile Val Val Gln Gln Gly Gly Glu Gly Glu Cys Phe Tyr
        515                 520                 525

Val Val Gly Ser Gly Glu Phe Glu Val Leu Ala Ile Gln Glu Glu Asp
    530                 535                 540

Gly Lys Glu Val Thr Lys Val Leu His Arg Tyr Thr Ala Asp Lys Leu
545                 550                 555                 560

Ser Ser Phe Gly Glu Leu Ala Leu Met Tyr Asn Lys Pro Leu Gln Ala
                565                 570                 575

Ser Val Arg Ala Val Thr Thr Gly Thr Leu Trp Ala Leu Lys Arg Glu
            580                 585                 590

Asp Phe Arg Gly Ile Leu Met Ser Glu Phe Ser Asn Ile Pro Ser Leu
        595                 600                 605

Lys Leu Leu Arg Ser Val Glu Leu Phe Thr Arg Leu Thr Met Leu Gln
    610                 615                 620

Leu Ser Gln Leu Ala Asp Ser Leu Val Glu Val Thr Phe Gly Asp Gly
625                 630                 635                 640

Gln Met Ile Val Asp Lys Asn Asp Asp Ala Ser Ser Leu Tyr Ile Ile
                645                 650                 655

Gln Arg Gly Arg Val Lys Leu Lys Leu Ala Ala Asp Gln Val Asn Ser
            660                 665                 670

Asp Ala Trp Asp Leu Leu Ser Ser Gln Thr Lys Val Ala Gln Ser Ser
        675                 680                 685

Arg Glu Asp Gly Asn Tyr Val Phe Glu Ile Asp Glu Gly Gly His Phe
    690                 695                 700

Gly Glu Trp Ala Leu Phe Gly Glu Thr Ile Ala Phe Thr Ala Met Ser
705                 710                 715                 720

Val Gly Asp Val Thr Cys Ser Thr Ile Ala Lys Glu Lys Phe Asp Ser
                725                 730                 735

Ile Ile Gly Pro Leu Pro Lys Val Ser Gln Ser Asp Ser Lys Leu Lys
            740                 745                 750

Asp Ser Leu Val Pro Lys Gly His Gly Ala Asp Asp Ser Ser Phe Arg
        755                 760                 765

Lys Ala Gln Leu Ser Asp Leu Glu Trp Lys Met Cys Ile Tyr Ala Ala
    770                 775                 780

Asp Cys Ser Glu Ile Gly Leu Val Gln Leu Arg Gly Ser Asp Lys Ile
785                 790                 795                 800

Lys Ser Leu Lys Arg Phe Tyr Ile Lys Arg Val Lys Asp Leu His Lys
                805                 810                 815

Glu Lys His Val Phe Asp Glu Lys Asp Leu Met Lys Ser Leu Ser Gln
            820                 825                 830

Ser Thr Cys Val Pro Glu Val Leu Cys Thr Cys Ala Asp Gln Ser Tyr
        835                 840                 845

Leu Gly Ile Leu Leu Asn Cys Cys Leu Cys Cys Ser Leu Ala Ser Ile
    850                 855                 860

Leu His Ala Pro Leu Asn Glu Ser Ser Ala Arg Phe Tyr Ala Ala Ser
865                 870                 875                 880

Val Val Val Ala Leu Glu Asn Leu His Gln Arg Ser Ile Leu Tyr Arg
                885                 890                 895

Gly Val Ser Ala Asp Ile Leu Met Val Asp Arg Ser Gly His Leu Gln
            900                 905                 910

Leu Val Asp Phe Arg Phe Ala Lys Lys Leu Gln Gly Glu Arg Thr Tyr
```

-continued

```
        915                 920                 925

Thr Ile Cys Gly Ile Ala Asp Ser Leu Ala Pro Glu Ile Val Leu Gly
    930                 935                 940

Arg Gly His Gly Phe Ser Ala Asp Trp Trp Ala Leu Gly Val Leu Ile
945                 950                 955                 960

Tyr Phe Met Leu Gln Ser Asp Met Pro Phe Gly Ser Trp Arg Glu Ser
                965                 970                 975

Glu Leu Glu Pro Phe Ala Lys Ile Ala Lys Gly His Leu Val Met Pro
            980                 985                 990

Ser Thr Phe Ser Ile Glu Val Val  Asp Leu Ile Thr Lys  Leu Leu Glu
        995                 1000                1005

Val Asn  Glu Asn Ala Arg Leu  Gly Ala Lys Gly Ala  Glu Ser Val
    1010                 1015                1020

Lys Arg  His Pro Trp Phe Asp  Gly Ile Asp Trp Lys  Gln Ile Ala
    1025                 1030                1035

Asp Gly  Thr Tyr Thr Val Pro  Gln Glu Ile Thr Asp  Arg Val Asp
    1040                 1045                1050

Ser Tyr  Val Glu Thr Leu Thr  Glu Asp Leu Thr Ala  Ser Pro Ser
    1055                 1060                1065

Met Pro  Ser Glu Glu Thr Ala  Asp Gln Ala Ala Pro  Glu Trp Ile
    1070                 1075                1080

Gln Asp  Trp
    1085


<210> SEQ ID NO 58
<211> LENGTH: 484
<212> TYPE: DNA
<213> ORGANISM: tobacco mosaic virus

<400> SEQUENCE: 58

aagcttgcat gcctgcaggc tctagaggat cccccctcag aagaccagag ggctattgag      60

acttttcaac aaagggtaat atcgggaaac ctcctcggat tccattgccc agctatctgt     120

cacttcatcg aaaggacagt agaaaaggaa ggtggctcct acaaatgcca tcattgcgat     180

aaaggaaagg ctatcgttca agatgcctct accgacagtg gtcccaaaga tggaccccca     240

cccacgagga acatcgtgga aaaagaagac gttccaacca cgtcttcaaa gcaagtggat     300

tgatgtgata tctccactga cgtaagggat gacgcacaat cccactatcc ttcgcaagac     360

ccttcctcta tataaggaag ttcatttcat ttggagagga caggcttctt gagatccttc     420

aacaattacc aacaacaaca aacaacaaac aacattacaa ttactattta caattacagt     480

cgac                                                                  484


<210> SEQ ID NO 59
<211> LENGTH: 331
<212> TYPE: PRT
<213> ORGANISM: Arabidopsis thaliana

<400> SEQUENCE: 59

Met Gly His Cys Phe Ser Leu Pro Ser Ser Gln Ser Glu Ile His Glu
1               5                   10                  15

Asp Asn Glu His Gly Asp Gly Asn Val Val Cys Tyr Gly Glu Glu Phe
            20                  25                  30

Gly Leu Asp Gln Asp Leu Pro Val His Arg Leu Gly Ser Val Cys Ser
        35                  40                  45

Ile Gln Gly Thr Lys Val Leu Asn Gln Asp His Ala Val Leu Tyr Gln
```

```
    50                  55                  60

Gly Tyr Gly Thr Arg Asp Thr Glu Leu Cys Gly Val Phe Asp Gly His
65                  70                  75                  80

Gly Lys Asn Gly His Met Val Ser Lys Met Val Arg Asn Arg Leu Pro
                85                  90                  95

Ser Val Leu Leu Ala Leu Lys Glu Glu Leu Asn Gln Glu Ser Asn Val
            100                 105                 110

Cys Glu Glu Glu Ala Ser Lys Trp Glu Lys Ala Cys Phe Thr Ala Phe
        115                 120                 125

Arg Leu Ile Asp Arg Glu Leu Asn Leu Gln Val Phe Asn Cys Ser Phe
    130                 135                 140

Ser Gly Ser Thr Gly Val Val Ala Ile Thr Gln Gly Asp Asp Leu Val
145                 150                 155                 160

Ile Ala Asn Leu Gly Asp Ser Arg Ala Val Leu Gly Thr Met Thr Glu
                165                 170                 175

Asp Gly Glu Ile Lys Ala Val Gln Leu Thr Ser Asp Leu Thr Pro Asp
            180                 185                 190

Val Pro Ser Glu Ala Glu Arg Ile Arg Met Cys Lys Gly Arg Val Phe
        195                 200                 205

Ala Met Lys Thr Glu Pro Ser Ser Gln Arg Val Trp Leu Pro Asn Gln
    210                 215                 220

Asn Ile Pro Gly Leu Ala Met Ser Arg Ala Phe Gly Asp Phe Arg Leu
225                 230                 235                 240

Lys Asp His Gly Val Ile Ala Val Pro Glu Ile Ser Gln His Arg Ile
                245                 250                 255

Thr Ser Lys Asp Gln Phe Leu Val Leu Ala Thr Asp Gly Val Trp Asp
            260                 265                 270

Met Leu Ser Asn Asp Glu Val Val Ser Leu Ile Trp Ser Ser Gly Lys
        275                 280                 285

Lys Gln Ala Ser Ala Ala Lys Met Val Ala Glu Ala Ala Glu Ala Ala
    290                 295                 300

Trp Lys Lys Arg Leu Lys Tyr Thr Lys Val Asp Asp Ile Thr Val Ile
305                 310                 315                 320

Cys Leu Phe Leu Gln Asn Lys Glu Gln Pro Ser
                325                 330


<210> SEQ ID NO 60
<211> LENGTH: 326
<212> TYPE: PRT
<213> ORGANISM: Arabidopsis thaliana

<400> SEQUENCE: 60

Met Gly Phe Cys Phe Cys Leu Ser Ser Gly Gly Ser Thr Asp Lys Ser
1               5                   10                  15

Gln Ile Tyr Glu Ile Thr Asp Tyr Gly Gln Glu Asn Ala Val Leu Tyr
            20                  25                  30

Ser Asp His His Val Val Pro Gln Asn Leu Gly Ser Val Ser Ser Leu
        35                  40                  45

Ala Gly Gly Lys Gly Leu Asn Gln Asp Ala Ala Ile Leu His Leu Gly
    50                  55                  60

Tyr Gly Thr Glu Glu Gly Ala Leu Cys Gly Val Phe Asp Gly His Gly
65                  70                  75                  80

Pro Arg Gly Ala Phe Val Ser Lys Asn Val Arg Asn Gln Leu Pro Ser
                85                  90                  95
```

-continued

```
Ile Leu Leu Gly His Met Asn Asn His Ser Val Thr Arg Asp Trp Lys
            100                 105                 110

Leu Ile Cys Glu Thr Ser Cys Leu Glu Met Asp Lys Arg Ile Leu Lys
        115                 120                 125

Val Lys Lys Ile His Asp Cys Ser Ala Ser Gly Thr Thr Ala Val Leu
    130                 135                 140

Ala Val Lys His Gly Asn Gln Val Met Val Ala Asn Leu Gly Asp Ser
145                 150                 155                 160

Arg Ala Val Met Ile Gly Thr Ser Glu Asp Gly Glu Thr Lys Val Ala
                165                 170                 175

Gln Leu Thr Asn Asp Leu Lys Pro Ser Val Pro Ser Glu Ala Glu Arg
            180                 185                 190

Ile Arg Lys Arg Asn Gly Arg Val Leu Ala Leu Glu Ser Glu Pro His
        195                 200                 205

Ile Leu Arg Val Trp Leu Pro Thr Glu Asn Arg Pro Gly Leu Ala Met
    210                 215                 220

Ser Arg Ala Phe Gly Asp Phe Leu Leu Lys Ser Tyr Gly Val Ile Ala
225                 230                 235                 240

Thr Pro Gln Val Ser Thr His Gln Ile Thr Ser Ser Asp Gln Phe Leu
                245                 250                 255

Leu Leu Ala Ser Asp Gly Val Trp Asp Val Leu Ser Asn Glu Glu Val
            260                 265                 270

Ala Thr Val Val Met Lys Ser Ala Ser Glu Ala Gly Ala Ala Asn Glu
        275                 280                 285

Val Ala Glu Ala Ala Thr Asn Ala Trp Ile Gln Lys Phe Pro Thr Val
    290                 295                 300

Lys Ile Asp Asp Ile Ser Val Val Cys Leu Ser Leu Asn Lys Lys His
305                 310                 315                 320

Asn Pro Gln Pro Gln Ile
                325


<210> SEQ ID NO 61
<211> LENGTH: 491
<212> TYPE: PRT
<213> ORGANISM: Arabidopsis thaliana

<400> SEQUENCE: 61

Met Gly Leu Cys His Ser Lys Ile Asp Lys Thr Thr Arg Lys Glu Thr
1               5                   10                  15

Gly Ala Thr Ser Thr Ala Thr Thr Thr Val Glu Arg Gln Ser Ser Gly
            20                  25                  30

Arg Leu Arg Arg Pro Arg Asp Leu Tyr Ser Gly Gly Glu Ile Ser Glu
        35                  40                  45

Ile Gln Gln Val Val Gly Arg Leu Val Gly Asn Gly Ser Ser Glu Ile
    50                  55                  60

Ala Cys Leu Tyr Thr Gln Gln Gly Lys Lys Gly Thr Asn Gln Asp Ala
65                  70                  75                  80

Met Leu Val Trp Glu Asn Phe Cys Ser Arg Ser Asp Thr Val Leu Cys
                85                  90                  95

Gly Val Phe Asp Gly His Gly Pro Phe Gly His Met Val Ser Lys Arg
            100                 105                 110

Val Arg Asp Met Leu Pro Phe Thr Leu Ser Thr Gln Leu Lys Thr Thr
        115                 120                 125

Ser Gly Thr Glu Gln Ser Ser Ser Lys Asn Gly Leu Asn Ser Ala Pro
    130                 135                 140
```

```
Thr Cys Val Asp Glu Glu Gln Trp Cys Glu Leu Gln Leu Cys Glu Lys
145                 150                 155                 160

Asp Glu Lys Leu Phe Pro Glu Met Tyr Leu Pro Leu Lys Arg Ala Leu
                165                 170                 175

Leu Lys Thr Cys Gln Gln Met Asp Lys Glu Leu Lys Met His Pro Thr
            180                 185                 190

Ile Asn Cys Phe Cys Ser Gly Thr Thr Ser Val Thr Val Ile Lys Gln
        195                 200                 205

Gly Lys Asp Leu Val Val Gly Asn Ile Gly Asp Ser Arg Ala Val Leu
    210                 215                 220

Ala Thr Arg Asp Gln Asp Asn Ala Leu Val Ala Val Gln Leu Thr Ile
225                 230                 235                 240

Asp Leu Lys Pro Asp Leu Pro Ser Glu Ser Ala Arg Ile His Arg Cys
                245                 250                 255

Lys Gly Arg Val Phe Ala Leu Gln Asp Glu Pro Glu Val Ala Arg Val
            260                 265                 270

Trp Leu Pro Asn Ser Asp Ser Pro Gly Leu Ala Met Ala Arg Ala Phe
        275                 280                 285

Gly Asp Phe Cys Leu Lys Asp Tyr Gly Leu Ile Ser Val Pro Asp Ile
    290                 295                 300

Asn Tyr His Arg Leu Thr Glu Arg Asp Gln Tyr Ile Ile Leu Ala Thr
305                 310                 315                 320

Asp Gly Val Trp Asp Val Leu Ser Asn Lys Glu Ala Val Asp Ile Val
                325                 330                 335

Ala Ser Ala Pro Ser Arg Asp Thr Ala Ala Arg Ala Val Val Asp Thr
            340                 345                 350

Ala Val Arg Ala Trp Arg Leu Lys Tyr Pro Thr Ser Lys Asn Asp Asp
        355                 360                 365

Cys Ala Val Val Cys Leu Phe Leu Glu Asp Thr Ser Ala Gly Gly Thr
    370                 375                 380

Val Glu Val Ser Glu Thr Val Asn His Ser His Glu Glu Ser Thr Glu
385                 390                 395                 400

Ser Val Thr Ile Thr Ser Ser Lys Asp Ala Asp Lys Lys Glu Glu Ala
                405                 410                 415

Ser Thr Glu Thr Asn Glu Thr Val Pro Val Trp Glu Ile Lys Glu Glu
            420                 425                 430

Lys Thr Pro Glu Ser Cys Arg Ile Glu Ser Lys Lys Thr Thr Leu Ala
        435                 440                 445

Glu Cys Ile Ser Val Lys Asp Asp Glu Glu Trp Ser Ala Leu Glu Gly
    450                 455                 460

Leu Thr Arg Val Asn Ser Leu Leu Ser Ile Pro Arg Phe Phe Ser Gly
465                 470                 475                 480

Glu Leu Arg Ser Ser Ser Trp Arg Lys Trp Leu
                485                 490


<210> SEQ ID NO 62
<211> LENGTH: 504
<212> TYPE: PRT
<213> ORGANISM: Arabidopsis thaliana

<400> SEQUENCE: 62

Met Gly Leu Cys Tyr Ser Val Asp Arg Thr Thr Gly Lys Glu Pro Gly
1               5                   10                  15

Glu Ala Ser Ser Thr Ala Thr Thr Ala Glu Thr Val Glu Glu Arg Ser
```

-continued

```
            20                  25                  30

Gly Ser Gly Arg Trp Arg Arg Pro Arg Asp Leu Lys Gly Gly Gly Asp
        35                  40                  45

Ile Glu Gly Ile Pro Gln Val Leu Gly Arg Leu Val Ser Asn Gly Ser
    50                  55                  60

Ser Lys Ile Ala Cys Leu Tyr Thr Gln Gln Gly Lys Lys Gly Thr Asn
65                  70                  75                  80

Gln Asp Ala Met Leu Val Phe Glu Asn Phe Cys Ser Arg Asp Asp Thr
                85                  90                  95

Val Phe Cys Gly Val Phe Asp Gly His Gly Pro Phe Gly His Met Val
            100                 105                 110

Ala Lys Lys Val Arg Asp Thr Leu Pro Phe Thr Leu Leu Thr Gln Leu
        115                 120                 125

Lys Met Thr Ser Glu Ser Asp Gln Ser Ser Leu Val Gly Ala Asn Gly
    130                 135                 140

Phe Gln Ile Lys Cys Thr Glu Glu Glu Glu Val Gln Thr Thr Glu Ser
145                 150                 155                 160

Glu Gln Val Gln Lys Thr Glu Ser Val Thr Thr Met Asp Glu Gln Trp
                165                 170                 175

Cys Glu Leu Asn Pro Asn Val Asn Asn Asp Glu Leu Pro Glu Met Tyr
            180                 185                 190

Leu Pro Leu Lys His Ala Met Leu Lys Ser Cys Gln Gln Ile Asp Lys
        195                 200                 205

Glu Leu Lys Met His Pro Thr Ile Asp Cys Phe Cys Ser Gly Thr Thr
    210                 215                 220

Ser Val Thr Leu Ile Lys Gln Gly Glu Asp Leu Val Val Gly Asn Ile
225                 230                 235                 240

Gly Asp Ser Arg Ala Val Leu Ala Thr Arg Asp Glu Asp Asn Ala Leu
                245                 250                 255

Leu Ala Val Gln Leu Thr Ile Asp Leu Lys Pro Asp Leu Pro Gly Glu
            260                 265                 270

Ser Ala Arg Ile Gln Lys Cys Lys Gly Arg Val Phe Ala Leu Gln Asp
        275                 280                 285

Glu Pro Glu Val Ala Arg Val Trp Leu Pro Asn Ser Asp Ser Pro Gly
    290                 295                 300

Leu Ala Met Ala Arg Ala Phe Gly Asp Phe Cys Leu Lys Asp Tyr Gly
305                 310                 315                 320

Leu Ile Ser Val Pro Asp Ile Asn Tyr Arg Arg Leu Thr Glu Arg Asp
                325                 330                 335

Gln Phe Ile Ile Leu Ala Ser Asp Gly Val Trp Asp Val Leu Ser Asn
            340                 345                 350

Lys Glu Ala Val Asp Ile Val Ala Ser Ala Pro Ser Arg Ser Thr Ala
        355                 360                 365

Ala Arg Ala Leu Val Asp Thr Ala Val Arg Ser Trp Arg Ile Lys Tyr
    370                 375                 380

Pro Thr Ser Lys Asn Asp Asp Cys Thr Val Val Cys Leu Phe Leu Gln
385                 390                 395                 400

Asp Ser Ser Val Ala Met Glu Val Ser Thr Asn Val Lys Lys Asp Ser
                405                 410                 415

Pro Lys Glu Glu Ser Ile Glu Ser Val Thr Asn Ser Thr Ser Lys Glu
            420                 425                 430

Glu Asp Glu Ile Val Pro Val Lys Asp Glu Lys Ile Pro Glu Ser Cys
        435                 440                 445
```

Gly Ile Glu Ser Lys Met Met Thr Met Thr Leu Ala Glu Cys Ile Ser
450 455 460

Val Ala Gln Asp Asp Glu Glu Trp Ser Ala Leu Glu Gly Leu Thr Arg
465 470 475 480

Val Asn Ser Leu Leu Ser Ile Pro Arg Phe Leu Ser Gly Glu Leu Arg
485 490 495

Ser Thr Ser Trp Arg Lys Trp Leu
500

<210> SEQ ID NO 63
<211> LENGTH: 447
<212> TYPE: PRT
<213> ORGANISM: Arabidopsis thaliana

<400> SEQUENCE: 63

Met His Arg Pro Cys Leu Gly Met Gly Cys Cys Gly Ser Lys Met Gly
1 5 10 15

Lys Arg Gly Phe Ser Asp Arg Met Val Ser Leu His Asn Leu Val Ser
20 25 30

Ile Pro Asn Arg Ile Ile Gly Asn Gly Lys Ser Arg Ser Ser Cys Ile
35 40 45

Phe Thr Gln Gln Gly Arg Lys Gly Ile Asn Gln Asp Ala Met Ile Val
50 55 60

Trp Glu Asp Phe Met Ser Lys Asp Val Thr Phe Cys Gly Val Phe Asp
65 70 75 80

Gly His Gly Pro His Gly His Leu Val Ala Arg Lys Val Arg Asp Ser
85 90 95

Leu Pro Val Lys Leu Leu Ser Leu Leu Asn Ser Ile Lys Ser Lys Gln
100 105 110

Asn Gly Pro Ile Gly Thr Arg Ala Ser Lys Ser Asp Ser Leu Glu Ala
115 120 125

Glu Lys Glu Glu Ser Thr Glu Glu Asp Lys Leu Asn Phe Leu Trp Glu
130 135 140

Glu Ala Phe Leu Lys Ser Phe Asn Ala Met Asp Lys Glu Leu Arg Ser
145 150 155 160

His Pro Asn Leu Glu Cys Phe Cys Ser Gly Cys Thr Ala Val Thr Ile
165 170 175

Ile Lys Gln Gly Ser Asn Leu Tyr Met Gly Asn Ile Gly Asp Ser Arg
180 185 190

Ala Ile Leu Gly Ser Lys Asp Ser Asn Asp Ser Met Ile Ala Val Gln
195 200 205

Leu Thr Val Asp Leu Lys Pro Asp Leu Pro Arg Glu Ala Glu Arg Ile
210 215 220

Lys Gln Cys Lys Gly Arg Val Phe Ala Leu Gln Asp Glu Pro Glu Val
225 230 235 240

Ser Arg Val Trp Leu Pro Phe Asp Asn Ala Pro Gly Leu Ala Met Ala
245 250 255

Arg Ala Phe Gly Asp Phe Cys Leu Lys Asp Tyr Gly Val Ile Ser Ile
260 265 270

Pro Glu Phe Ser His Arg Val Leu Thr Asp Arg Asp Gln Phe Ile Val
275 280 285

Leu Ala Ser Asp Gly Val Trp Asp Val Leu Ser Asn Glu Glu Val Val
290 295 300

Glu Val Val Ala Ser Ala Thr Ser Arg Ala Ser Ala Ala Arg Leu Val

```
305                 310                 315                 320

Val Asp Ser Ala Val Arg Glu Trp Lys Leu Lys Tyr Pro Thr Ser Lys
                325                 330                 335

Met Asp Asp Cys Ala Val Val Cys Leu Phe Leu Asp Gly Arg Met Asp
            340                 345                 350

Ser Glu Thr Ser Asp Asn Glu Glu Gln Cys Phe Ser Ser Ala Thr Asn
        355                 360                 365

Ala Val Glu Ser Asp Glu Ser Gln Gly Ala Glu Pro Cys Leu Gln Arg
    370                 375                 380

Asn Val Thr Val Arg Ser Leu Ser Thr Asp Gln Glu Asn Asn Ser Tyr
385                 390                 395                 400

Gly Lys Val Ile Ala Glu Ala Asp Asn Ala Glu Lys Glu Lys Thr Arg
                405                 410                 415

Glu Gly Glu Gln Asn Trp Ser Gly Leu Glu Gly Val Thr Arg Val Asn
            420                 425                 430

Ser Leu Val Gln Leu Pro Arg Phe Pro Gly Glu Glu Pro Lys Thr
        435                 440                 445


<210> SEQ ID NO 64
<211> LENGTH: 448
<212> TYPE: PRT
<213> ORGANISM: Arabidopsis thaliana

<400> SEQUENCE: 64

Met Gly Ser Cys Leu Ser Ser Ser Gly Gly Gly Gly Ser Arg Arg Ser
1               5                   10                  15

Leu His Gly Ser Pro His Val Pro Gly Pro Gly Arg Arg Lys Arg Pro
            20                  25                  30

Pro Lys Arg Arg Pro Gly Ser Cys Ser Ser Ser Phe Asp Asn Thr Glu
        35                  40                  45

Glu Pro Leu Leu His Arg Ile Pro Gly Arg Met Phe Leu Asn Gly Ser
    50                  55                  60

Thr Asp Thr Val Ser Leu Phe Ser Gln Gln Gly Lys Lys Gly Pro Asn
65                  70                  75                  80

Gln Asp Ala Met Ile Val Trp Glu Asn Phe Gly Ser Met Glu Asp Thr
                85                  90                  95

Val Phe Cys Gly Val Phe Asp Gly His Gly Pro Tyr Gly His Ile Val
            100                 105                 110

Ala Lys Arg Val Arg Asp Leu Leu Pro Leu Lys Leu Gly Ser His Leu
        115                 120                 125

Glu Ser Tyr Val Ser Pro Glu Glu Val Leu Lys Glu Ile Ser Leu Asn
    130                 135                 140

Thr Asp Asp Arg Lys Ile Ser Glu Asp Leu Val His Ile Ser Ala Asn
145                 150                 155                 160

Gly Glu Ser Arg Val Tyr Asn Lys Asp Tyr Val Lys Asp Gln Asp Met
                165                 170                 175

Ile Gln Met Leu Ile Gly Ser Ile Val Lys Ala Tyr Arg Phe Met Asp
            180                 185                 190

Lys Glu Leu Lys Met Gln Val Asp Val Asp Cys Phe Cys Ser Gly Thr
        195                 200                 205

Thr Ala Val Thr Met Val Lys Gln Gly Gln His Leu Val Ile Gly Asn
    210                 215                 220

Ile Gly Asp Ser Arg Ala Val Leu Gly Val Arg Asn Lys Asp Asn Lys
225                 230                 235                 240
```

-continued

Leu Val Pro Phe Gln Leu Thr Glu Asp Leu Lys Pro Asp Val Pro Ala
245 250 255

Glu Ala Glu Arg Ile Lys Arg Cys Arg Gly Arg Ile Phe Ala Leu Arg
260 265 270

Asp Glu Pro Gly Val Ala Arg Leu Trp Leu Pro Asn His Asn Ser Pro
275 280 285

Gly Leu Ala Met Ala Arg Ala Phe Gly Asp Phe Cys Leu Lys Asp Phe
290 295 300

Gly Leu Ile Ser Val Pro Asp Val Ser Tyr Arg Arg Leu Thr Glu Lys
305 310 315 320

Asp Glu Phe Val Val Leu Ala Thr Asp Gly Ile Trp Asp Ala Leu Thr
325 330 335

Asn Glu Glu Val Val Lys Ile Val Ala Lys Ala Pro Thr Arg Ser Ser
340 345 350

Ala Gly Arg Ala Leu Val Glu Ala Ala Val Arg Asn Trp Arg Trp Lys
355 360 365

Phe Pro Thr Ser Lys Val Asp Asp Cys Ala Val Val Cys Leu Phe Leu
370 375 380

Asp Ser Glu Pro Asn Arg Leu Ser Thr Ala Ser Phe Ser Lys Glu Lys
385 390 395 400

His Ile Asn Asn Gly Val Thr Glu Pro Glu Pro Asp Thr Ala Ser Ser
405 410 415

Ser Thr Pro Asp Ser Gly Thr Gly Ser Pro Glu Leu Asn Gly Val Asn
420 425 430

Arg Ile Asp Thr Leu Val Asn Leu Pro Val Tyr Val Pro Thr Lys Glu
435 440 445

<210> SEQ ID NO 65
<211> LENGTH: 382
<212> TYPE: PRT
<213> ORGANISM: Arabidopsis thaliana

<400> SEQUENCE: 65

Met Gly Val Cys Cys Ser Lys Gly Thr Gly Ile Ile Val Glu His Gly
1 5 10 15

Ala Asp Asp Gly Asn Glu Cys Gly Asp Gly Glu Ala Glu Val Arg Asp
20 25 30

Thr Asn Asp Gly Ala Val Val Arg Thr Arg Gly Ser Ser Lys His Val
35 40 45

Ser Met Ser Ile Lys Gln Gly Lys Lys Gly Ile Asn Gln Asp Ala Met
50 55 60

Thr Val Trp Glu Asn Phe Gly Gly Glu Glu Asp Thr Ile Phe Cys Gly
65 70 75 80

Val Phe Asp Gly His Gly Pro Met Gly His Lys Ile Ser Arg His Val
85 90 95

Cys Glu Asn Leu Pro Ser Arg Val His Ser Lys Ile Arg Ser Ser Lys
100 105 110

Ser Ala Gly Asp Glu Asn Ile Glu Asn Asn Ser Ser Gln Ser Gln Glu
115 120 125

Glu Leu Phe Arg Glu Phe Glu Asp Ile Leu Val Thr Phe Phe Lys Gln
130 135 140

Ile Asp Ser Glu Leu Gly Leu Asp Ser Pro Tyr Asp Ser Phe Cys Ser
145 150 155 160

Gly Thr Thr Ala Val Thr Val Phe Lys Gln Ala Asp Cys Leu Val Ile
165 170 175

```
Ala Asn Leu Gly His Ser Arg Ala Val Leu Gly Thr Arg Ser Lys Asn
            180                 185                 190

Ser Phe Lys Ala Val Gln Leu Thr Val Asp Leu Lys Pro Cys Val Gln
        195                 200                 205

Arg Glu Ala Glu Arg Ile Val Ser Cys Lys Gly Arg Val Phe Ala Met
    210                 215                 220

Glu Glu Glu Pro Asp Val Tyr Arg Val Trp Met Pro Asp Asp Asp Cys
225                 230                 235                 240

Pro Gly Leu Ala Met Ser Arg Ala Phe Gly Asp Phe Cys Leu Lys Asp
                245                 250                 255

Tyr Gly Leu Val Cys Ile Pro Asp Val Phe Cys Arg Lys Val Ser Arg
            260                 265                 270

Glu Asp Glu Phe Val Val Leu Ala Thr Asp Gly Ile Trp Asp Val Leu
        275                 280                 285

Ser Asn Glu Glu Val Val Lys Val Val Gly Ser Cys Lys Asp Arg Ser
    290                 295                 300

Val Ala Ala Glu Met Leu Val Gln Arg Ala Ala Arg Thr Trp Arg Thr
305                 310                 315                 320

Lys Phe Pro Ala Ser Lys Ala Asp Asp Cys Ala Val Val Val Leu Tyr
                325                 330                 335

Leu Asn His Arg Pro Tyr Pro Arg Glu Gly Asn Val Ser Arg Ala Ile
            340                 345                 350

Ser Thr Ile Ser Trp Arg Ser Asn Lys Ser Asn Asn Glu Cys Tyr Gly
        355                 360                 365

Ala Ala Pro Leu Ser Pro Leu Gly Leu Ser Gln Arg Val Ser
    370                 375                 380
```

<210> SEQ ID NO 66
<211> LENGTH: 514
<212> TYPE: PRT
<213> ORGANISM: Arabidopsis thaliana

<400> SEQUENCE: 66

```
Met Gly Cys Ala Tyr Ser Lys Thr Cys Ile Gly Gln Ile Cys Ala Thr
1               5                   10                  15

Lys Glu Asn Ser Ile Arg Gln Thr His Gln Gln Ala Pro Ser Arg Gly
            20                  25                  30

Gly Thr Arg Ala Thr Ala Ala Ala Ala Ala Val Glu Glu Asp Asn Pro
        35                  40                  45

Val Phe Asn Phe Ser Ser Asp Ala Val Asp Asp Val Asp Asn Asp Glu
    50                  55                  60

Ile His Gln Leu Gly Leu Ser Arg Asp Gln Glu Trp Gly Ile Thr Arg
65                  70                  75                  80

Leu Ser Arg Val Ser Ser Gln Phe Leu Pro Pro Asp Gly Ser Arg Val
                85                  90                  95

Val Lys Val Pro Ser Cys Asn Tyr Glu Leu Arg Cys Ser Phe Leu Ser
            100                 105                 110

Gln Arg Gly Tyr Tyr Pro Asp Ala Leu Asp Lys Ala Asn Gln Asp Ser
        115                 120                 125

Phe Ala Ile His Thr Pro Phe Gly Ser Asn Ser Asp Asp His Phe Phe
    130                 135                 140

Gly Val Phe Asp Gly His Gly Glu Phe Gly Ala Gln Cys Ser Gln Phe
145                 150                 155                 160

Val Lys Arg Arg Leu Cys Glu Asn Leu Leu Arg His Gly Arg Phe Arg
```

```
                165                 170                 175

Val Asp Pro Ala Glu Ala Cys Asn Ser Ala Phe Leu Thr Thr Asn Ser
            180                 185                 190

Gln Leu His Ala Asp Leu Val Asp Asp Ser Met Ser Gly Thr Thr Ala
        195                 200                 205

Ile Thr Val Met Val Arg Gly Arg Thr Ile Tyr Val Ala Asn Ala Gly
    210                 215                 220

Asp Ser Arg Ala Val Leu Ala Glu Lys Arg Asp Gly Asp Leu Val Ala
225                 230                 235                 240

Val Asp Leu Ser Ile Asp Gln Thr Pro Phe Arg Pro Asp Glu Leu Glu
                245                 250                 255

Arg Val Lys Leu Cys Gly Ala Arg Val Leu Thr Leu Asp Gln Ile Glu
            260                 265                 270

Gly Leu Lys Asn Pro Asp Val Gln Cys Trp Gly Thr Glu Glu Asp Asp
        275                 280                 285

Asp Gly Asp Pro Pro Arg Leu Trp Val Pro Asn Gly Met Tyr Pro Gly
    290                 295                 300

Thr Ala Phe Thr Arg Ser Ile Gly Asp Ser Ile Ala Glu Thr Ile Gly
305                 310                 315                 320

Val Val Ala Asn Pro Glu Ile Ala Val Val Glu Leu Thr Pro Asp Asn
                325                 330                 335

Pro Phe Phe Val Val Ala Ser Asp Gly Val Phe Glu Phe Ile Ser Ser
            340                 345                 350

Gln Thr Val Val Asp Met Val Ala Lys His Lys Asp Pro Arg Asp Ala
        355                 360                 365

Cys Ala Ala Ile Val Ala Glu Ser Tyr Arg Leu Trp Leu Gln Tyr Glu
    370                 375                 380

Thr Arg Thr Asp Asp Ile Thr Ile Ile Val Val His Ile Asp Gly Leu
385                 390                 395                 400

Lys Asp Asp Ala Pro Arg Gln Leu Ser Ser Thr Gly Thr Gln Leu Gln
                405                 410                 415

Pro Pro Ile Pro Gln Val Val Glu Leu Thr Gly Ser Glu Ser Pro Ser
            420                 425                 430

Thr Phe Gly Trp Asn Ser Lys Asn Gln Arg Val Arg His Asp Leu Ser
        435                 440                 445

Arg Ala Arg Ile Arg Ala Ile Glu Asn Ser Leu Glu Asn Gly His Ala
    450                 455                 460

Trp Val Pro Pro Ser Pro Ala His Arg Lys Thr Trp Glu Glu Glu Val
465                 470                 475                 480

Arg Val Leu Val Cys Phe Val Phe Ala Gln Pro Ile Arg Asn Ala Ser
                485                 490                 495

Ser His Ser Tyr Ile Arg Arg Leu Asn Ala Gly Phe Ser Arg Ala Gly
            500                 505                 510

Thr His


<210> SEQ ID NO 67
<211> LENGTH: 348
<212> TYPE: PRT
<213> ORGANISM: Arabidopsis thaliana

<400> SEQUENCE: 67

Met Gly Cys Val Gln Cys Lys Cys Cys Ser Arg Tyr Pro Ser Ser Ser
1               5                   10                  15

Ser Asp Gly Asp Ser Arg Gly Pro Leu Glu Ala Asn Gly Val Leu Lys
```

-continued

```
            20                  25                  30

Gly Lys Asp Gln Lys Pro Leu Gly Ser Ile His Val Pro Ser Pro Asn
        35                  40                  45

Phe Asp Met Val Tyr Ser Val Leu Ser Gln Arg Gly Tyr Tyr Pro Asp
    50                  55                  60

Ser Pro Asp Lys Glu Asn Gln Asp Thr Tyr Cys Ile Lys Thr Glu Leu
65                  70                  75                  80

Gln Gly Asn Pro Asn Val His Phe Phe Gly Val Phe Asp Gly His Gly
                85                  90                  95

Val Leu Gly Thr Gln Cys Ser Asn Phe Val Lys Glu Arg Val Val Glu
            100                 105                 110

Met Leu Ser Glu Asp Pro Thr Leu Leu Glu Asp Pro Glu Lys Ala Tyr
        115                 120                 125

Lys Ser Ala Phe Leu Arg Val Asn Glu Glu Leu His Asp Ser Glu Ile
    130                 135                 140

Asp Asp Ser Met Ser Gly Thr Thr Ala Ile Thr Val Leu Val Val Gly
145                 150                 155                 160

Asp Lys Ile Tyr Val Ala Asn Val Gly Asp Ser Arg Ala Val Leu Ala
                165                 170                 175

Val Lys Asp Arg Asn Arg Ile Leu Ala Glu Asp Leu Ser Tyr Asp Gln
            180                 185                 190

Thr Pro Phe Arg Lys Asp Glu Cys Glu Arg Val Lys Ala Cys Gly Ala
        195                 200                 205

Arg Val Leu Ser Val Asp Gln Val Glu Gly Leu Lys Asp Pro Asn Ile
    210                 215                 220

Gln Thr Trp Ala Asn Glu Glu Ser Glu Gly Gly Asp Pro Pro Arg Leu
225                 230                 235                 240

Trp Val Gln Asn Gly Met Tyr Pro Gly Thr Ala Phe Thr Arg Ser Val
                245                 250                 255

Gly Asp Phe Thr Ala Glu Ser Ile Gly Val Ile Ala Glu Pro Glu Val
            260                 265                 270

Ser Met Val His Leu Ser Pro Asn His Leu Phe Phe Val Val Ala Ser
        275                 280                 285

Asp Gly Ile Phe Glu Phe Leu Pro Ser Gln Ala Val Val Asp Met Val
    290                 295                 300

Gly Arg Tyr Ala Asp Pro Arg Asp Gly Cys Ala Ala Ala Ala Ala Glu
305                 310                 315                 320

Ser Tyr Lys Leu Trp Leu Glu His Glu Asn Arg Thr Asp Asp Ile Thr
                325                 330                 335

Ile Ile Ile Val Gln Ile Lys Lys Leu Ser Asn Glu
            340                 345
```